(12) United States Patent
Chi et al.

(10) Patent No.: US 11,931,431 B2
(45) Date of Patent: Mar. 19, 2024

(54) PSMA-TARGETED RADIOPHARMACEUTICAL FOR DIAGNOSING AND TREATING PROSTATE CANCER

(71) Applicant: FUTURECHEM CO., LTD, Seoul (KR)

(72) Inventors: Dae Yoon Chi, Seoul (KR); Byoung Se Lee, Seoul (KR); So Young Chu, Seoul (KR); Hyeon Jin Jeong, Seoul (KR); Min Hwan Kim, Seoul (KR); Kyo Chul Lee, Seoul (KR); Yong Jin Lee, Seoul (KR)

(73) Assignee: FUTURECHEM CO., LTD, Seoul (KR)

( * ) Notice: Subject to any disclaimer, the term of this patent is extended or adjusted under 35 U.S.C. 154(b) by 825 days.

(21) Appl. No.: 16/981,432

(22) PCT Filed: Mar. 29, 2019

(86) PCT No.: PCT/KR2019/003716
§ 371 (c)(1),
(2) Date: Sep. 16, 2020

(87) PCT Pub. No.: WO2019/190266
PCT Pub. Date: Oct. 3, 2019

(65) Prior Publication Data
US 2021/0106701 A1    Apr. 15, 2021

(30) Foreign Application Priority Data

Mar. 30, 2018 (KR) .................. 10-2018-0037226

(51) Int. Cl.
*A61K 51/04* (2006.01)
*A61P 35/00* (2006.01)
*C07F 5/00* (2006.01)

(52) U.S. Cl.
CPC .......... *A61K 51/0487* (2013.01); *A61P 35/00* (2018.01); *C07F 5/003* (2013.01)

(58) Field of Classification Search
None
See application file for complete search history.

(56) References Cited

U.S. PATENT DOCUMENTS

| 2013/0034494 A1 | 2/2013 | Babich et al. ............... 424/1.65 |
| 2014/0255306 A1 | 9/2014 | Babich et al. ........... C07F 5/003 |
| 2017/0081298 A1 | 3/2017 | Ray et al. ......................... 257/2 |

FOREIGN PATENT DOCUMENTS

| JP | 2014-524419 | 9/2014 |
| WO | 2013/022797 | 2/2013 |
| WO | 2015/055318 | 4/2015 |
| WO | WO2017/165473 A1 | 9/2017 |
| WO | 2019/246445 | 12/2019 |

OTHER PUBLICATIONS

Banerjee et al., "Effect of Chelators on the Pharmaconkinetics of 99mtc-Labeled Imaging Agents for the Prostate-Specific Membrane Antigen (PSMA)" J Med. Chem. 2013(56):6108-6121.
Kumar et al., "Design of a Small-Molecule Durg Conjugate for Prostate Cancer Targeted Theranostics" Bioconjugate Chem. 2016(27):1681-1689.
Pilai et al., "Radiolabeled Enzyme Inhibitors and Binding Agents Targeting PSMA: Effective Theranostic Tools for Imaging and Therapy of Prostate Cancer" Nuclear Med. Biol. 2016(43):692-720.
Extended European Search Report in EP 19775196.9 dated Dec. 11, 2020.
Eder et al. "68Ga-Complex Lipophilicity and the Targeting Property of a Urea-Based PSMA Inhibitor for PET Imaging" Bioconjugate Chemistry 2012 23:688-697.

*Primary Examiner* — Nissa M Westerberg
(74) *Attorney, Agent, or Firm* — LICATA & TYRRELL P.C.

(57) ABSTRACT

The present invention relates to a pharmaceutical composition for diagnosing and treating prostate cancer, capable of targeting PSMA, and a compound provided by one aspect of the present invention has a glutamine-urea-lysine compound to which a radioactive metal-coupled chelator is structurally coupled and to which an aryl group that can additionally bind to PSMA protein is coupled. Coupling between the glutamine-urea-lysine compound and the chelator includes a polar spacer so as to serve the role of reducing in vivo nonspecific coupling and exhibit an effect of being rapidly removed from vital organs, but not from prostate cancer. These characteristics lower the radiation exposure, which is caused by a therapeutic radioisotope-coupled compound, to normal tissue and organs, and thus reduce side effects. In addition, a compound that contains a phenyl group having a coupling force with albumin has an increased residence time in the blood, thereby becoming more accumulated in prostate cancer.

12 Claims, 4 Drawing Sheets

PSMA-TARGETED RADIOPHARMACEUTICAL FOR DIAGNOSING AND TREATING PROSTATE CANCER

This patent application is the National Stage of International Application No. PCT/KR2019/003716 filed Mar. 29, 2019, which claims the benefit of priority from Korean Application No. 10-2018-0037226, filed Mar. 30, 2018, teachings of each of which are herein incorporated by reference in their entirety.

BACKGROUND OF THE INVENTION

1. Field of the Invention

The present invention relates to a PSMA-targeted radiopharmaceutical for diagnosing and treating prostate cancer.

2. Description of the Related Art

Prostate cancer is the most common male cancer in the world and ranks second in mortality. Prostate cancer usually develops in men over 50, and the number of patients increases rapidly with age. It usually progresses slowly, but when it develops into a malignant metastasis, it is extremely difficult to treat. The metastasis usually begins to the lymph nodes, pelvic bones, vertebrae and bladder around prostate cancer and gradually spreads throughout the body.

Prostate-specific antigen test (PSA test) and digital rectal examination are currently used primarily for prostate cancer diagnosis, and transrectal ultrasonography, CT, MRI and WBBS (Whole body bone scan) imaging are also used. Biopsies for prostate cancer diagnosis are also being conducted. However, in most cases the diagnostic accuracy is low and early diagnosis of the disease is difficult. In addition, it is difficult to determine metastasis and difficult to distinguish from benign diseases such as prostate hyperplasia and prostatitis.

PET (Positron Emission Tomography) is a medical imaging technique that diagnoses a disease using a short half-life radioactive isotope emitting positrons. This technique can be used for early diagnosis of a disease, evaluation of treatment and confirmation of metastasis/recurrence.

[$^{18}$F]FDG is a representative PET radiopharmaceutical used for cancer diagnosis because it can observe the enhanced glucose metabolism of cancer cells. However, prostate cancer has a characteristic that it is difficult to detect early or diagnose disease progression because the intake of [$^{18}$F]FDG is not high. Choline is a material used for the biosynthesis of phosphatidylcholine, which is essential for cell membrane formation, and [$^{11}$C]Choline and [$^{18}$F]fluorocholine are known to be more suitable for diagnosing prostate cancer than [$^{18}$F]FDG. However, they have low sensitivity to diagnose prostate cancer early, lymph node metastasis, and recurrence, and it is difficult to distinguish prostate cancer from other cancers.

Prostate-Specific Membrane Antigen (PSMA) is a protein that is specifically over-expressed in prostate cancer and has an enzyme activity that degrades N-acetyl-L-aspartyl-glutamate (NAAL). It is known that a compound having a glutamic acid-urea-lysine (GUL) structure dose not decompose into analogues of NAAL and binds to PSMA very selectively. To date, several compounds with GUL as a basic structure have been developed, and among them, the compounds labeled with F-18 (half-life: 110 minutes) are being developed as PET radiopharmaceuticals for diagnosing prostate cancer.

In addition to F-18, Ga-68 is a radioactive metal that emits positrons, and has a feature of easily complexing with a chelator bound to a precursor, and a $^{68}$Ga-labeled GUL compound can also be used as a PET radiopharmaceutical for diagnosing prostate cancer.

In the case of a 68Ga-labeled GUL compound, it can be used as a prostate cancer targeted therapy by replacing Ga-68, a positron emitting isotope, with a therapeutic radioactive metal that emits beta rays or alpha particles. In the case of $^{68}$Ga-PSMA-617, a $^{68}$Ga-labeled compound, a clinical study is underway in which $^{177}$Lu-PSMA-617 labeled with Lu-177 (lutetium-177), which emits beta rays, is synthesized instead of Ga-68 and used in prostate cancer patients. It has been reported that most of the prostate cancer that has spread throughout the body is eliminated by repeated administration of 3 times.

In addition, a PSMA-targeted therapy labeled with an alpha-particle-emitting isotope is also being developed, and since it emits more energy than beta rays, the therapeutic effect thereof is better. Representative nuclides include Ac-225 (actinium-225), Bi-213 (bismuth-213), At-211 (astatine-211), etc. Currently, Xofigo® is used to treat prostate cancer that has metastasized to bone, but it is an injection of $^{223}$Ra—RaCl$_2$ (radium dichloride), which has no therapeutic effect on prostate cancer formed other than bone.

The present inventors have completed the present invention after confirming that the new structured PSMA-targeted compounds labeled with a radioactive metal have high binding force and selectivity to PSMA, and excellent pharmacokinetic properties.

SUMMARY OF THE INVENTION

It is an object of the present invention to provide a compound in which a radioactive metal-coupled chelator is coupled to a glutamic acid-urea-lysine compound having excellent binding force to PSMA protein and showing excellent pharmacokinetic properties in vivo, a stereoisomer thereof, a hydrate thereof, or a pharmaceutically acceptable salt thereof.

It is another object of the present invention to provide a compound in which a chelator is coupled to a glutamic acid-urea-lysine compound having excellent binding force to PSMA protein and showing excellent pharmacokinetic properties in vivo, a stereoisomer thereof, a hydrate thereof, or a pharmaceutically acceptable salt thereof.

It is another object of the present invention to provide a composition for diagnosing prostate cancer comprising the compound as an active ingredient.

It is another object of the present invention to provide a pharmaceutical composition for preventing or treating prostate cancer comprising the compound as an active ingredient.

It is another object of the present invention to provide a method for treating cancer, comprising a step of administering the compound, the stereoisomer thereof, the hydrate thereof, or the pharmaceutically acceptable salt thereof to an individual or a subject in need.

It is another object of the present invention to provide the compound, the stereoisomer thereof, the hydrate thereof, or the pharmaceutically acceptable salt thereof for the treatment of cancer.

It is another object of the present invention to provide a use of the compound, the stereoisomer thereof, the hydrate thereof, or the pharmaceutically acceptable salt thereof for the preparation of a drug for treating cancer.

To achieve the above objects, in one aspect of the present invention, the present invention provides a compound represented by formula 1 below, a stereoisomer thereof, a hydrate thereof, or a pharmaceutically acceptable salt thereof.

[Formula 1]

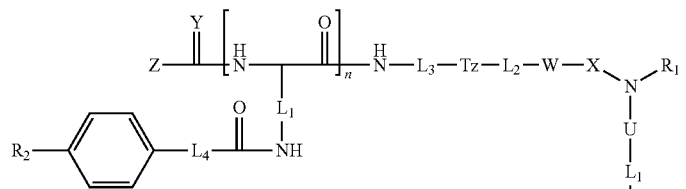
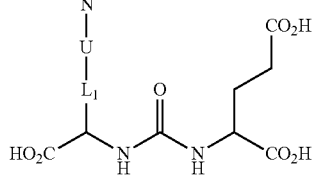

In formula 1,
L₁ is —(CH₂)$_a$—, wherein a is an integer of 1~8;
U is a bond, or —C(O)—;
R₁ is hydrogen, or -L₅-CO₂H, wherein L₅ is —(CH₂)$_b$—, wherein b is an integer of 1~6;
X is a bond, or —C(O)—;
W is a bond, or —NA₁-, A₁ is hydrogen, or —(CH₂)$_c$-pyridyl, wherein c is an integer of 0~3;
L₂ is a bond, or —(CH₂)$_d$—, wherein d is an integer of 1~8;
Tz is a bond,

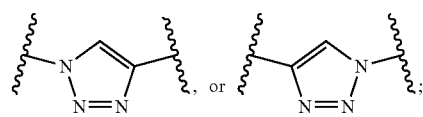 [SMILES: *c1cn(*)nn1 ; *c1cn(*)nn1]

L₃ is C$_{1-12}$ straight or branched alkylene, wherein one or more carbon atoms in alkylene can be replaced by oxygen atoms;
L₄ is —(CH₂)$_e$—, wherein e is an integer of 1~6;
n is an integer of 0~1;
R₂ is hydrogen, C$_{1-5}$ straight or branched alkyl, or halogen;
Y is oxygen or sulfur;
Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

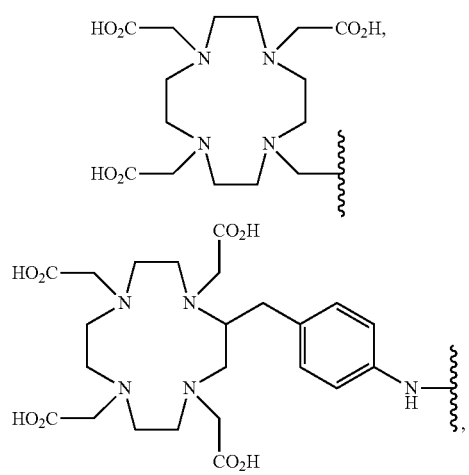

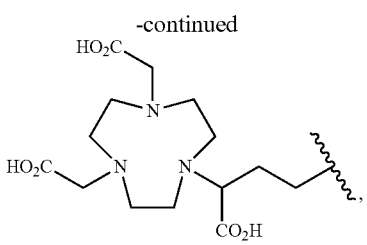

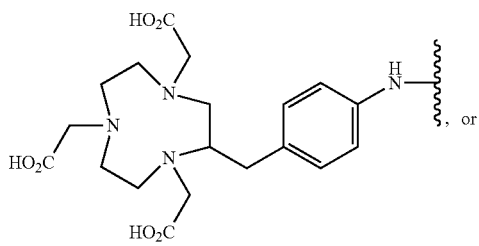

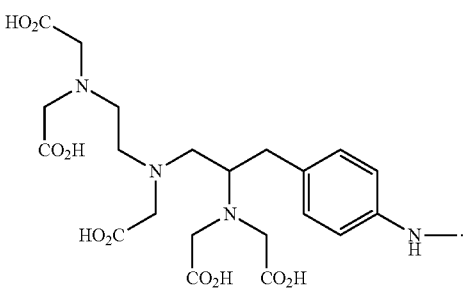

In another aspect of the present invention, the present invention provides a compound represented by formula 2 below, a stereoisomer thereof, a hydrate thereof, or a pharmaceutically acceptable salt thereof.

[Formula 2]

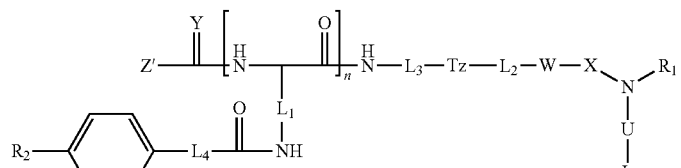

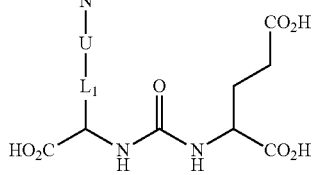

In formula 2, $L_1$ is —$(CH_2)_a$—, wherein a is an integer of 1~8;

U is a bond, or —C(O)—;

$R_1$ is hydrogen, or -$L_5$-$CO_2H$, wherein $L_5$ is —$(CH_2)_b$—, wherein b is an integer of 1~6;

X is a bond, or —C(O)—;

W is a bond, or —$NA_1$-, $A_1$ is hydrogen, or —$(CH_2)_c$-pyridyl, wherein c is an integer of 0~3;

$L_2$ is a bond, or —$(CH_2)_d$—, wherein d is an integer of 1~8;

Tz is a bond,

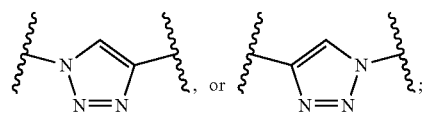 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;

$L_4$ is —$(CH_2)_e$—, wherein e is an integer of 1~6;

n is an integer of 0~1;

$R_2$ is hydrogen, $C_{1-5}$ straight or branched alkyl, or halogen;

Y is oxygen or sulfur;

Z' is a chelator, wherein the chelator is

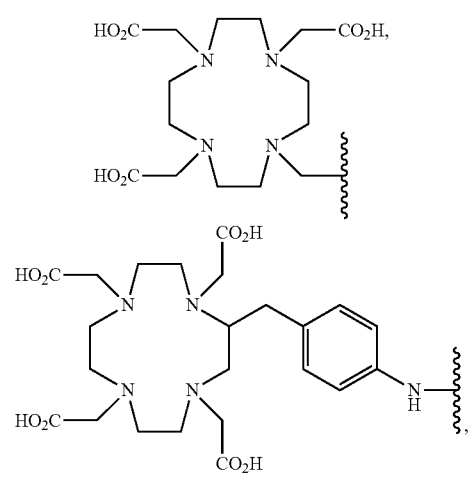

-continued

In another aspect of the present invention, the present invention provides a composition for diagnosing prostate cancer comprising the compound, the stereoisomer thereof, the hydrate thereof, or the pharmaceutically acceptable salt thereof as an active ingredient.

In another aspect of the present invention, the present invention provides a pharmaceutical composition for preventing or treating prostate cancer comprising the compound, the stereoisomer thereof, the hydrate thereof, or the pharmaceutically acceptable salt thereof as an active ingredient.

In another aspect of the present invention, the present invention provides a method for treating cancer, comprising a step of administering the compound, the stereoisomer thereof, the hydrate thereof, or the pharmaceutically acceptable salt thereof to an individual or a subject in need.

In another aspect of the present invention, the present invention provides the compound, the stereoisomer thereof, the hydrate thereof, or the pharmaceutically acceptable salt thereof for the treatment of cancer.

In another aspect of the present invention, the present invention provides a use of the compound, the stereoisomer thereof, the hydrate thereof, or the pharmaceutically acceptable salt thereof for the preparation of a drug for treating cancer.

Advantageous Effect

The compounds provided by one aspect of the present invention in which carboxylic acid bound to lysine of Glutamic acid-urea-Lysine (GUL) is introduced form strong salt bridge interaction with the arginine patch at the PSMA protein binding site, resulting in high binding power. These compounds are characterized by rapid background radiation removal effect and low non-specific binding in vivo due to the hydrophilic characteristics of carboxylic acid. In addition, the compounds are ingested at high concentrations in tumors or cancers expressing PSMA protein by maintaining a long residence time in blood.

DESCRIPTION OF THE PREFERRED EMBODIMENTS

Figure 1:
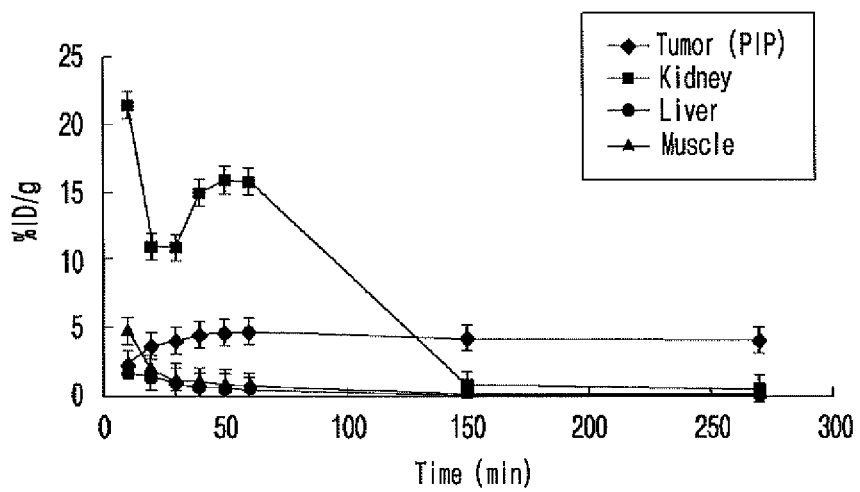
FIG. 1 is a graph showing the results of quantitative analysis of MicroPET/CT images acquired for 270 minutes after the administration of [$^{68}$Ga]1e.

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

In one aspect of the present invention, the present invention provides a pharmaceutical composition for preventing or treating cancer comprising a compound represented by formula 1 below, a stereoisomer thereof, a hydrate thereof, or a pharmaceutically acceptable salt thereof as an active ingredient.

[Formula 1]

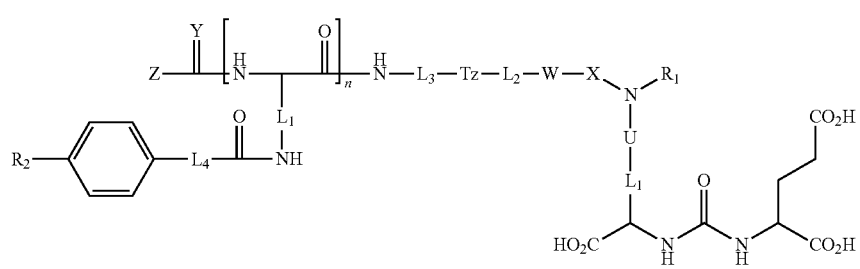

In formula 1,
$L_1$ is —(CH$_2$)$_a$—, wherein a is an integer of 1~8;
U is a bond, or —C(O)—;
$R_1$ is hydrogen, or -$L_5$-CO$_2$H, wherein $L_5$ is —(CH$_2$)$_b$—, wherein b is an integer of 1~6;
X is a bond, or —C(O)—;
W is a bond, or —NA$_1$-, A$_1$ is hydrogen, or —(CH$_2$)$_c$-pyridyl, wherein c is an integer of 0~3;
$L_2$ is a bond, or —(CH$_2$)$_d$—, wherein d is an integer of 1~8;
Tz is a bond,

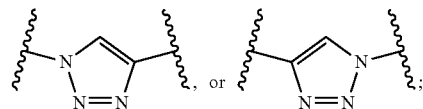

$L_3$ is C$_{1-12}$ straight or branched alkylene, wherein one or more carbon atoms in alkylene can be replaced by oxygen atoms;
$L_4$ is —(CH$_2$)$_e$—, wherein e is an integer of 1~6;
n is an integer of 0~1;
$R_2$ is hydrogen, C$_{1-5}$ straight or branched alkyl, or halogen;

Y is oxygen or sulfur;
Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

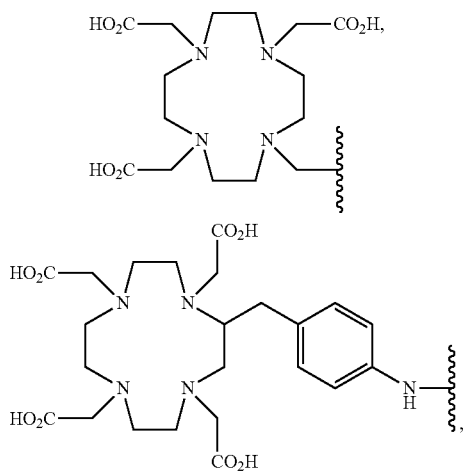

-continued

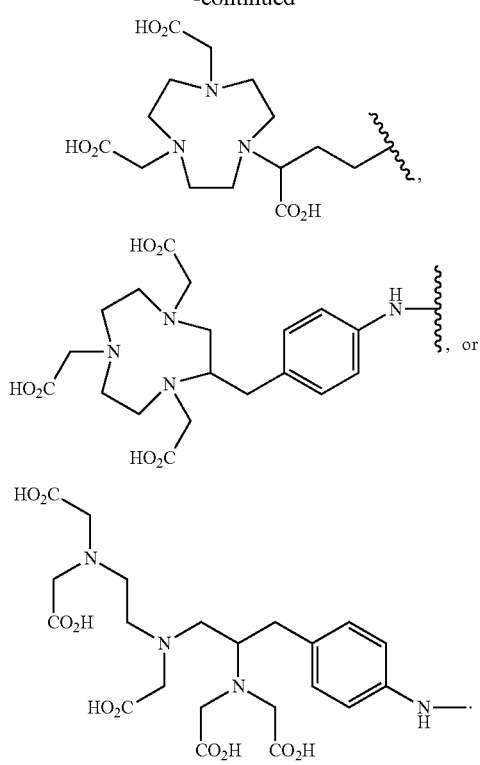

, or

In another aspect of the present invention, $L_1$ is —$(CH_2)_a$—, wherein a is an integer of 1~6;

U is a bond, or —C(O)—;

$R_1$ is hydrogen, or -$L_5$-$CO_2H$, wherein $L_5$ is —$(CH_2)_b$—, wherein b is an integer of 1~4;

X is a bond, or —C(O)—;

W is a bond, or —$NA_1$-, $A_1$ is hydrogen, or —$(CH_2)_c$-pyridyl, wherein c is an integer of 0~1;

$L_2$ is a bond, or —$(CH_2)_d$—, wherein d is an integer of 1~6;

Tz is a bond,

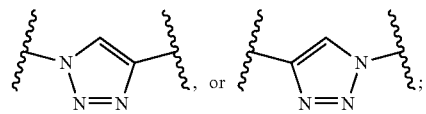

;

$L_3$ is $C_{1-12}$ straight or branched alkylene, wherein one or more carbon atoms in alkylene can be replaced by oxygen atoms;

$L_4$ is —$(CH_2)_e$—, wherein e is an integer of 2~4;

n is an integer of 0~1;

$R_2$ is hydrogen, $C_{1-3}$ straight or branched alkyl, or halogen;

Y is oxygen or sulfur;

Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

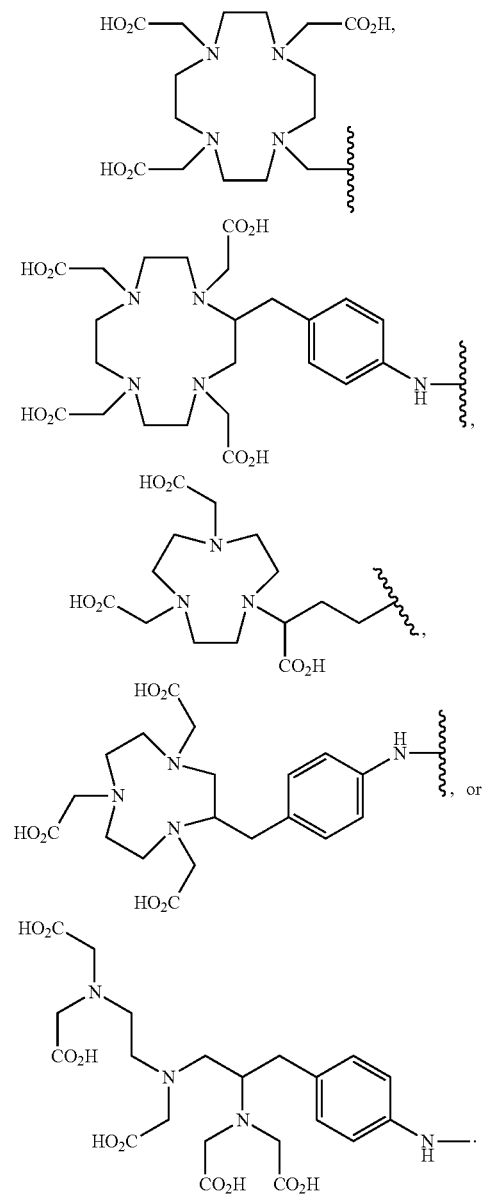

In another aspect of the present invention, $L_1$ is —$(CH_2)_a$—, wherein a is an integer of 2~4;

U is a bond, or —C(O)—;

$R_1$ is hydrogen, or -$L_5$-$CO_2H$, wherein $L_5$ is —$(CH_2)_b$—, wherein b is an integer of 1~2;

X is a bond, or —C(O)—;

W is a bond, or —$NA_1$-, wherein $A_1$ is hydrogen or pyridyl;

$L_2$ is a bond, or —$(CH_2)_d$—, wherein d is an integer of 1~2;

Tz is a bond,

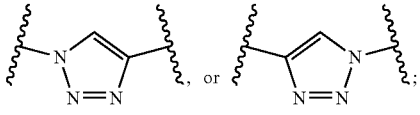 [SMILES: *c1cn(*)nn1 ; *c1cn(*)nn1]

;

$L_3$ is $C_{1-12}$ straight or branched alkylene, wherein one or more carbon atoms in alkylene can be replaced by oxygen atoms;

$L_4$ is —$(CH_2)_3$—;

n is an integer of 0~1;

$R_2$ is hydrogen, methyl or halogen;

Y is oxygen;

Z is a chelator including a radioactive metal, wherein the radioactive metal is Ga-68, Cu-64, or Lu-177, and the chelator can be

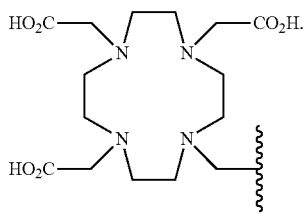 [SMILES: *CN1CCN(CC(=O)O)CCN(CC(=O)O)CCN(CC(=O)O)CC1]

In another aspect of the present invention, the compound represented by formula 1 can be a compound represented by formula 1-1 below.

[Formula 1-1]

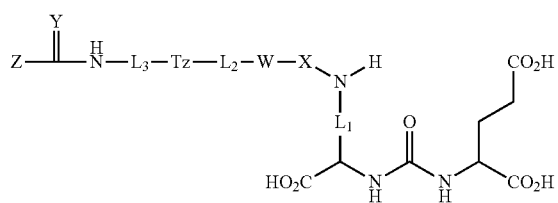

In formula 1-1, $L_1$ is —$(CH_2)_a$—, wherein a is an integer of 1~8;

X is a bond, or —C(O)—;

W is a bond or —$NA_1$-, wherein $A_1$ is hydrogen or —$(CH_2)_c$-pyridyl, wherein c is an integer of 0~3;

$L_2$ is a bond or —$(CH_2)_d$—, wherein d is an integer of 1~8;

Tz is a bond,

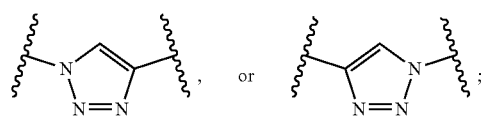 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;

Y is oxygen or sulfur;

Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

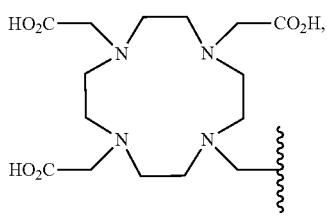

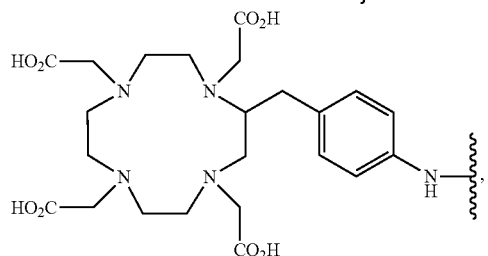

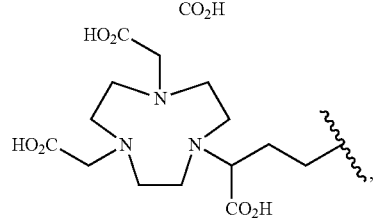

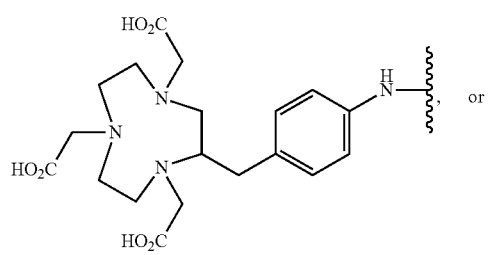

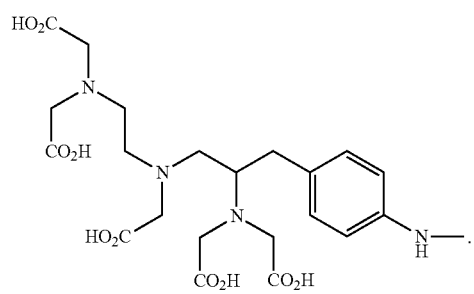

In another aspect of the present invention, the compound represented by formula 1 can be a compound represented by formula 1-2 below.

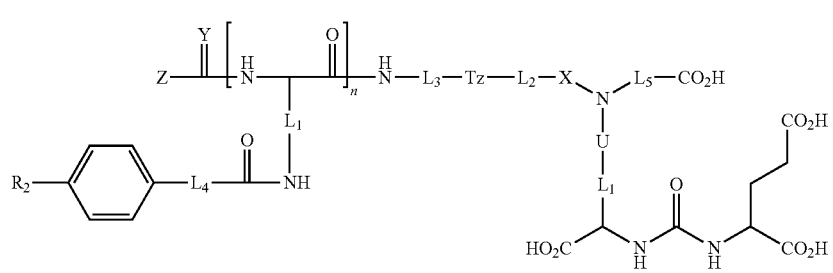

[Formula 1-2]

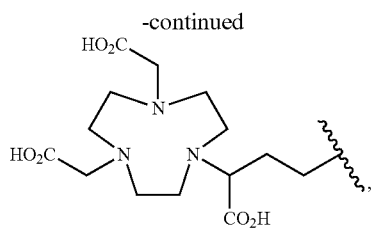

In formula 1-2, $L_1$ is —$(CH_2)_a$—, wherein a is an integer of 1~8;

U is a bond, or —C(O)—;

X is a bond, or —C(O)—;

$L_2$ is a bond or —$(CH_2)_d$—, wherein d is an integer of 1~8;

Tz is a bond,

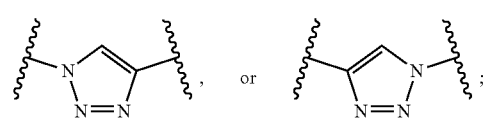 or ;

$L_3$ is $C_{1-12}$ straight or branched alkylene, wherein one or more carbon atoms in alkylene can be replaced by oxygen atoms;

$L_4$ is —$(CH_2)_e$—, wherein e is an integer of 1~6;

n is an integer of 0~1;

$R_2$ is hydrogen, $C_{1-5}$ straight or branched alkyl, or halogen;

Y is oxygen or sulfur;

Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

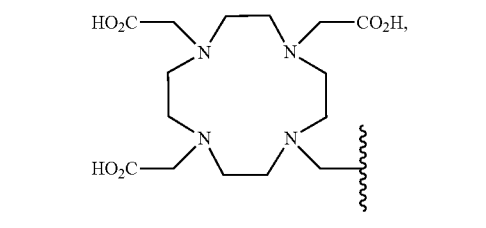

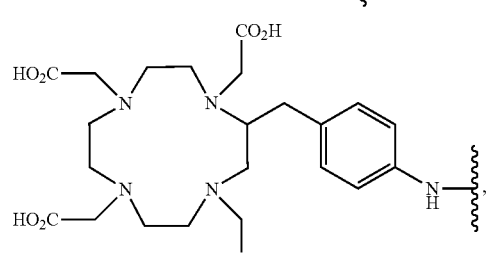

-continued

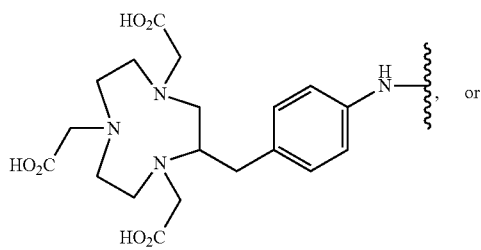

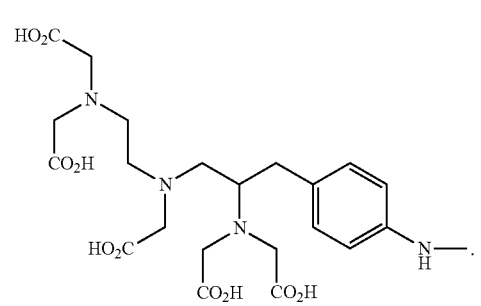

In another aspect of the present invention, the compound represented by formula 1 can be any one compound selected from the group consisting of the following compounds.

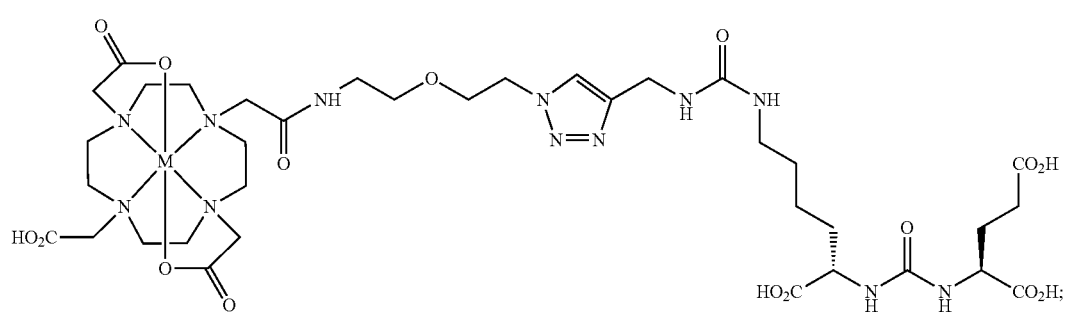
(1)
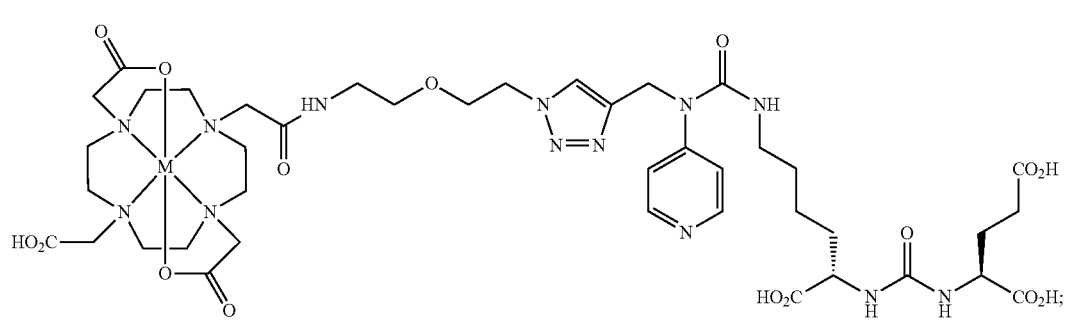
(2)
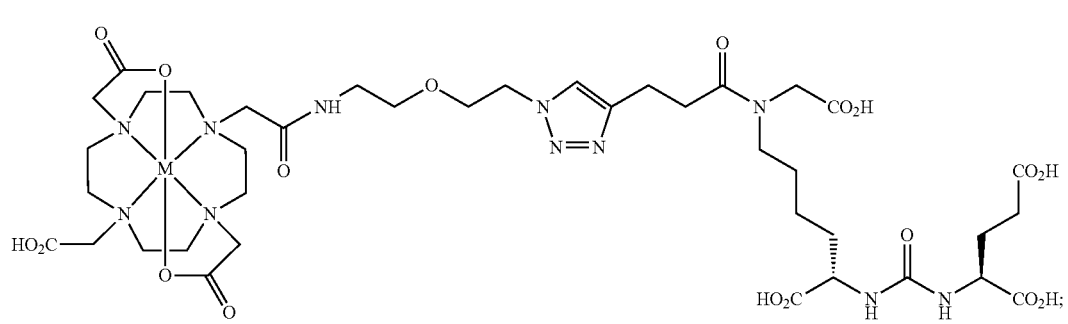
(3)
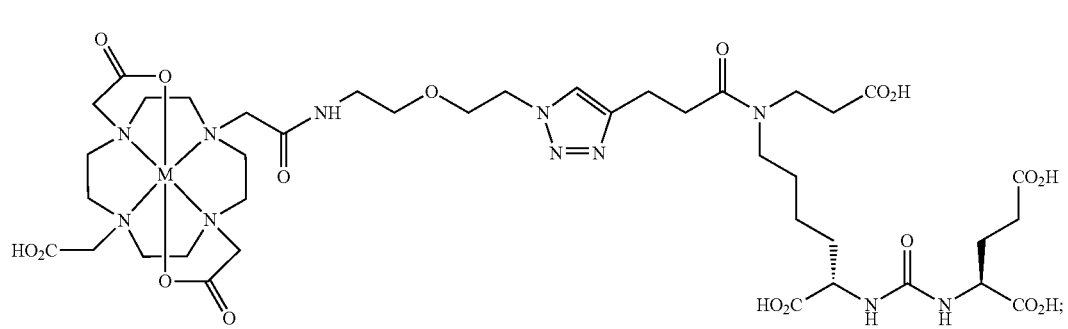
(4)
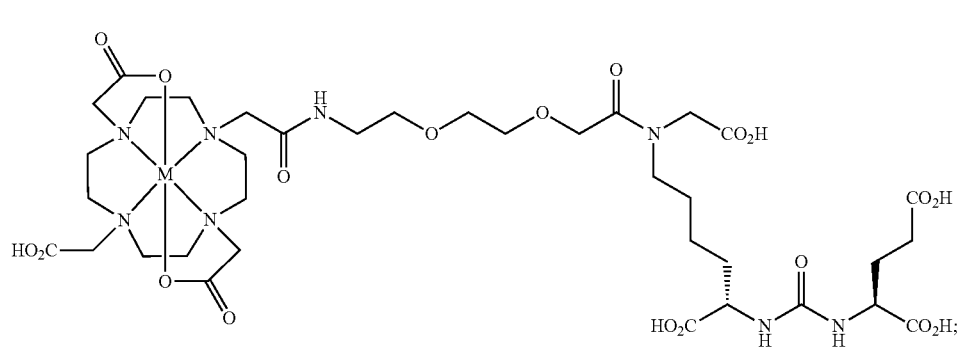
(5)

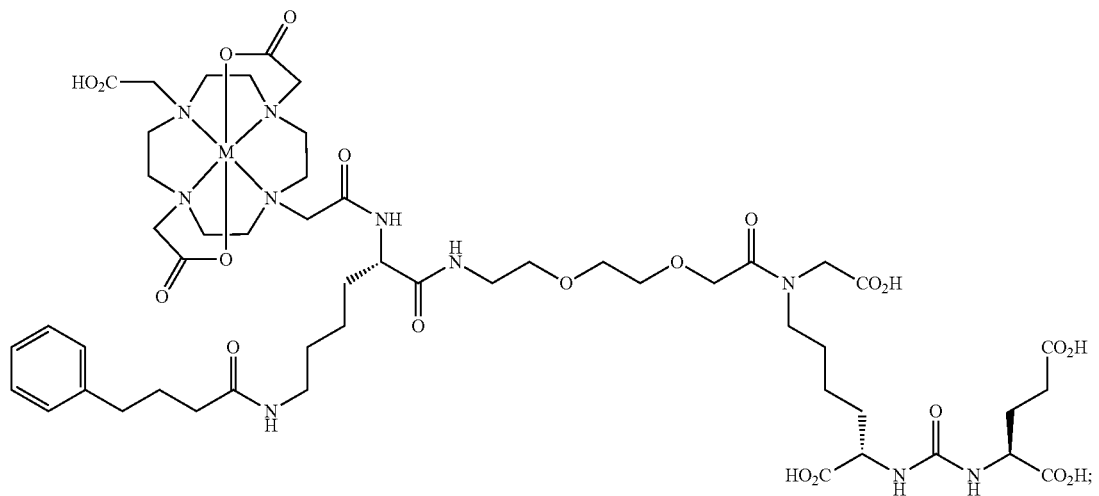
(6)
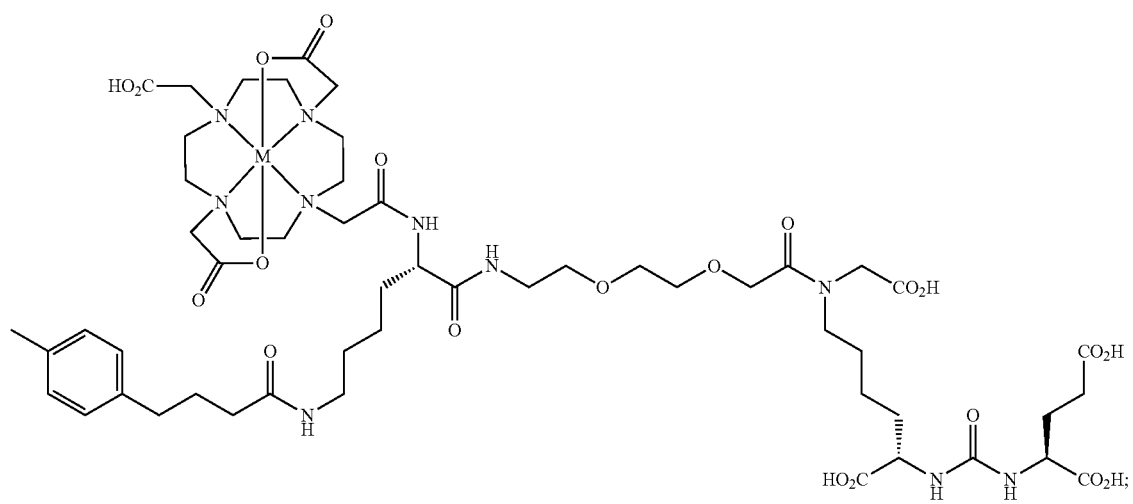
(7)
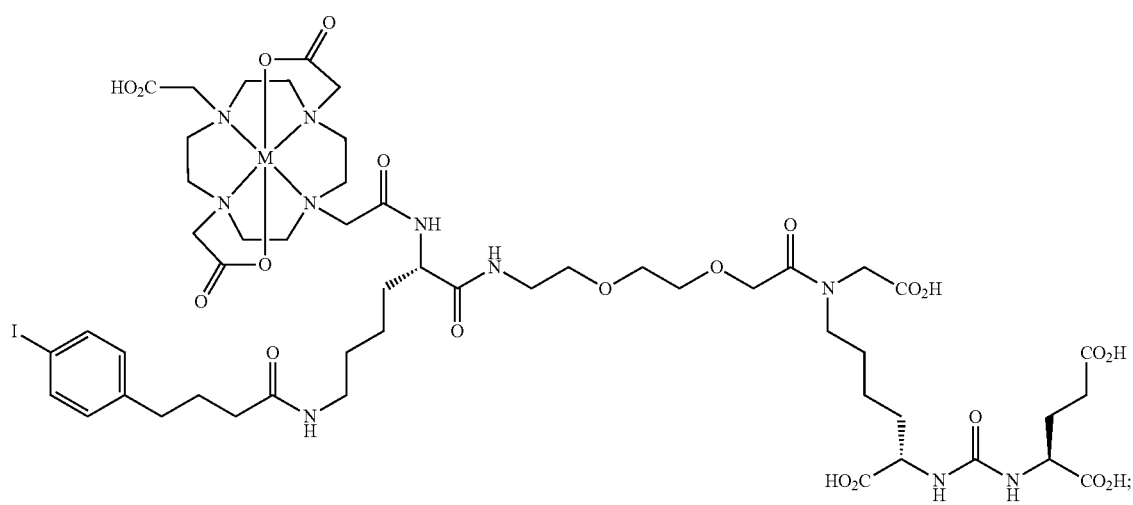
(8)

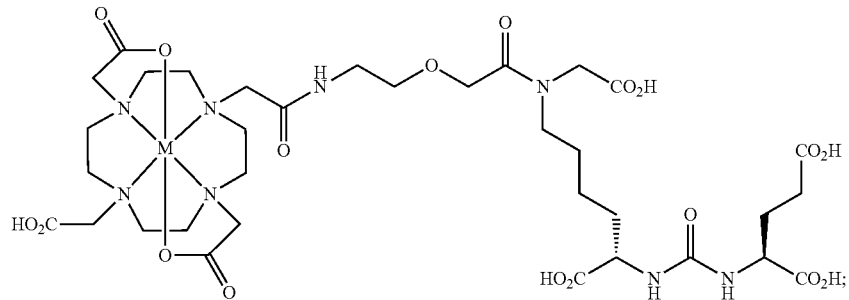
(9)
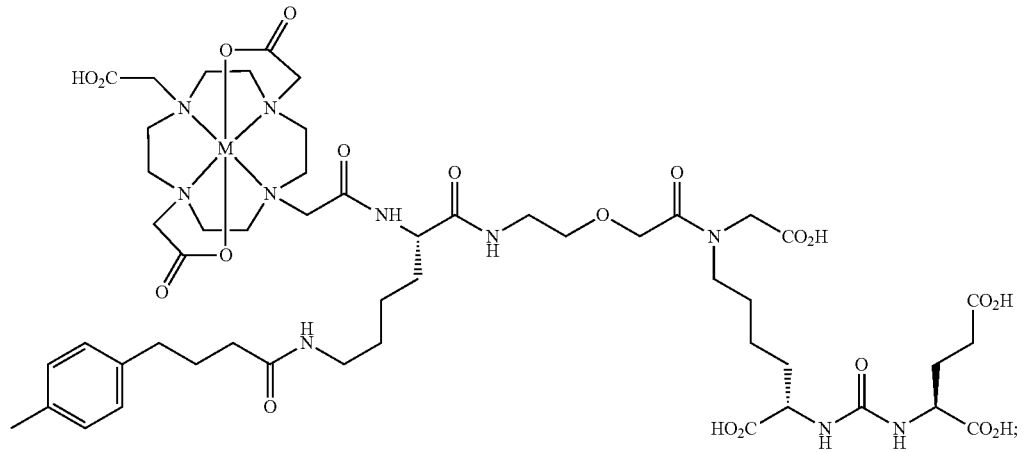
(10)
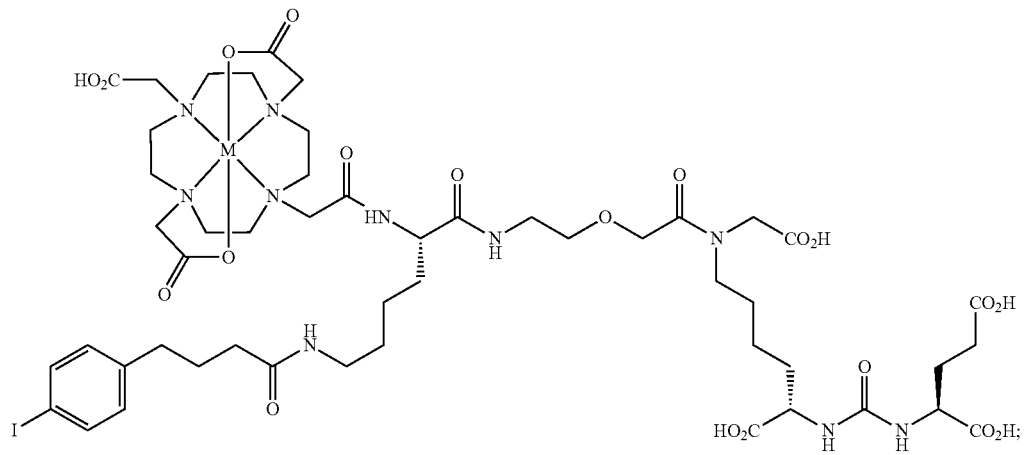
(11)
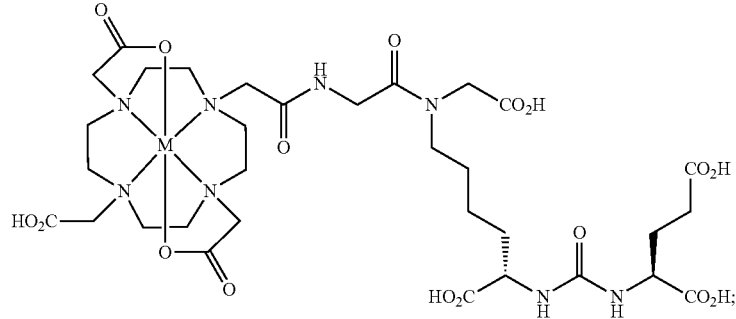
(12)

-continued
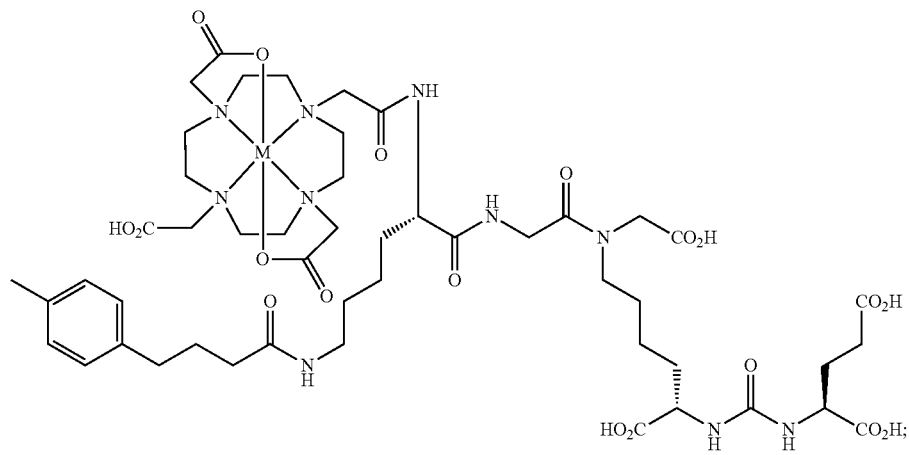
(13)
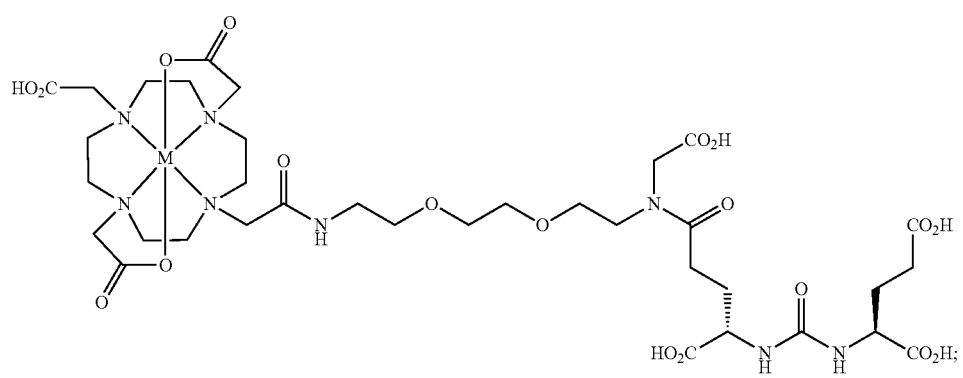
(14)
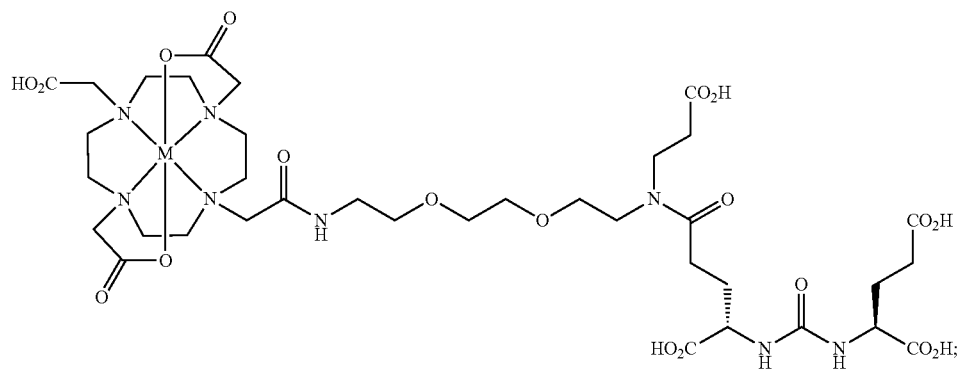
(15)
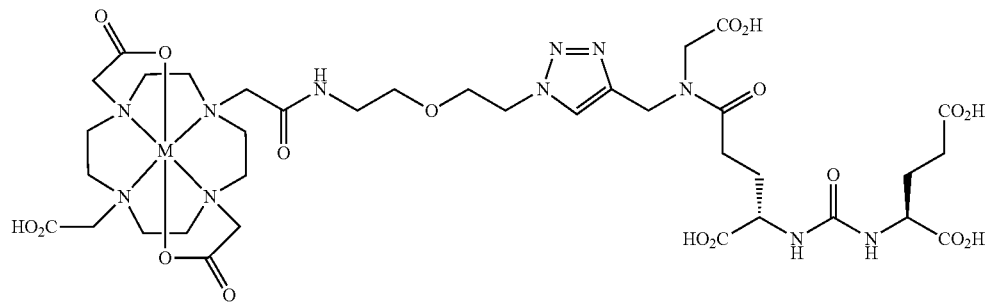
(16)

(At this time, in the above formulas, M is a radioactive metal, and the radioactive metal is as defined in formula 1.).

In another aspect of the present invention, the present invention provides a compound represented by formula 2 below, a stereoisomer thereof, a hydrate thereof, or a pharmaceutically acceptable salt thereof.

[Formula 2]

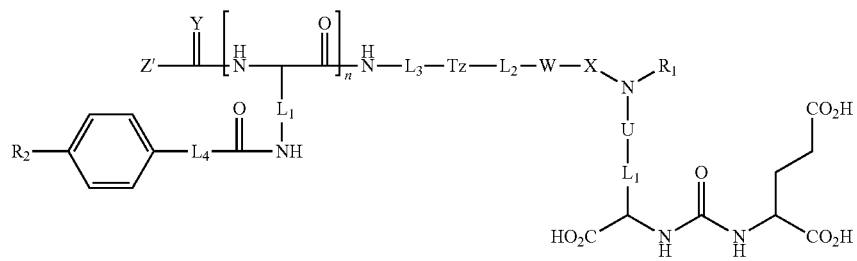

In formula 2,
$L_1$ is —$(CH_2)_a$—, wherein a is an integer of 1~8;
U is a bond, or —C(O)—;
$R_1$ is hydrogen or -$L_5$-$CO_2H$, wherein $L_5$ is —$(CH_2)_b$—, wherein b is an integer of 1~6;
X is a bond, or —C(O)—;
W is a bond or —$NA_1$-, and $A_1$ is hydrogen or —$(CH_2)_c$-pyridyl, wherein c is an integer of 0~3;
$L_2$ is a bond or —$(CH_2)_d$—, wherein d is an integer of 1~8;
Tz is a bond,

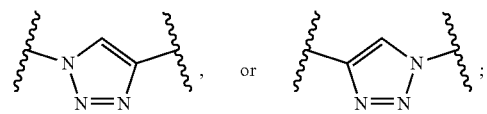 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;
$L_4$ is —$(CH_2)_e$—, wherein e is an integer of 1~6;
n is an integer of 0~1;
$R_2$ is hydrogen, $C_{1-5}$ straight or branched alkyl, or halogen;
Y is oxygen or sulfur;
Z' is a chelator, and the chelator is

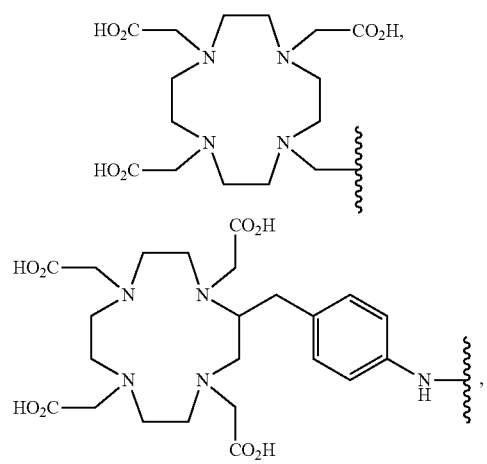

-continued

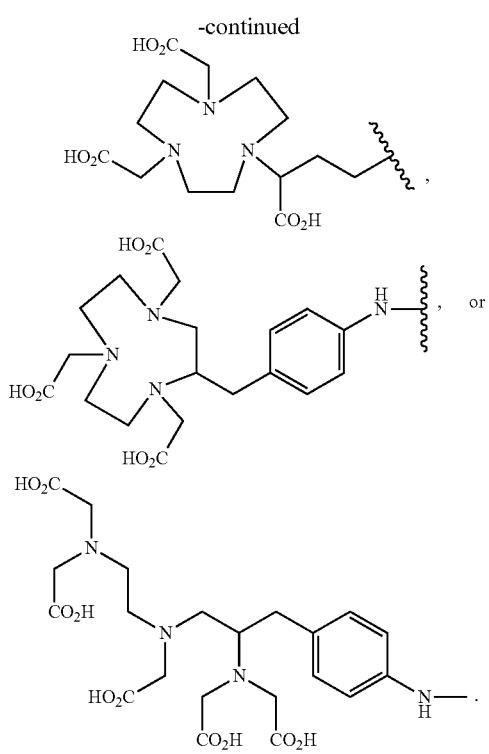

In another aspect of the present invention,
$L_1$ is —$(CH_2)_a$—, wherein a is an integer of 1~6;
U is a bond, or —C(O)—;
$R_1$ is hydrogen or -$L_5$-$CO_2H$, wherein $L_5$ is —$(CH_2)_b$—, wherein b is an integer of 1~4;
X is a bond, or —C(O)—;
W is a bond or —$NA_1$-, and $A_1$ is hydrogen or —$(CH_2)_c$-pyridyl, wherein c is an integer of 0~1;
$L_2$ is a bond or —$(CH_2)_d$—, wherein d is an integer of 1~6;
Tz is a bond,

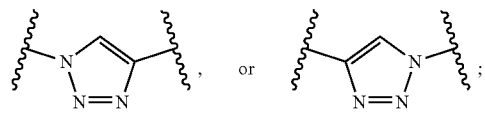 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;

$L_4$ is —$(CH_2)_e$—, wherein e is an integer of 2~4;

n is an integer of 0~1;

$R_2$ is hydrogen, $C_{1-3}$ straight or branched alkyl, or halogen;

Y is oxygen or sulfur;

Z' is a chelator, and the chelator can be

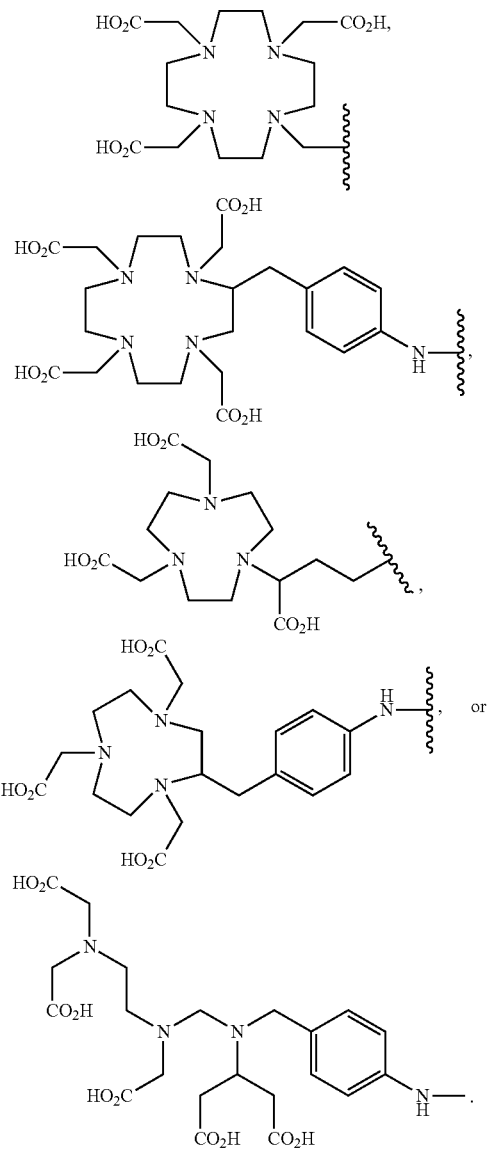

In another aspect of the present invention, $L_1$ is —$(CH_2)_a$—, wherein a is an integer of 2~4;

U is a bond, or —C(O)—;

$R_1$ is hydrogen or -$L_5$-$CO_2H$, wherein $L_5$ is —$(CH_2)_b$—, wherein b is an integer of 1~2;

X is a bond, or —C(O)—;

W is a bond or —$NA_1$-, and $A_1$ is hydrogen or pyridyl;

$L_2$ is a bond or —$(CH_2)_d$—, wherein d is an integer of 1~2;

Tz is

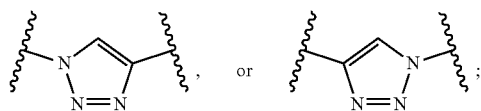 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;

$L_4$ is —$(CH_2)_3$—;

n is an integer of 0~1;

$R_2$ is hydrogen, methyl, or halogen;

Y is oxygen;

Z' is a chelator, and the chelator can be

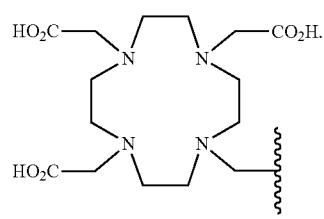

In another aspect of the present invention, the compound represented by formula 2 can be a compound represented by formula 2-1 below.

[Formula 2-1]

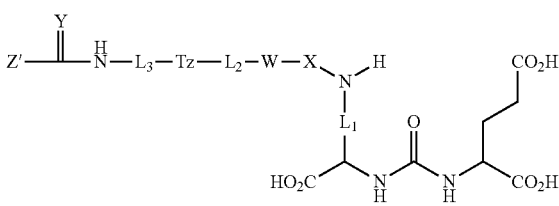

In formula 2-1, $L_1$ is —$(CH_2)_a$—, wherein a is an integer of 1~8;

X is a bond, or —C(O)—;

W is a bond or —$NA_1$-, and $A_1$ is hydrogen or —$(CH_2)_c$-pyridyl, wherein c is an integer of 0~3;

$L_2$ is a bond or —$(CH_2)_d$—, wherein d is an integer of 1~8;

Tz is a bond,

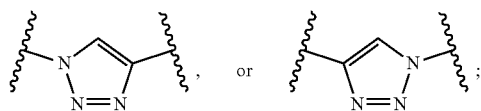 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;

Y is oxygen or sulfur;
Z' is a chelator, and the chelator is

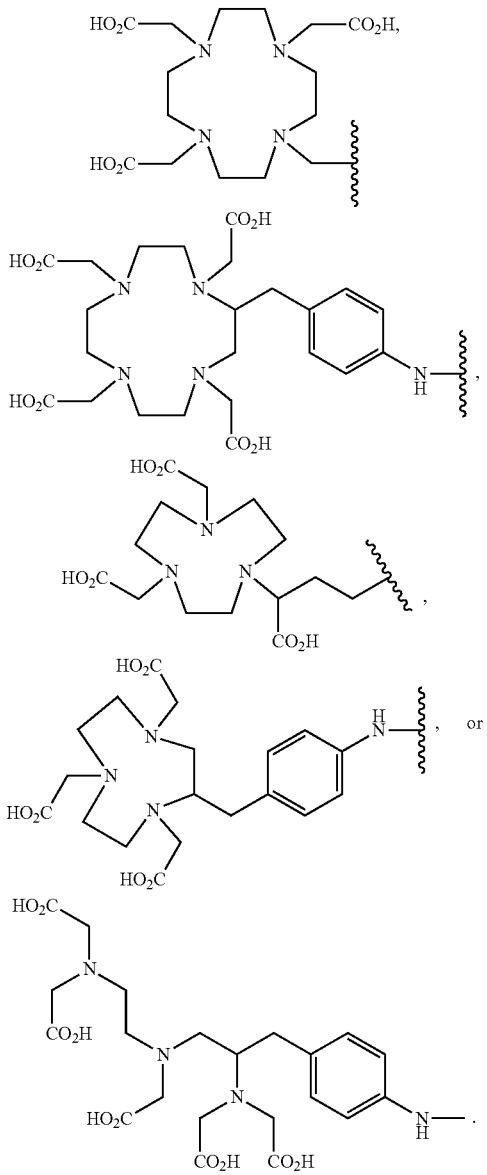

In another aspect of the present invention, the compound represented by formula 2 can be a compound represented by formula 2-2 below.

In formula 2-2, $L_1$ is $-(CH_2)_a-$, wherein a is an integer of 1~8;

U is a bond, or $-C(O)-$;

X is a bond, or $-C(O)-$;

$L_2$ is a bond or $-(CH_2)_d-$, wherein d is an integer of 1~8;

Tz is a bond,

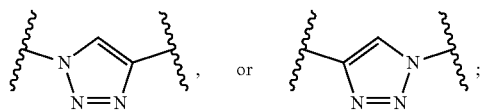 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;

$L_4$ is $-(CH_2)_e-$, wherein e is an integer of 1~6;

n is an integer of 0~1;

$R_2$ is hydrogen, $C_{1-5}$ straight or branched alkyl, or halogen;

Y is oxygen or sulfur;

Z' is a chelator, and the chelator is

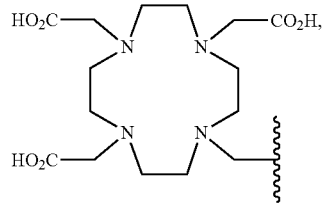 [SMILES: *CN1CCN(CC(=O)O)CCN(CC(=O)O)CCN(CC(=O)O)CC1]

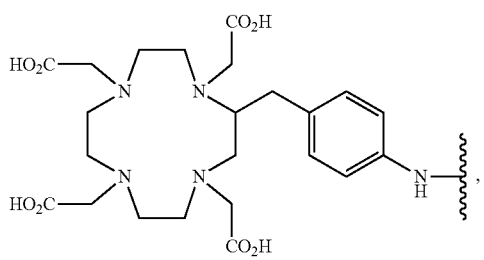

[Formula 2-2]

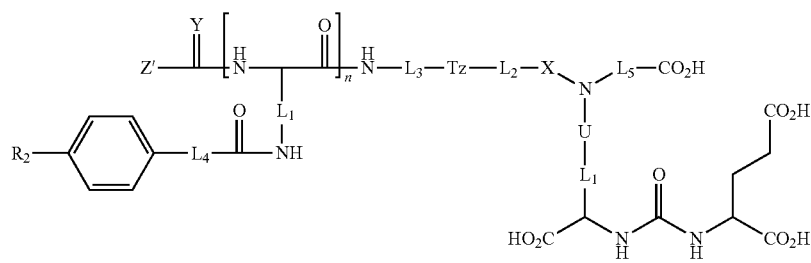

29
-continued
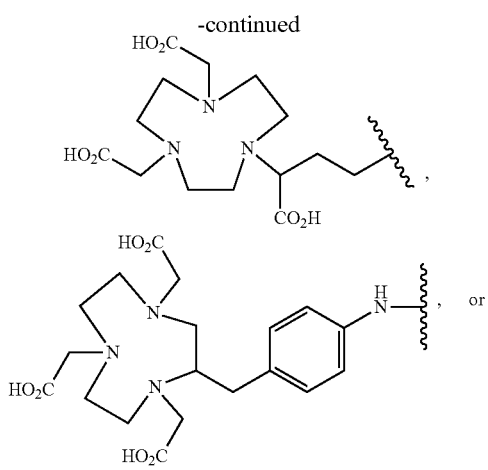
30
-continued
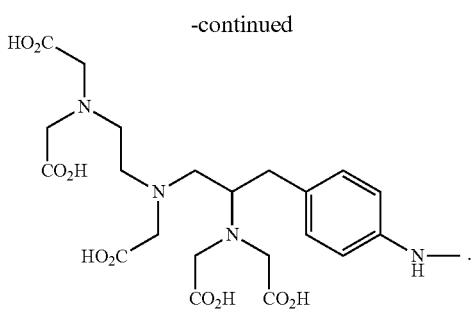
In another aspect of the present invention, the compound represented by formula 2 can be any one compound selected from the group consisting of the following compounds.
(1)
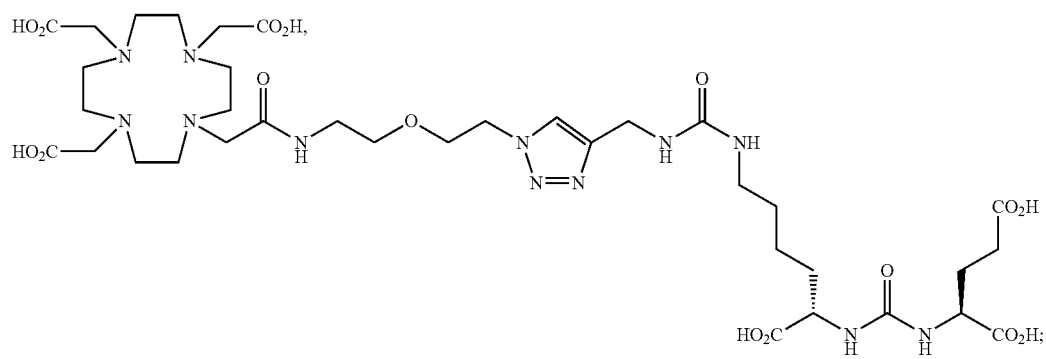
(2)
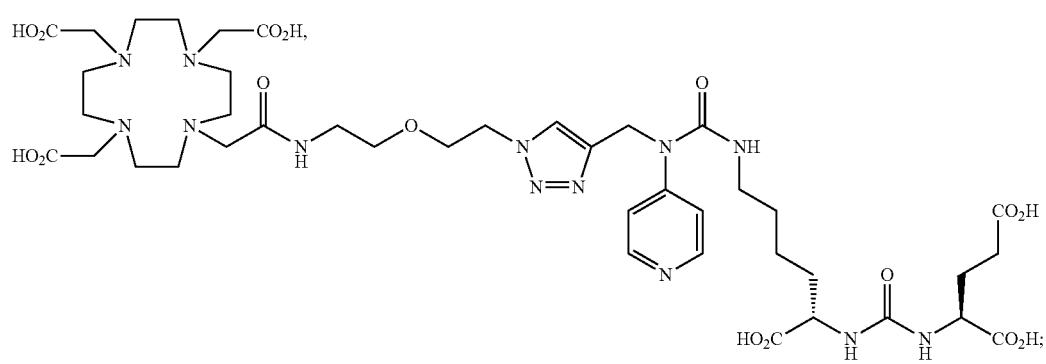
(3)
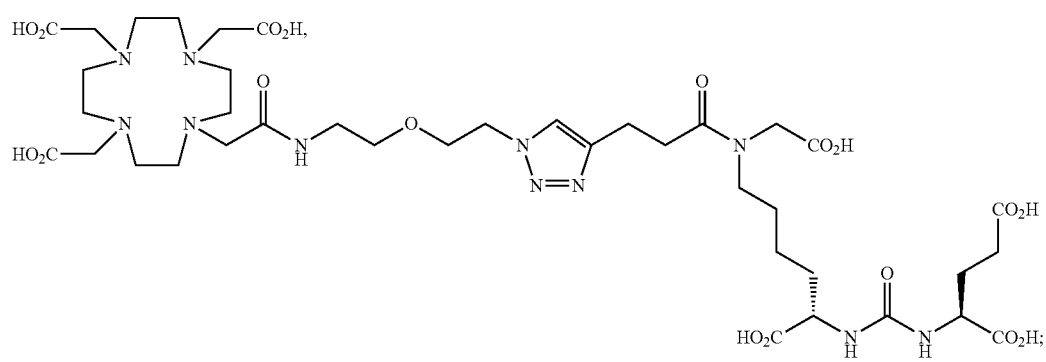

(4)
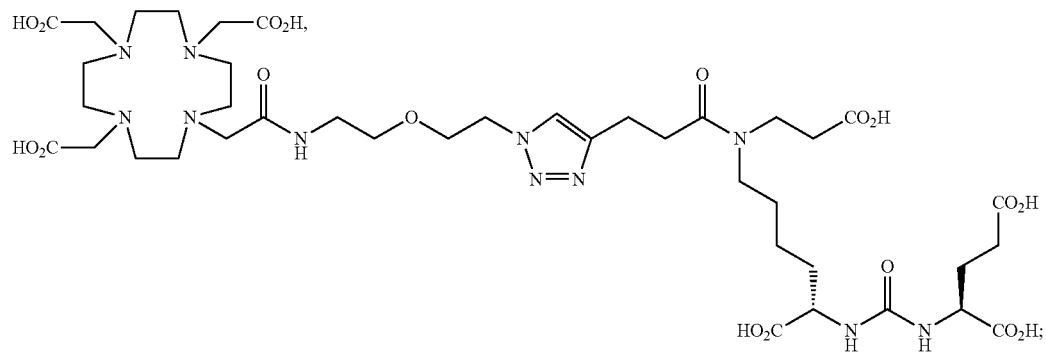
(5)
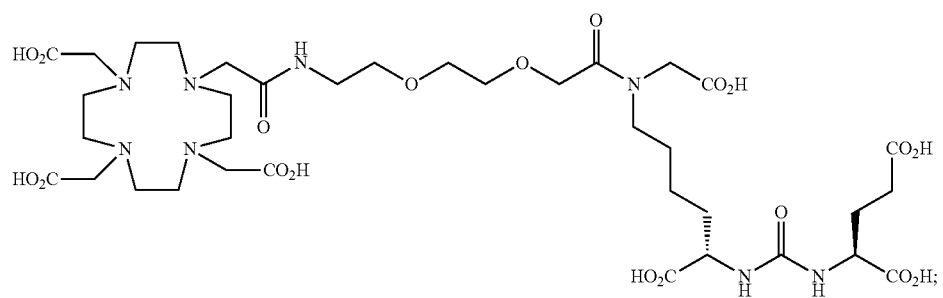
(6)
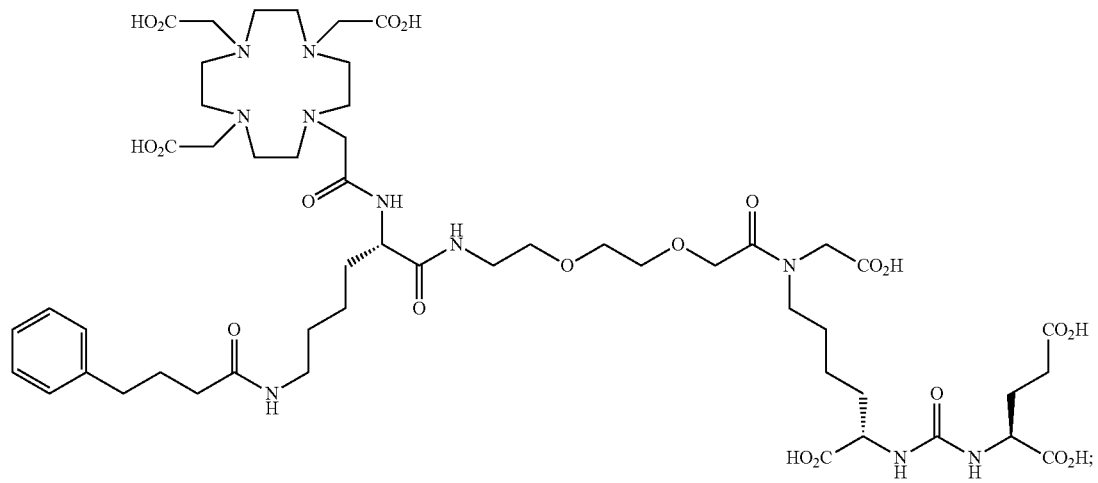
(7)
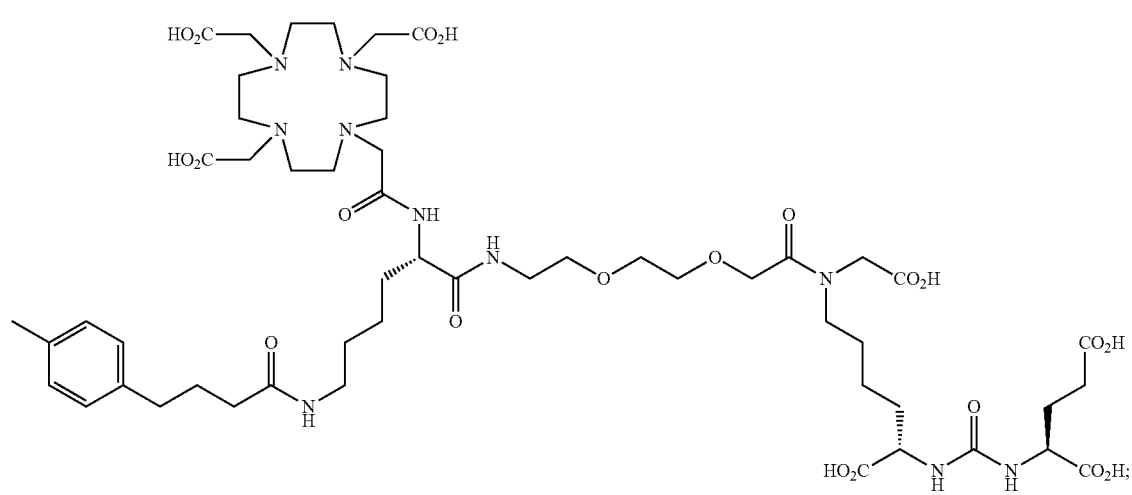

(8)
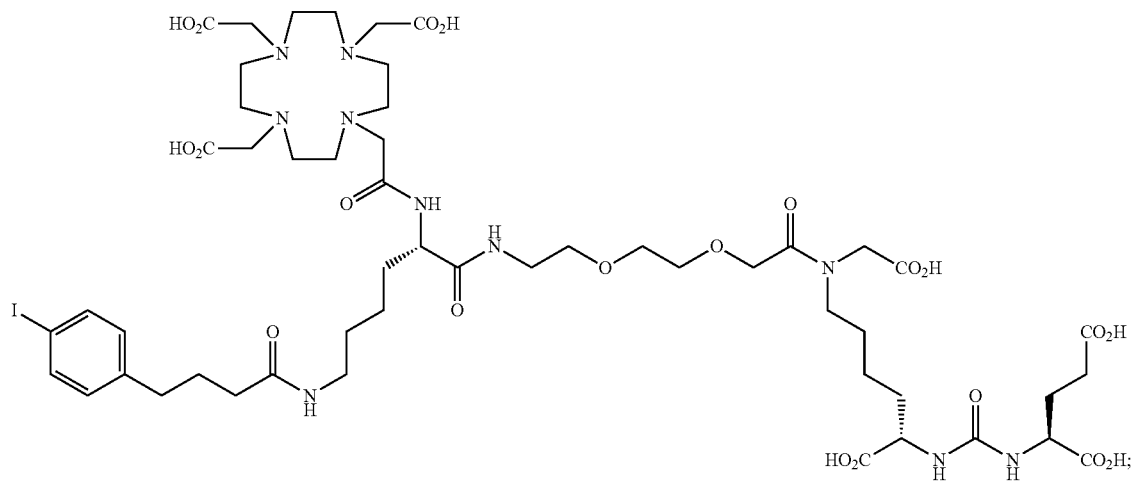
(9)
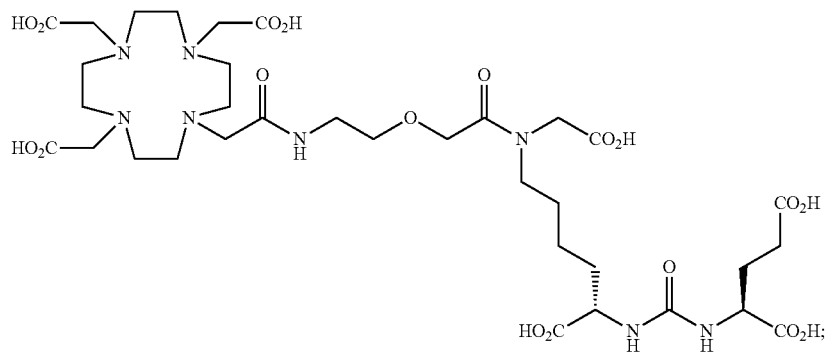
(10)
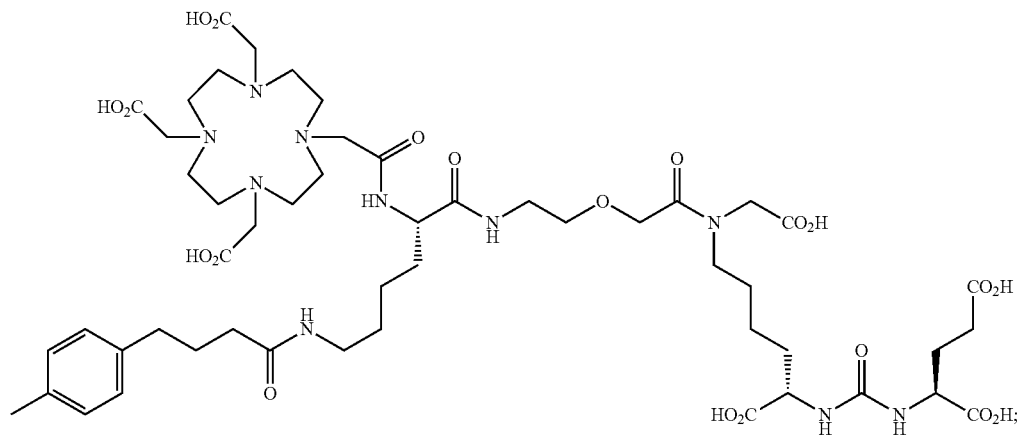

-continued
(11)
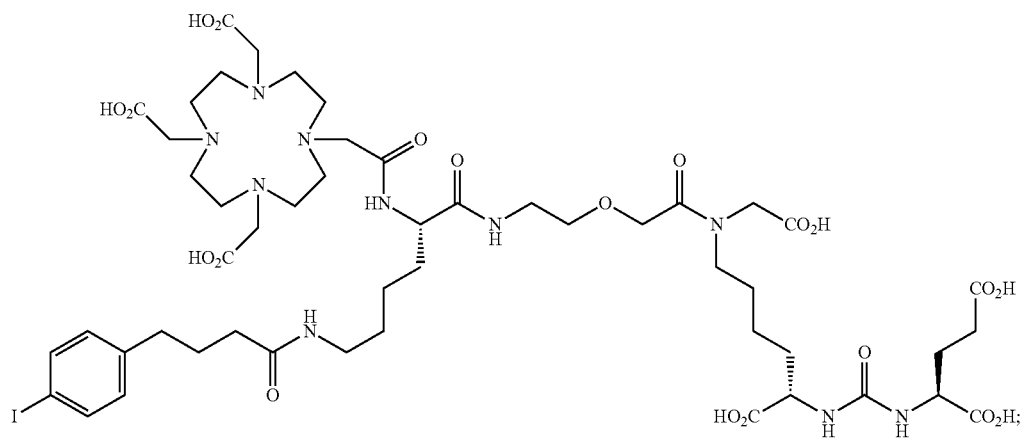
(12)
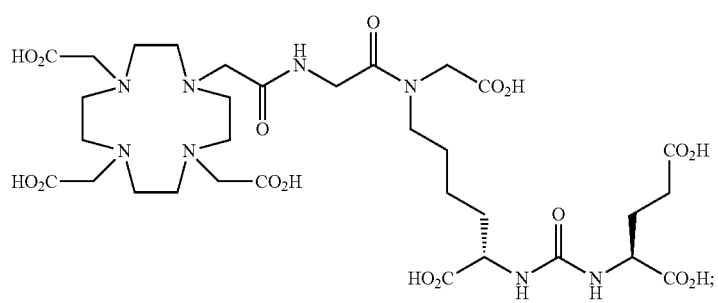
(13)
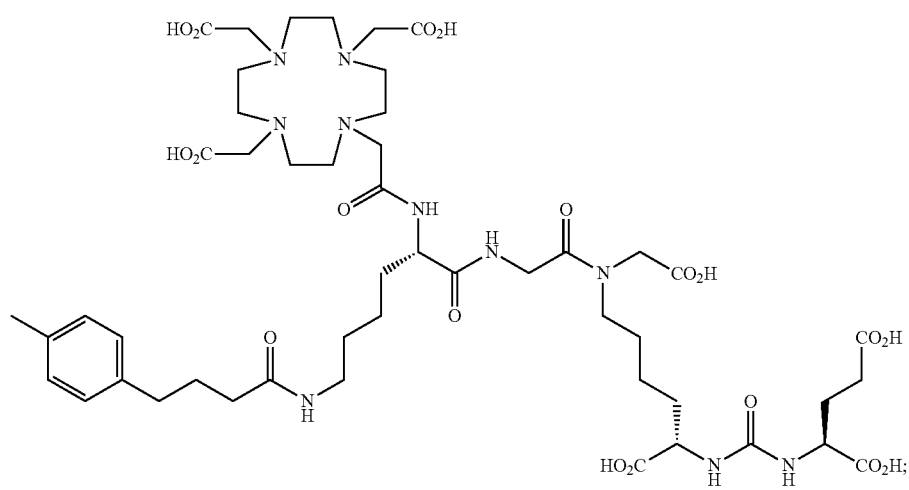
(14)
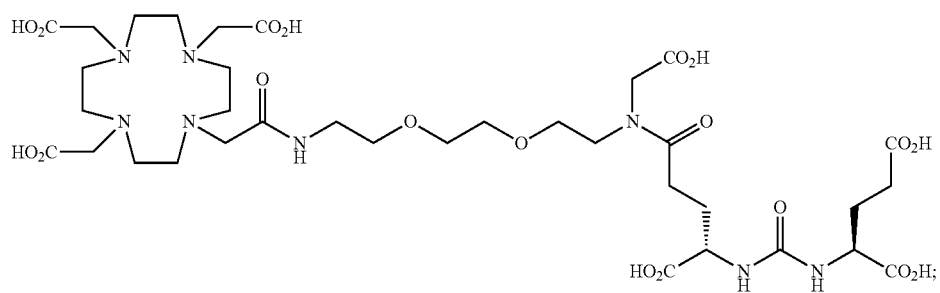

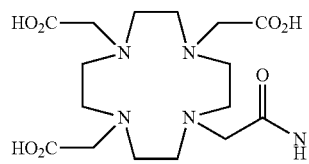
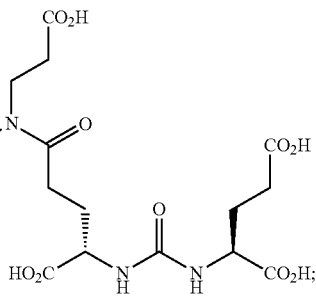

(15)

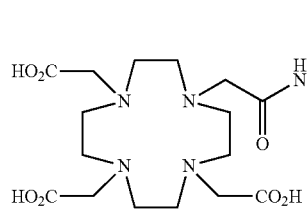
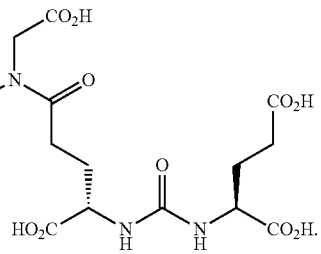

(16)

The compound represented by formula 1 or formula 2 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 or formula 2 is dissolved in an organic solvent such as methanol, ethanol, acetone, methylenechloride, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 or formula 2 but also a pharmaceutically acceptable salt thereof, and a solvate, an optical isomer, or a hydrate possibly produced from the same.

In another aspect of the present invention, the present invention provides a composition for diagnosing prostate cancer comprising the compound represented by formula 1, the stereoisomer thereof, the hydrate thereof, or the pharmaceutically acceptable salt thereof as an active ingredient.

The composition for diagnosing prostate cancer can diagnose prostate cancer by selectively binding the compound to PSMA (Prostate-Specific Membrane Antigen) over-expressed in prostate cancer cells.

In another aspect of the present invention, the present invention provides a pharmaceutical composition for preventing or treating prostate cancer comprising the compound represented by formula 1, the stereoisomer thereof, the hydrate thereof, or the pharmaceutically acceptable salt thereof as an active ingredient.

The compound represented by formula 1 and the pharmaceutically acceptable salt thereof can be administered orally or parenterally and be used in general forms of pharmaceutical formulation. That is, the compound represented by formula 1 and the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions and emulsions. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient of the present invention can be administered by parenterally and the parenteral administration includes subcutaneous injection, intravenous injection, intramuscular injection or intrathoracic injection.

To prepare the composition as a formulation for parenteral administration, the compound represented by formula 1 or the pharmaceutically acceptable salt thereof of the present invention is mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

Hereinafter, the present invention will be described in detail by the following examples.

However, the following examples are only for illustrating the present invention, and the contents of the present invention are not limited thereto.

<Example 1> Preparation of Compounds 3b and 3c

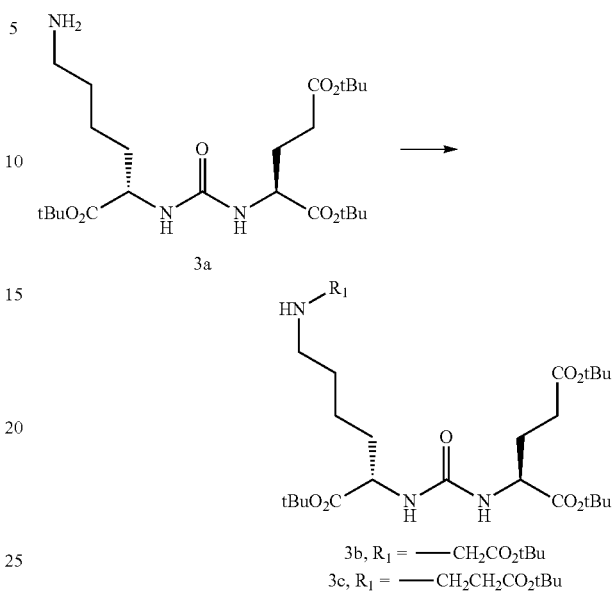

Preparation of Compound 3b

The compound 3a (5.2 g, 10.66 mmol) was dissolved in dichloromethane (100 mL) and cooled to 0° C., to which tert-butyl bromoacetate (1.9 mL, 12.8 mmol) was slowly added. The mixture was maintained at 0° C., to which triethylamine (2.2 mL, 16 mmol) was slowly added, and the mixture was stirred while gradually raising the temperature to room temperature. After stirring the mixture for 3 hours, water (50 mL) was added thereto, and the organic compound was extracted with dichloromethane (50 mL, twice). The collected organic layer was treated with anhydrous sodium sulfate, concentrated under reduced pressure and purified by column chromatography (5% methanol/dichloromethane) to give the compound 3b (3.36 g, 52%).

$^1$H NMR (400 MHz, CDCl$_3$) δ 1.39-1.53 (m, 36H), 1.55-1.89 (m, 5H), 2.02-2.10 (m, 1H), 2.22-2.37 (m, 2H), 2.54-2.58 (m, 2H), 3.27 (s, 2H), 4.28-4.36 (m, 2H), 5.07-5.10 (m, 2H);

$^{13}$C NMR (100 MHz, CDCl$_3$) δ 22.6, 27.9, 28.0, 28.1, 28.2, 28.5, 29.6, 31.6, 32.8, 49.0, 51.7, 53.0, 53.5, 80.5, 81.1, 81.6, 82.0, 156.8, 171.9, 172.1, 172.4, 172.5;

MS (ESI) m/z 602 [M+H]$^+$

Preparation of Compound 3c

The compound 3a (500 mg, 1.03 mmol) was dissolved in ethanol (10 mL), followed by stirring at 0° C. for 10 minutes. Tert-butyl acrylate (0.38 mL, 2.58 mmol) was slowly added thereto, followed by stirring at 0° C. for hours. Upon completion of the reaction, the solvent was removed, and the concentrate was separated by column chromatography (8% methanol/dichloromethane) to give the compound 3c (0.23 g, 37%).

$^1$H NMR (400 MHz, CDCl$_3$) δ 1.40 (s, 9H), 1.41 (s, 9H), 1.43 (s, 18H), 1.48-1.65 (m, 3H), 1.70-1.86 (m, 2H), 2.00-2.07 (m, 1H), 2.21-2.36 (m, 2H), 2.48 (t, J=6.6 Hz, 2H), 2.58-2.69 (m, 2H), 2.86 (t, J=6.6 Hz, 2H), 4.26-4.34 (m, 2H), 5.26 (dd, J=13.0, 8.2 Hz, 2H);

MS (ESI) m/z 616 [M+H]$^+$

<Example 2> Preparation of Compounds 2a and 2b
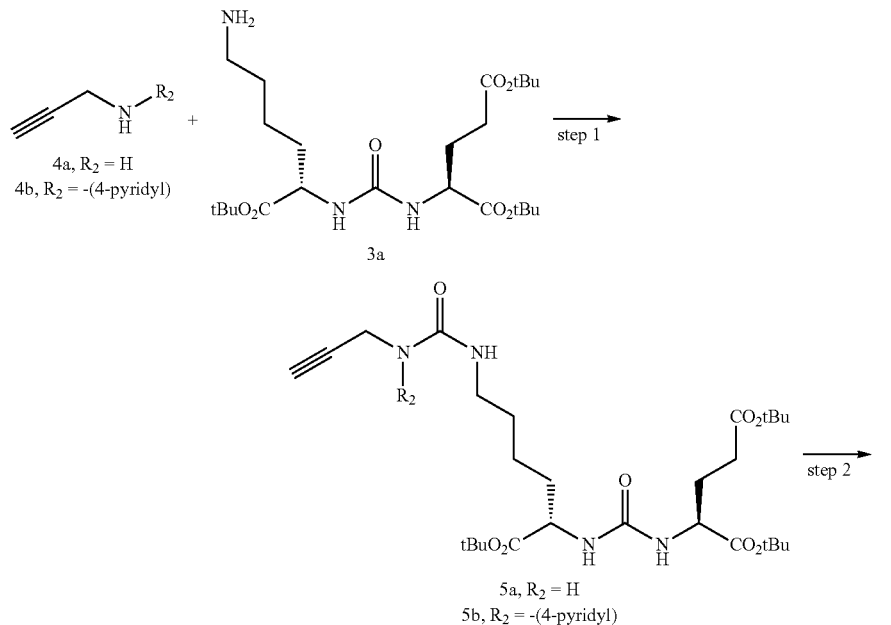
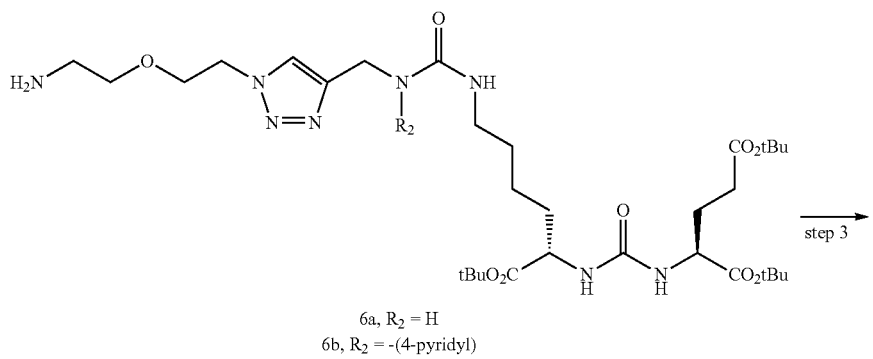
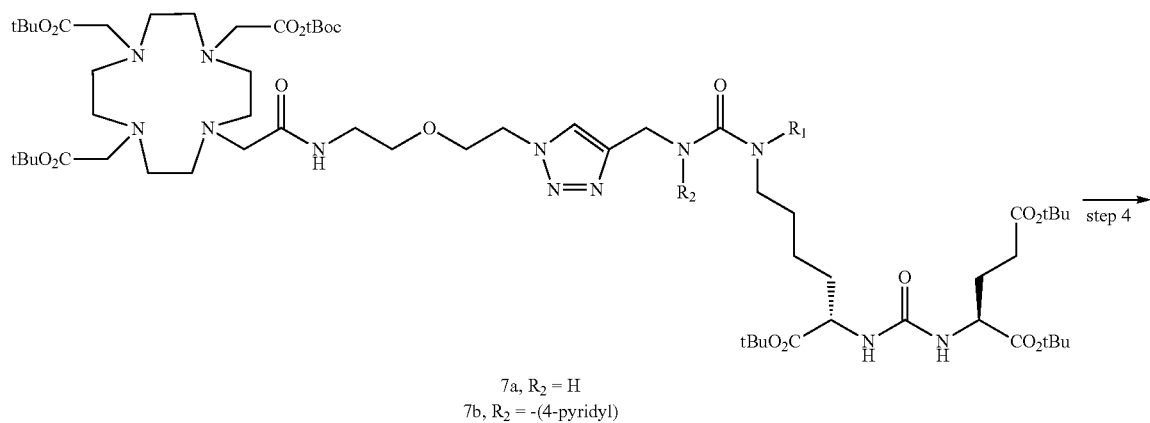

-continued

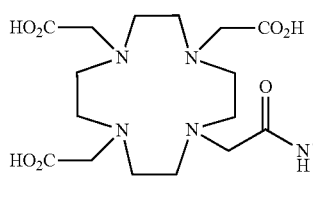
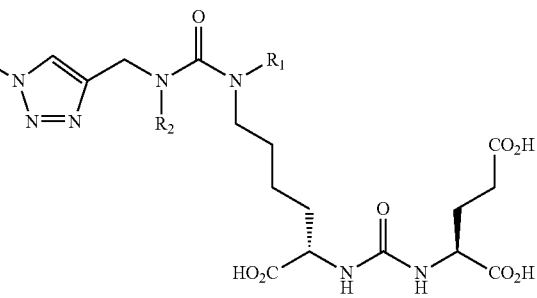

2a, R₂ = H
2b, R₂ = -(4-pyridyl)

Step 1: Preparation of compound 5a Triphosgene (107 mg, 0.36 mmol) was dissolved in acetonitrile (5.0 mL), to which the compound 3a (500 mg, 1.03 mmol) dissolved in acetonitrile was slowly added at 0° C. Then, triethylamine (0.50 mL, 3.61 mmol) was added thereto, followed by stirring for 30 minutes. Propagylamine (4a, 0.072 mL, 1.13 mmol) was added thereto at 0° C. After 15 minutes, the mixture was stirred at room temperature for 1 hour, concentrated under reduced pressure, and then water was added thereto. The organic compound was repeatedly extracted 3 times using ethyl acetate. The collected organic solvent was dried over anhydrous sodium sulfate, concentrated under reduced pressure and separated by column chromatography (2% methanol/dichloromethane) to give the compound 5a (492 mg, 84%) as a white solid.

$^1$H NMR (400 MHz, CDCl$_3$) δ 1.25-1.30 (m, 2H), 1.44 (s, 18H), 1.48 (s, 9H), 1.51-1.60 (m, 3H), 1.67-1.76 (m, 1H), 1.80-1.90 (m, 1H), 2.05-2.13 (m, 1H), 2.18 (t, J=2.6 Hz, 1H), 2.29-2.40 (m, 2H), 3.06-3.12 (m, 1H), 3.30-3.36 (m, 1H), 3.95-4.06 (m, 2H), 4.08-4.14 (m, 1H), 4.36 (sext, J=4.4 Hz, 1H), 5.64 (d, J=7.6 Hz, 1H), 5.69 (t, J=5.2 Hz, 1H), 5.89 (t, J=5.4 Hz, 1H), 6.11 (d, J=8.4 Hz, 1H);

$^{13}$C NMR (100 MHz, CDCl$_3$) δ 23.4, 27.7, 27.8, 27.9, 28.0, 29.6, 29.7, 31.7, 32.1, 39.4, 53.3, 54.2, 70.5, 80.7, 81.4, 81.5, 83.1, 158.0, 158.2, 172.0, 172.3, 174.6;

MS (ESI) m/z 569 [M+H]$^+$

Step 1: Preparation of Compound 5b

The compound 4b (200 mg, 1.51 mmol) was dissolved in acetonitrile (5.0 mL), to which 4-nitrophenyl chloroformate (305 mg, 1.51 mmol) was slowly added at 0° C. Triethylamine (0.50 mL, 3.61 mmol) was added thereto, followed by stirring for 30 minutes. The compound 3a (886 mg, 1.82 mmol) dissolved in acetonitrile (10 mL) was slowly added thereto at 0° C., to which diisopropylethylamine (0.324 mL, 1.82 mmol) was added. After 15 minutes, the mixture was stirred at 100° C. for 12 hours. After cooling the mixture to room temperature, water was added thereto. The organic compound was repeatedly extracted 3 times using ethyl acetate. The collected organic solvent was dried over anhydrous sodium sulfate, concentrated under reduced pressure and separated by column chromatography (5% methanol/dichloromethane) to give the compound 5b (836 mg, 86%) as a colorless liquid.

$^1$H NMR (400 MHz, CDCl$_3$) δ 1.27-1.37 (m, 2H), 1.43 (s, 9H), 1.45 (s, 18H), 1.50-1.55 (m, 2H), 1.59-1.65 (m, 1H), 1.72-1.88 (m, 2H), 2.01-2.10 (m, 1H), 2.27-2.34 (m, 1H), 2.35 (t, J=2.4 Hz, 1H), 2.16 (q, J=6.7 Hz, 2H), 4.25-4.34 (m, 2H), 4.50 (ddd, J=25.2, 18.0, 2.4 Hz, 2H), 5.21 (t, J=5.8 Hz, 1H), 5.48 (s, 1H), 5.50 (s, 1H), 7.32 (dd, J=4.8, 1.6 Hz, 2H), 8.59 (d, J=6.4 Hz, 2H);

$^{13}$C NMR (100 MHz, CDCl$_3$) δ 22.4, 27.9, 28.0, 28.1, 28.3, 29.4, 31.6, 32.4, 38.2, 40.7, 52.9, 53.3, 72.9, 79.3, 80.5, 81.6, 82.0, 119.5, 149.6, 151.2, 155.3, 157.1, 172.3, 172.4, 172.5;

MS (ESI) m/z 646 [M+H]$^+$

Step 2: Preparation of Compound 6a

The compound 5a (0.8 g, 1.4 mmol) and 2-aminoethyl, 2'-azidoethyl ether (0.37 g, 2.81 mmol) were dissolved in ethanol (20 mL), to which 1 M CuSO$_4$ (0.28 mL, 0.28 mmol) and 2 M sodium ascorbate (0.21 mL, 0.42 mmol) were added, followed by stirring for 1 hour. The reactant was filtered and the solvent was eliminated under reduced pressure. The concentrate was separated by NH silica gel column chromatography (2% methanol/dichloromethane) to give the compound 6a (0.45 g, 46%).

MS (ESI) m/z 699 [M+H]$^+$

Step 2: Preparation of Compound 6b

The compound 6b (450 mg, 42%) was obtained by the same manner as described in the preparation of the compound 6a except that the compound 5b (880 mg, 1.4 mmol), 2-aminoethyl, 2'-azidoethyl ether (0.26 g, 2.00 mmol), 1 M CuSO$_4$ (0.27 mL, 0.27 mmol) and 2 M sodium ascorbate (0.20 mL, 0.41 mmol) were used.

MS (ESI) m/z 776 [M+H]$^+$

Step 3: Preparation of Compound 7a

DOTA-tris(tBu) ester (0.44 g, 0.77 mmol) was dissolved in dichloromethane (15 mL), to which hydroxybenzotriazole (HOBt, 0.13 g, 0.97 mmol), TBTU (0.31 g, 0.97 mmol) and diisopropylethylamine (0.224 mL, 0.13 mmol) were added, followed by stirring at room temperature for 10 minutes. The compound 6a (0.45 g, 0.64 mmol) dissolved in dichloromethane (5 mL) was added thereto, followed by stirring 1 hour. The reaction was terminated by adding water (20 mL), and the organic compound was extracted using dichloromethane (20 mL×2). The organic solvent was concentrated under reduced pressure, and the concentrate was separated by column chromatography (4% methanol/dichloromethane) to give the compound 7a (0.32 g, 40%).

$^1$H NMR (400 MHz, methanol-d$_4$) δ 1.45-1.50 (m, 69H), 1.52-1.74 (m, 4H), 1.74-1.85 (m, 2H), 1.98-2.09 (m, 4H), 2.25-2.38 (m, 6H), 3.09-3.16 (m, 6H), 3.35-3.43 (m, 4H), 3.47-3.56 (m, 4H), 3.61-3.68 (m, 2H), 3.81-3.86 (m, 4H), 4.11-4.15 (m, 2H), 4.18-4.25 (m, 2H), 4.36-4.38 (m, 4H), 4.55 (t, J=4.8 Hz, 4H), 7.84 (s, 0.7H), 7.86 (s, 0.3H);
MS (ESI) m/z 1254 [M+H]+

Step 3: Preparation of Compound 7b

The compound 7b (0.15 g, 29%) was obtained by the same manner as described in the preparation of the compound 7a except that DOTA-tris(tBu) ester (270 mg, 0.46 mmol), hydroxybenzotriazole (HOBt, 0.078 g, 0.58 mmol), TBTU (0.19 g, 0.58 mmol), diisopropylethylamine (0.134 mL, 0.77 mmol), and the compound 6b (0.30 g, 0.39 mmol) were used.

$^1$H NMR (400 MHz, methanol-$d_4$) δ 1.35-1.49 (m, 63H), 1.60-1.68 (m, 1H), 1.73-1.85 (m, 4H), 1.99-2.08 (m, 3H), 2.27-2.34 (m, 4H), 3.20-3.26 (m, 8H), 3.51 (t, J=5.6 Hz, 4H), 3.69-3.78 (m, 5H), 3.81-3.83 (m, 1H), 4.09-4.23 (m, 1H), 4.46-4.56 (m, 4H), 5.03 (s, 4H), 7.41 (d, J=6.8 Hz, 2H), 7.94 (s, 1H), 8.43 (d, J=6.4 Hz, 2H);
MS (ESI) m/z 1331 [M+H]+

Step 4: Preparation of Compound 2a

The compound 7a (300 mg, 0.24 mmol) was added to 70% trifluoroacetic acid/dichloromethane (6 mL), followed by stirring for 5 hours. Diethyl ether (20 mL) was added thereto to precipitate, and it was separated using a centrifuge. The mixture was separated by HPLC and dried using a lyophilizer to give the compound 2a (115 mg, 52%) as a solid.

$^1$H NMR (400 MHz, D$_2$O) δ 1.31-1.44 (m, 2H), 1.45-1.55 (m, 2H), 1.66-1.75 (m, 1H), 1.79-1.88 (m, 1H), 1.93-2.02 (m, 1H), 2.14-2.22 (m, 1H), 2.52 (t, J=7.2 Hz, 2H), 3.11 (t, J=6.8 Hz, 3H), 3.14-3.55 (m, 26H), 3.58 (t, J=5.2 Hz, 3H), 3.62-3.93 (m, 6H), 3.96 (t, J=5.6 Hz, 4H), 4.18 (dd, J=13.6, 4.8 Hz, 1H), 4.27 (dd, J=14.4, 5.2 Hz, 1H), 4.39 (s, 2H), 4.61 (t, J=5.2 Hz, 2H), 7.93 (s, 1H);
MS (ESI) m/z 918 [M+H]+

Step 4: Preparation of Compound 2b

The compound 2b (10 mg, 48%) was obtained by the same manner as described in the preparation of the compound 2a as a solid except that the compound 7a (28 mg, 21 μmol) and 70% trifluoroacetic acid/dichloromethane (0.4 mL) were used.

$^1$H NMR (400 MHz, D$_2$O) δ 1.31-1.44 (m, 4H), 1.51-1.62 (m, 2H), 1.64-1.75 (m, 1H), 1.79-1.87 (m, 1H), 1.90-1.99 (m, 1H), 2.11-2.19 (m, 1H), 2.49 (t, J=7.6 Hz, 2H), 2.90-3.48 (m, 18H), 5.52 (t, J=5.2 Hz, 3H), 3.61-3.88 (m, 6H), 3.92 (t, J=4.8 Hz, 3H), 4.16 (dd, J=14.0, 5.2 Hz, 1H), 4.25 (dd, J=14.4, 5.2 Hz, 1H), 4.59 (t, J=4.4 Hz, 2H), 5.19 (s, 2H), 7.60 (d, J=7.2 Hz, 2H), 8.03 (s, 1H), 8.42 (d, J=7.2 Hz, 2H);
MS (ESI) m/z 995 [M+H]+

<Example 3> Preparation of Compounds 2c and 2d

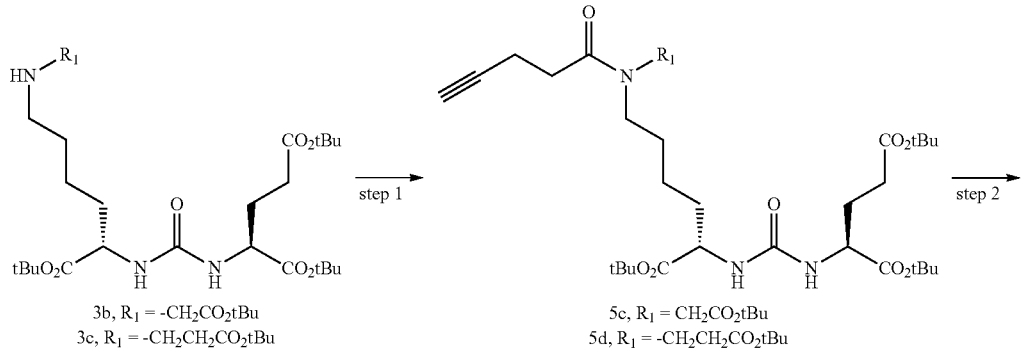

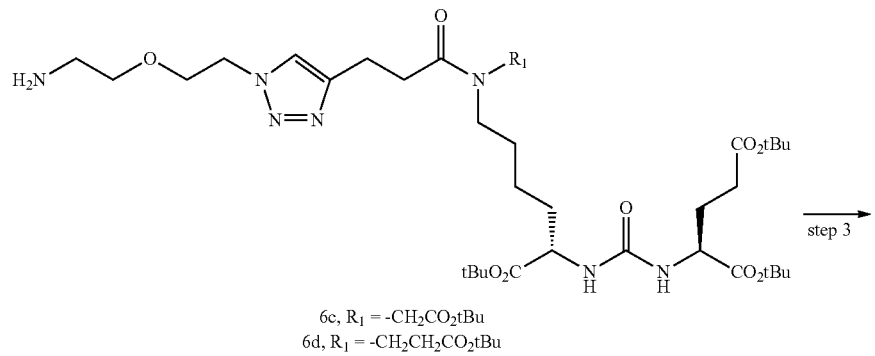

-continued

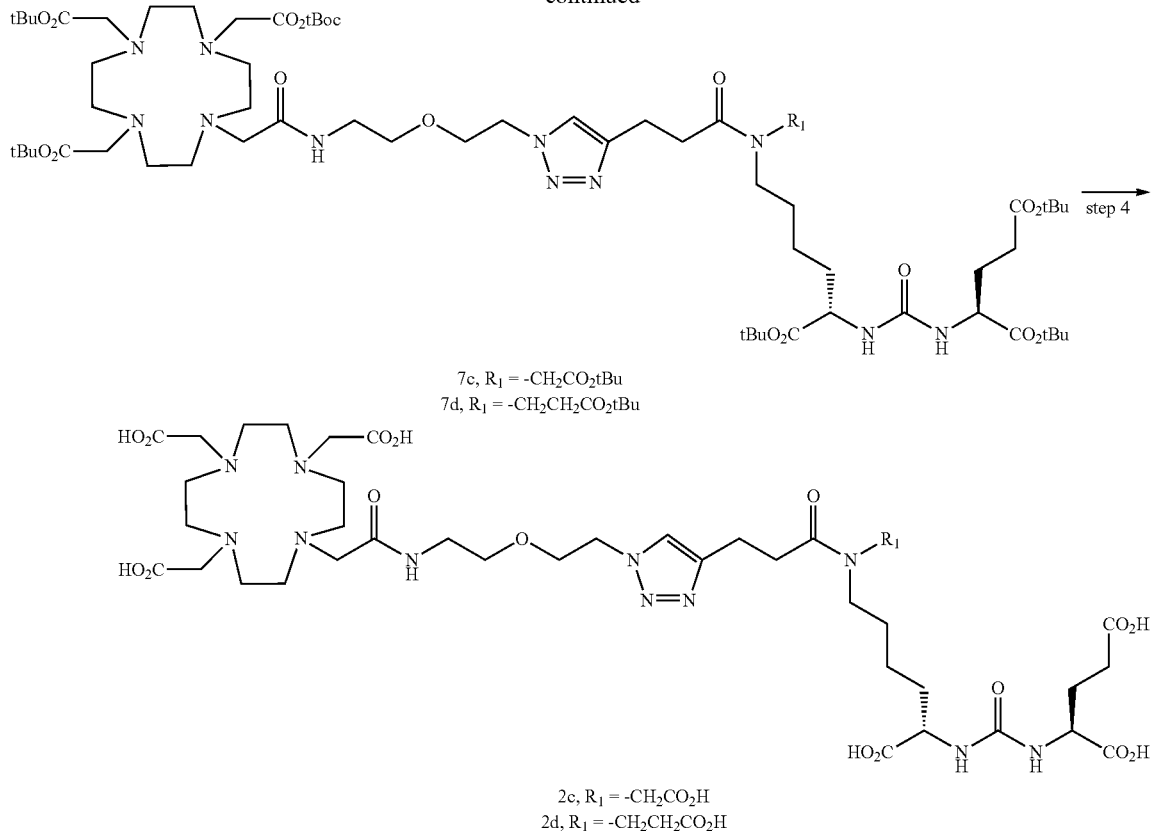

7c, $R_1$ = -CH$_2$CO$_2$tBu
7d, $R_1$ = -CH$_2$CH$_2$CO$_2$tBu

2c, $R_1$ = -CH$_2$CO$_2$H
2d, $R_1$ = -CH$_2$CH$_2$CO$_2$H

Step 1: Preparation of Compound 5c

4-Pentaenoic acid (82 mg, 0.83 mmol) was dissolved in dichloromethane (10 mL) and cooled to 0° C., to which N,N'-dicyclohexylcarbodiimide (190 mg, 0.91 mmol) and the compound 3c (0.5 g, 0.83 mmol) were added, followed by stirring at room temperature for 1 hour. The organic layer was filtered several times and the solvent was eliminated under reduced pressure. The concentrate was separated by column chromatography (30% ethylacetate/n-hexane) to give the compound 5c (0.29 g, 52%).

$^1$H NMR (400 MHz, CDCl$_3$) δ 1.34-1.67 (m, 39H), 1.68-2.02 (m, 5H), 2.16-2.32 (m, 2H), 2.37-2.56 (m, 5H), 3.22 (t, J=7.2 Hz, 1H), 3.29 (t, J=7.6 Hz, 1H), 3.82-3.90 (m, 2H), 4.17-4.29 (m, 2H), 5.49-5.52 (m, 1.5H), 5.60 (d, J=8.0 Hz, 0.5 Hz);

MS (ESI) m/z 704 [M+Na]$^+$

Step 1: Preparation of Compound 5d

The compound 5d (0.18 g, 79%) was obtained by the same manner as described in the preparation of the compound 5c except that 4-pentaenoic acid (32 mg, 0.32 mmol), N,N'-dicyclohexylcarbodiimide (74 mg, 0.36 mmol), and the compound 3c (0.20 g, 0.32 mmol) were used.

$^1$H NMR (400 MHz, CDCl$_3$) δ 1.41-1.43 (m, 27), 1.44 (s, 9H), 1.51-1.63 (m, 3H), 1.76-1.88 (m, 2H), 1.93-1.96 (m, 1H), 2.01-2.08 (m, 1H), 2.20-2.36 (m, 2H), 2.46-2.53 (m, 5H), 2.57-2.60 (m, 1H), 3.26 (dt, J=21.2, 7.7 Hz, 2H), 3.52 (q, J=7.2 Hz, 2H), 4.24-4.35 (m, 2H), 5.05 (dd, J=16.4, 8.0 Hz, 1H), 5.33 (dd, J=61.2, 8.0 Hz, 1H);

MS (ESI) m/z 718 [M+Na]$^+$

Step 2: Preparation of Compound 6c

The compound 5c (0.26 g, 0.38 mmol) and 2-aminoethyl, 2'-azidoethyl ether (60 mg, 0.46 mmol) were dissolved in ethanol (5 mL), to which 1 M CuSO$_4$ (0.076 mL, 0.076 mmol) and 2 M sodium ascorbate (0.057 mL, 0.11 mmol) were added, followed by stirring for 1 hour. The reactant was filtered and the solvent was eliminated under reduced pressure. The concentrate was separated by NH silica gel column chromatography (3% methanol/dichloromethane) to give the compound 6c (0.27 g, 87%).

$^1$H NMR (400 MHz, methanol-d$_4$) δ 1.37-1.55 (m, 36H), 1.56-1.70 (m, 2H), 1.71-1.94 (m, 2H), 1.95-2.14 (m, 2H), 2.24-2.40 (m, 2H), 2.58-2.91 (m, 2H), 2.92-3.12 (m, 2H), 3.33-3.48 (m, 4H), 3.49-3.76 (m, 4H), 3.77-3.92 (m, 2H), 3.96 (s, 1H), 4.45-4.28 (m, 3H), 4.46-4.65 (m, 1H);

MS (ESI) m/z 813 [M+H]$^+$

Step 2: Preparation of Compound 6d

The compound 6d (60.0 mg, 50%) was obtained by the same manner as described in the preparation of the compound 6c except that the compound 5d (0.10 g, 0.14 mmol), 2-aminoethyl, 2'-azidoethyl ether (21 mg, 0.16 mmol), 1 M CuSO$_4$ (0.030 mL, 0.030 mmol) and 2 M sodium ascorbate (0.020 mL, 0.040 mmol) were used.

$^1$H NMR (400 MHz, CDCl$_3$) δ 1.23-1.30 (m, 2H), 1.40 (s, 18H), 1.42 (s, 18H), 1.68 (s, 6H), 1.74-1.87 (m, 2H), 1.99-2.09 (m, 1H), 2.24-2.35 (m, 2H), 2.41-2.47 (m, 2H), 2.70-2.75 (m, 1H), 2.96-3.08 (m, 2H), 3.20-3.31 (m, 2H), 3.28-3.54 (m, 3H), 3.81 (t, J=8.0 Hz, 2H), 4.24-4.42 (m, 2H), 4.47-4.55 (m, 2H), 5.59 (dd, J=53.4, 7.4 Hz, 1H), 5.77 (dd, J=37.6, 8.4 Hz, 1H), 7.53 (d, J=16.4 Hz, 1H);

MS (ESI) m/z 826 (M+H)$^+$

Step 3: Preparation of Compound 7c

DOTA-tris(tBu) ester (84 mg, 0.015 mmol) was dissolved in dichloromethane (5 mL), to which hydroxybenzotriazole (HOBt, 25 mg, 0.019 mmol), TBTU (59 mg, 0.019 mmol)

and diisopropylethylamine (0.042 mL, 0.25 mmol) were added, followed by stirring at room temperature for 10 minutes. The compound 6c (100 mg, 0.12 mmol) dissolved in dichloromethane (2 mL) was added thereto, followed by stirring 1 hour. The reaction was terminated by adding water (10 mL), and the organic compound was extracted using dichloromethane (10 mL×2). The reactant was dried over anhydrous sodium sulfate and concentrated under reduced pressure. The concentrate was separated by column chromatography (3% methanol/dichloromethane) to give the compound 7c (95 mg, 56%).

$^1$H NMR (400 MHz, methanol-$d_4$) δ 1.42-1.65 (m, 63H), 1.71-1.85 (m, 2H), 1.95-3.69 (m, 40H), 3.74 (s, 3H), 3.79-3.92 (m, 2H), 3.96 (s, 1H), 4.11-4.20 (m, 3H), 4.50-4.58 (m, 2H);

MS (ESI) m/z 1388 [M+Na]$^+$

Step 3: Preparation of Compound 7d

The compound 7d (51 mg, 61%) was obtained by the same manner as described in the preparation of the compound 7c except that DOTA-tris(tBu) ester (29 mg, 0.073 mmol) was dissolved in dichloromethane (5 mL) and hydroxybenzotriazole (HOBt, 12 mg, 0.091 mmol), TBTU (29 mg, 0.091 mmol), diisopropylethylamine (15.86 μL, 91.07 μmol) and the compound 6d (50 mg, 60.5 μmol) were used.

$^1$H NMR (400 MHz, CDCl$_3$) δ 0.75-0.94 (m, 2H), 1.23-1.61 (m, 63H), 1.69 (s, 5H), 1.77-1.87 (m, 2H), 2.00-2.08 (m, 3H), 2.21 (bs, 2H), 2.27-2.37 (m, 3H), 2.41-2.48 (m, 4H), 2.78 (s, 4H), 2.94-3.06 (m, 3H), 3.20-3.38 (m, 5H), 3.43-3.56 (m, 4H), 3.60 (t, J=5.2 Hz, 2H), 3.66-3.75 (m, 5H), 3.80 (t, J=4.8 Hz, 2H), 4.19 (d, J=4.0 Hz, 2H), 4.25-4.34 (m, 2H), 4.50-4.54 (m, 2H), 5.47 (dd, J=26.8, 8.0 Hz, 1H), 5.66 (dd, J=12.4, 8.4 Hz, 1H), 7.71 (d, J=41.2 Hz, 1H)

MS (ESI) m/z 1381 [M+H]$^+$

Step 4: Preparation of Compound 2c

The compound 7c (60 mg, 0.044 mmol) was added to 70% trifluoroacetic acid/dichloromethane (2 mL), followed by stirring for 4 hours. Diethyl ether (20 mL) was added thereto to precipitate, and it was separated using a centrifuge. The mixture was separated by HPLC and dried using a lyophilizer to give the compound 2c (25 mg, 58%) as a solid.

$^1$H NMR (400 MHz, D$_2$O) δ 1.10-1.30 (m, 2H), 1.31-1.50 (m, 2H), 1.52-1.63 (m, 1H), 1.64-1.76 (m, 1H), 1.78-1.89 (m, 1H), 1.99-2.09 (m, 1H), 2.36-2.40 (m, 2H), 2.62-2.65 (m, 1H), 2.77-2.80 (m, 2H), 2.95-2.98 (m, 3H), 3.00-3.19 (m, 7H), 3.21-3.42 (m, 11H), 3.46-3.47 (m, 3H), 3.49-3.72 (m, 4H), 3.82-3.86 (m, 3H), 3.95 (s, 2H), 4.01-4.15 (m, 4H), 4.53-4.56 (m, 2H), 7.84 (s, 1H);

MS (ESI) m/z 974 [M+H]$^+$

Step 4: Preparation of Compound 2d

The compound 2d (19 mg, 66%) was obtained by the same manner as described in the preparation of the compound 2c as a solid except that the compound 7d (40 mg, 0.029 mmol) was used.

$^1$H NMR (400 MHz, D$_2$O) δ 1.25-1.42 (m, 2H), 1.44-1.64 (m, 2H), 1.65-1.76 (m, 1H), 1.78-1.91 (m, 1H), 1.92-2.04 (m, 1H), 2.14-2.22 (m, 0.5H), 2.52 (t, J=7.2 Hz, 2H), 2.59 (t, J=7.2 Hz, 1.5H), 2.64 (t, J=7.2 Hz, 1H), 2.81 (t, J=7.2 Hz, 1H), 2.88 (t, J=7.2 Hz, 1H), 3.03-3.07 (m, 3H), 3.08-3.54 (m, 19H), 3.55-3.65 (m, 7H), 3.66-3.87 (m, 4H), 3.96 (t, J=4.8 Hz, 4H), 4.17-4.22 (m, 1H), 4.25-4.28 (m, 1H), 4.62-4.64 (m, 2H), 7.92 (s, 0.6H), 7.93 (s, 0.4H);

MS (ESI) m/z 974 [M+H]$^+$

<Example 4> Preparation of Compound 2e

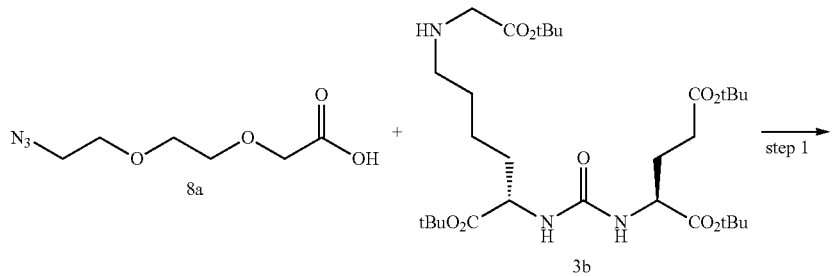

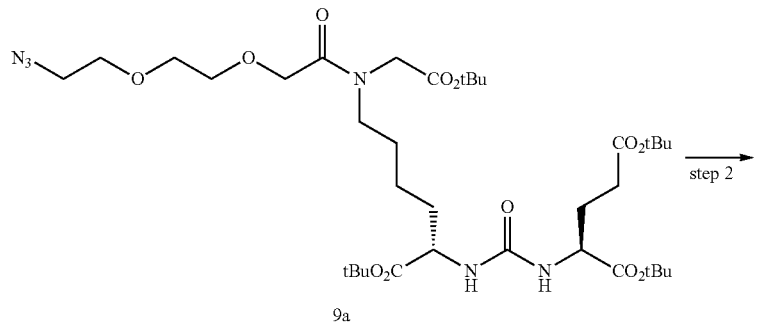

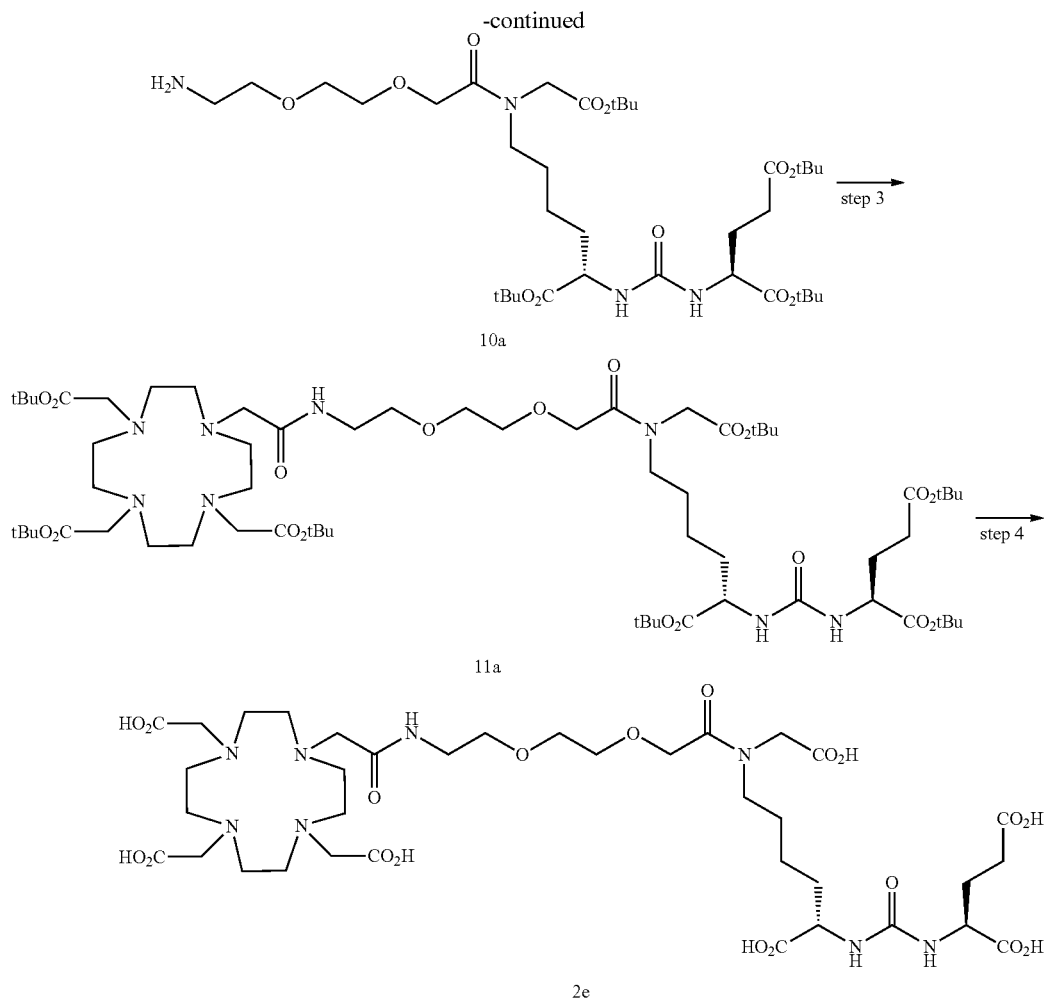

10a

11a

2e

Step 1: Preparation of Compound 9a

The compound 3b (600 mg, 0.997 mmol) synthesized in Example 1 was dissolved in dichloromethane (10 mL), to which N,N'-dicyclohexylcarbodiimide (DCC, 226 mg, 1.04 mmol) was slowly added at room temperature. 2-(2-(2-Azidoethoxy)ethoxy)acetic acid 8a ($N_3$—$(CH_2CH_2O)_2$—$CH_2COOH$, 226 mg, 1.20 mmol) was slowly added thereto, followed by stirring for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (60% ethylacetate/n-hexane) to give the compound 9a (520 mg, 67%) as a colorless liquid.

$^1$H NMR (400 MHz, methanol-$d_4$) δ 1.44-1.49 (m, 36H), 1.50-1.57 (m, 2H), 1.58-1.71 (m, 2H), 1.73-1.84 (m, 2H), 2.00-2.09 (m, 1H), 2.25-2.38 (m, 2H), 3.33-3.39 (m, 4H), 3.65-3.72 (m, 6H), 3.96 (d, J=1.2 Hz, 1H), 4.11-4.22 m, 3H), 4.33 (s, 2H), 6.32-6.36 (m, 1H);

MS (ESI) m/z 773 [M+H]$^+$

Step 2: Preparation of Compound 10a

The compound 9a (490 mg, 0.634 mmol) synthesized in step 1 above was dissolved in ethanol (20 mL), to which 10% palladium on carbon (67 mg) was added, followed by stirring for 12 hours under hydrogen. The reaction solution was filtered, washed with ethanol, and concentrated under reduced pressure. The concentrate was separated by column chromatography (4% methanol/dichloromethane, NH silica gel) to give the compound 10a (425 mg, 90%) as a colorless liquid.

$^1$H NMR (400 MHz, methanol-$d_4$) δ 1.34-1.39 (m, 2H), 1.44-1.49 (m, 36H), 1.51-1.65 (m, 4H), 1.73-1.84 (m, 2H), 2.00-2.07 (m, 1H), 2.31 (q, J=6.8 Hz, 2H), 2.80 (t, J=5.2 Hz, 2H), 3.33-3.40 (m, 3H), 3.52 (q, J=5.2 Hz, 2H), 3.61-3.66 (m, 3H), 3.69-3.71 (m, 1H), 3.97 (d, J=1.2 Hz, 1H), 4.11 (s, 1H), 4.13-4.21 (m, 2H), 4.32 (s, 2H);

MS (ESI) m/z 747 [M+H]$^+$

Step 3: Preparation of Compound 11a

DOTA-tris(tBu) ester (55 mg, 0.096 mmol) was dissolved in dichloromethane (2.0 mL), to which hydroxybenzotriazole (HOBt, 22 mg, 0.160 mmol), TBTU (52 mg, 0.160 mmol) and diisopropylethylamine (0.042 mL, 0.241 mmol) were added, followed by stirring at room temperature for 10 minutes. The compound 10a (60 mg, 0.080 mmol) synthesized in step 2 above dissolved in dichloromethane (2.0 mL) was added thereto, followed by stirring at room temperature for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (3% methanol/dichloromethane) to give the compound 11a (75 mg, 71%) as a colorless liquid.

¹H NMR (400 MHz, methanol-d₄) δ 1.44-1.50 (m, 63H), 1.54-1.65 (m, 4H), 1.73-1.82 (m, 2H), 2.00-2.09 (m, 3H), 2.15-2.34 (m, 6H), 2.59-3.25 (br s, 16H), 3.38-3.40 (m, 2H), 3.55-3.57 (m, 3H), 3.62 (s, 2H), 3.63-3.69 (m, 3H), 3.97 (s, 2H), 4.08 (s, 2H), 4.09-4.21 (m, 3H), 4.31 (s, 2H);

MS (ESI) m/z 1302 [M+H]⁺

Step 4: Preparation of Compound 2e

The compound 11a (50 mg, 0.038 mmol) synthesized in step 3 above was dissolved in 70% trifluoroacetic acid/dichloromethane (0.5 mL), followed by stirring at room temperature for 4 hours. The reactant was concentrated under reduced pressure and separated by high performance liquid chromatography (HPLC) to give the compound 2e (26 mg, 74%) as a white solid.

¹H NMR (400 MHz, D₂O) δ 1.16-1.30 (m, 2H), 1.36-1.50 (m, 2H), 1.52-1.62 (m, 1H), 1.64-1.73 (m, 1H), 1.76-1.86 (m, 1H), 1.98-2.06 (m, 1H), 2.35 (td, J=7.2, 1.6 Hz, 2H), 2.86-3.38 (m, 20H), 3.48-3.60 (m, 10H), 3.70-3.91 (br s, 3H), 3.96 (s, 2H), 4.00-4.12 (m, 3H), 4.25 (s, 2H);

MS (ESI) m/z 910 [M+2H]⁺

<Example 5> Preparation of Compounds 2f, 2g and 2h

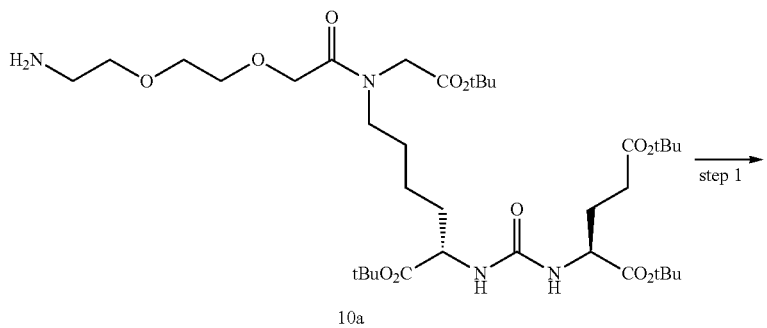

10a

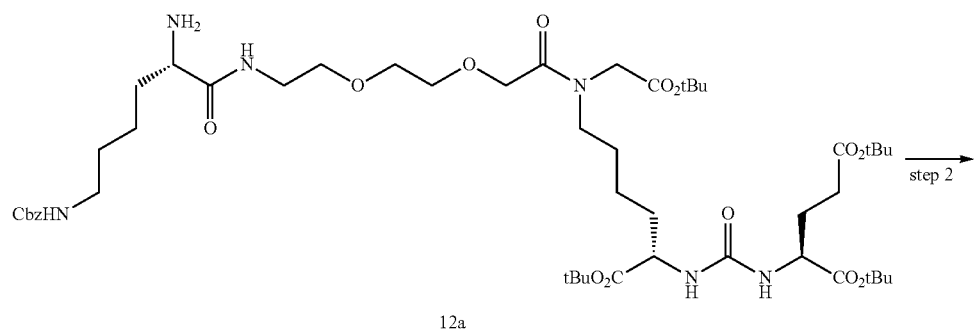

12a

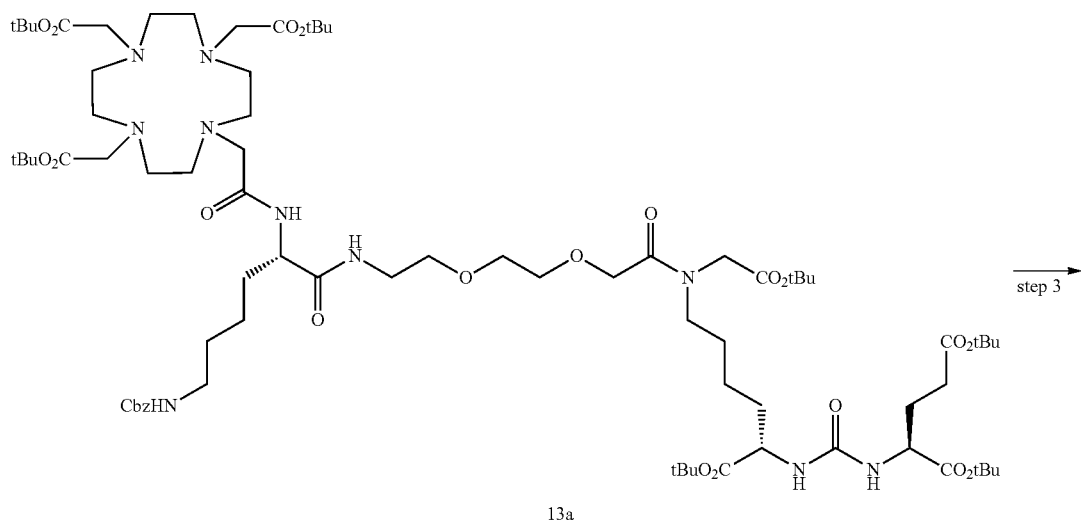

13a

-continued
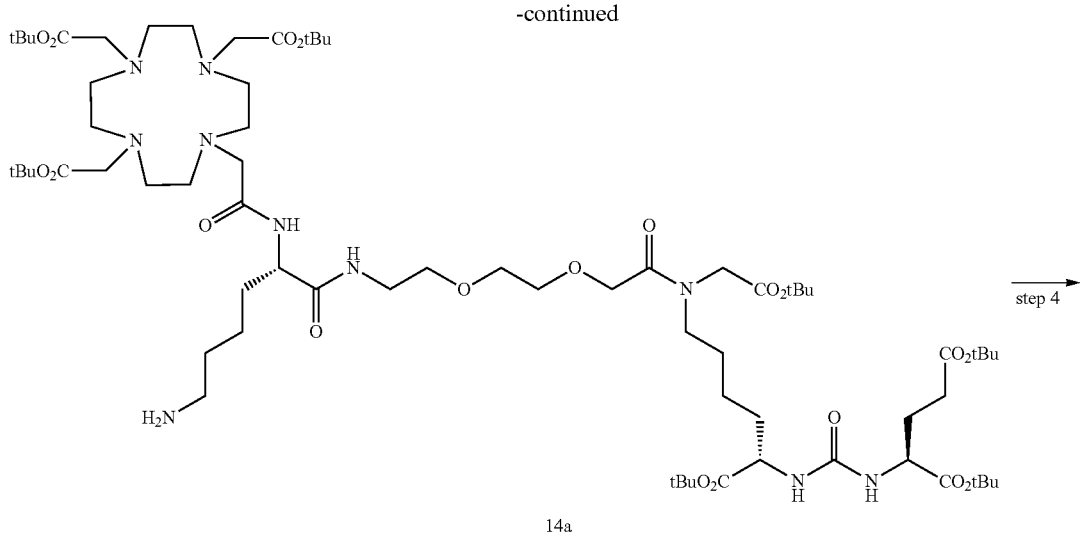
14a
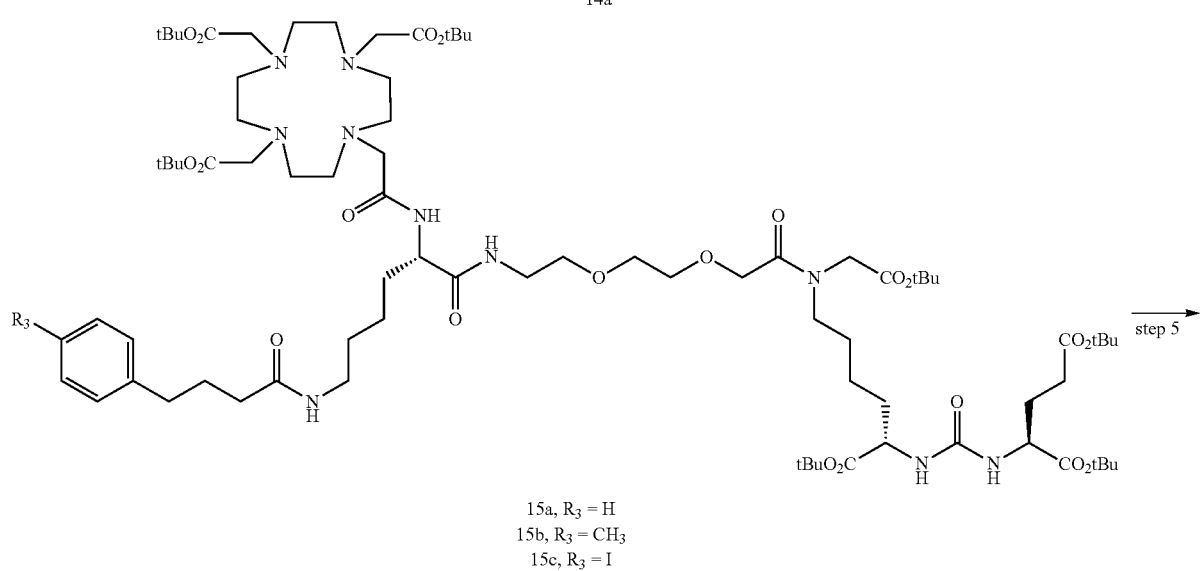
15a, R₃ = H
15b, R₃ = CH₃
15c, R₃ = I
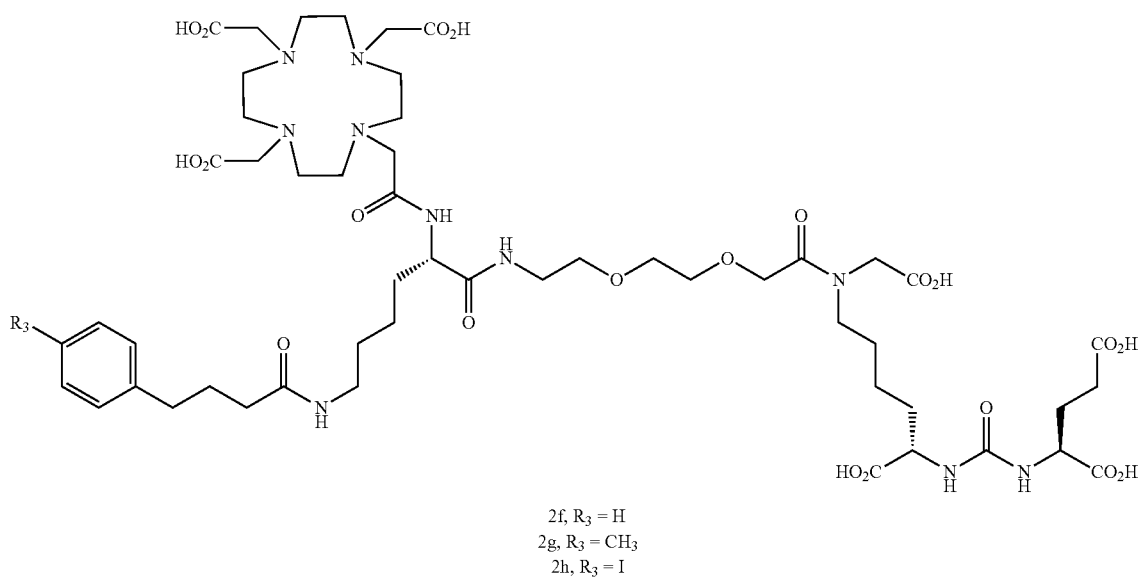
2f, R₃ = H
2g, R₃ = CH₃
2h, R₃ = I Step 1: Preparation of Compound 12a Lysine (Fmoc-Lys(Z)—OH, 275 mg, 0.546 mmol) was dissolved in dichloromethane (10 mL), to which hydroxybenzotriazole (HOBt, 123 mg, 0.1910 mmol), TBTU (292 mg, 0.910 mmol) and diisopropylethylamine (0.238 mL, 1.37 mmol) were added, followed by stirring at room temperature for 10 minutes. The compound 10a (340 mg, 0.455 mmol) synthesized in step 2 of Example 4 dissolved in dichloromethane (5.0 mL) was added thereto, followed by stirring at room temperature for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (2% methanol/dichloromethane). Dichloromethane (15 mL) was added to the obtained compound, to which piperidine (0.043 mL, 0.438 mmol) was added, followed by stirring at room temperature for 24 hours. The reactant was concentrated under reduced pressure, and the concentrate was separated by column chromatography (3% methanol/dichloromethane, NH silica gel) to give the compound 12a (480 mg, 84%) as a colorless liquid.

$^1$H NMR (400 MHz, methanol-$d_4$) δ 1.34-1.39 (m, 2H), 1.44-1.48 (m, 36H), 1.50-1.70 (m, 10H), 1.72-1.84 (m, 2H), 2.00-2.08 (m, 1H), 2.24-2.38 (m, 2H), 3.11 (t, J=6.8 Hz, 2H), 3.33-3.41 (m, 4H), 3.55 (q, J=5.2 Hz, 2H), 3.61-3.68 (m, 4H), 3.96 (d, J=1.6 Hz, 1H), 4.08 (d, J=1.2 Hz, 1H), 4.10-4.21 (m, 3H), 4.31 (s, 1H), 5.06 (s, 2H), 7.27-7.32 (m, 1H), 7.33-7.34 (m, 4H);

MS (ESI) m/z 1010 [M+H]$^+$

Step 2: Preparation of Compound 13a

DOTA-tris(tBu) ester (211 mg, 0.369 mmol) was dissolved in dichloromethane (10 mL), to which hydroxybenzotriazole (HOBt, 83 mg, 0.614 mmol), TBTU (197 mg, 0.614 mmol) and diisopropylethylamine (0.161 mL, 0.921 mmol) were added, followed by stirring at room temperature for 10 minutes. The compound 12a (310 mg, 0.307 mmol) synthesized in step 1 above dissolved in dichloromethane (5.0 mL) was added thereto, followed by stirring at room temperature for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (5% methanol/dichloromethane) to give the compound 13a (323 mg, 67%) as a colorless liquid.

$^1$H NMR (400 MHz, methanol-$d_4$) δ 1.36-1.39 (m, 2H), 1.44-1.49 (m, 63H), 1.51-1.73 (m, 8H), 1.75-1.84 (m, 2H), 2.00-2.07 (m, 3H), 2.08-2.26 (m, 4H), 2.28-2.36 (m, 3H), 2.38-3.05 (br s, 12H), 3.11 (t, J=6.6 Hz, 2H), 3.16-3.28 (m, 4H), 3.36 (t, J=6.6 Hz, 2H), 3.38-3.52 (br s, 3H), 3.54 (q, J=4.0 Hz, 2H), 3.58-3.68 (m, 5H), 3.97 (d, J=4.4 Hz, 1H), 4.07 (S, 1H), 4.09-4.22 (m, 3H), 4.26-4.28 (m, 1H), 4.31 (s, 1H), 5.06 (s, 2H), 7.26-7.32 (m, 1H), 7.33-7.38 (m, 4H);

MS (ESI) m/z 1565 [M+2H]$^+$

Step 3: Preparation of Compound 14a

The compound 13a (300 mg, 0.192 mmol) synthesized in step 2 above was dissolved in ethanol (20 mL), to which 10% palladium on carbon (20 mg) was added, followed by stirring for 2 hours under hydrogen. The reaction solution was filtered, washed with ethanol, and concentrated under reduced pressure. The concentrate was separated by column chromatography (4% methanol/dichloromethane, NH silica gel) to give the compound 14a (260 mg, 95%) as a colorless liquid.

$^1$H NMR (400 MHz, methanol-$d_4$) δ 1.33-1.42 (m, 4H), 1.44-1.49 (m, 63H), 1.51-1.57 (m, 4H), 1.59-1.73 (m, 4H), 1.74-1.85 (m, 3H), 2.00-2.08 (m, 3H), 2.09-2.27 (br s, 4H), 2.29-2.38 (m, 3H), 2.60-2.65 (m, 2H), 2.68 (t, J=7.2 Hz, 2H), 2.73-2.94 (br s, 7H), 3.05-3.17 (br s, 3H), 3.25-3.28 (m, 2H), 3.34-3.39 (m, 2H), 3.43 (br s, 1H), 3.47-3.39 (m, 1H), 3.53-3.57 (m, 3H), 3.63 (s, 2H), 3.65-3.68 (m, 2H), 3.98 (d, J=5.6 Hz, 1H), 4.09 (s, 1H), 4.11-4.22 (m, 3H), 4.32 (s, 2H);

MS (ESI) m/z 1430 [M+H]$^+$

Step 4: Preparation of Compound 15a

4-Phenylbutyric acid (8.4 mg, 0.050 mmol) was dissolved in dichloromethane (1.0 mL), to which hydroxybenzotriazole (HOBt, 11 mg, 0.084 mmol), TBTU (27 mg, 0.084 mmol) and diisopropylethylamine (0.022 mL, 0.126 mmol) were added, followed by stirring at room temperature for 10 minutes. The compound 14a (60 mg, 0.042 mmol) synthesized in step 3 above dissolved in dichloromethane (1.0 mL) was added thereto, followed by stirring at room temperature for 2 hours. Water was added to the reactant, and then the organic compound was repeatedly extracted 3 times using dichloromethane. The collected organic solvent was dried over anhydrous sodium sulfate, concentrated under reduced pressure and separated by column chromatography (4% methanol/dichloromethane) to give the compound 15a (17 mg, 26%) as a colorless liquid.

$^1$H NMR (400 MHz, methanol-$d_4$) δ 1.44-1.48 (m, 63H), 1.51-1.71 (m, 6H), 1.74-1.84 (m, 4H), 1.86-1.94 (m, 2H), 1.98-2.15 (m, 6H), 2.19 (t, J=7.4 Hz, 2H), 2.24-2.34 (m, 3H), 2.36-3.04 (br s, 3H), 2.61 (t, J=7.8 Hz, 2H), 2.63-3.04 (br s, 10H), 3.12-3.19 (m, 3H), 3.25-3.26 (m, 4H), 3.35-3.37 (m, 4H), 3.47-3.56 (m, 5H), 3.59-3.68 (m, 4H), 3.97 (d, J=4.0 Hz, 1H), 4.08-4.22 (m, 4H), 4.31 (s, 2H), 7.1-7.18 (m, 3H), 7.24-7.27 (m, 2H);

MS (ESI) m/z 1577 [M+H]$^+$

Step 4: Preparation of Compound 15b

The compound 15b (17 mg, 26%) was obtained by the same manner as described in the preparation of the compound 15a as a colorless liquid except that 4-(p-tolyl)butyric acid (12 mg, 0.063 mmol), hydroxybenzotriazole (HOBt, 14 mg, 0.106 mmol), TBTU (34 mg, 0.106 mmol), diisopropylethylamine (0.028 mL, 0.159 mmol) and the compound 14a (76 mg, 0.053 mmol) synthesized in step 3 above were used.

MS (ESI) m/z 1590 [M+H]$^+$

Step 4: Preparation of Compound 15c

The compound 15c (36 mg, 51%) was obtained by the same manner as described in the preparation of the compound 15a as a colorless liquid except that 4-(p-iodophenyl)butyric acid (15 mg, 0.050 mmol), hydroxybenzotriazole (HOBt, 11 mg, 0.084 mmol), TBTU (27 mg, 0.084 mmol), diisopropylethylamine (0.022 mL, 0.126 mmol) and the compound 14a (60 mg, 0.042 mmol) synthesized in step 3 above were used.

$^1$H NMR (400 MHz, methanol-$d_4$) δ 1.44-1.48 (m, 63H), 1.51-1.57 (m, 4H), 1.58-1.70 (m, 3H), 1.71-1.82 (m, 3H), 1.84-1.92 (m, 3H), 1.93-2.15 (m, 5H), 2.18 (t, J=7.6 Hz, 2H), 2.20-2.34 (m, 5H), 2.36-2.56 (br s, 3H), 2.58 (t, J=7.6 Hz, 2H), 2.61-2.76 (br s, 3H), 2.81 (s, 2H), 2.86-3.09 (br s, 5H), 3.11-3.18 (m, 3H), 3.20-3.26 (m, 3H), 3.35-3.39 (m, 2H), 3.42-3.48 (br s, 2H), 3.53 (q, J=4.0 Hz, 2H), 3.62 (s, 2H), 3.64-3.69 (m, 3H), 3.97 (d, J=3.6 Hz, 1H), 4.08 (s, 1H), 4.10-4.23 (m, 4H), 4.31 (s, 2H), 6.32-6.36 (m, 1H), 6.99 (d, J=8.4 Hz, 2H), 7.60 (d, J=8.0 Hz, 2H);

MS (ESI) m/z 1702 [M+H]$^+$

Step 5: Preparation of Compound 2f

The compound 15a (14 mg, 0.0089 mmol) synthesized in step 4 above was dissolved in 70% trifluoroacetic acid/dichloromethane (0.5 mL), followed by stirring at room temperature for 1 hour. The reactant was concentrated under reduced pressure, and the concentrate was separated by high performance liquid chromatography (HPLC) to give the compound 2f (7 mg, 67%) as a white solid.

$^1$H NMR (400 MHz, D$_2$O) δ 1.22-1.31 (m, 4H), 1.39 (p, J=7.4 Hz, 2H), 1.42-1.51 (m, 2H), 1.57-1.73 (m, 4H), 1.79 (p, J 7.6 Hz, 2H), 1.82-1.89 (m, 1H), 2.01-2.09 (m, 1H), 2.13 (t, J=7.2 Hz, 2H), 2.39 (t, J=7.2 Hz, 2H), 2.51 (t, J=7.4 Hz, 2H), 2.53-3.00 (br s, 3H), 3.03 (t, J=6.8 Hz, 2H), 3.09-3.43 (m, 18H), 3.47 (q, J=5.2 Hz, 2H), 3.48-3.60 (m, 6H), 3.61-3.91 (br s, 5H), 3.96 (s, 2H), 4.00-4.16 (m, 3H), 4.25 (s, 2H), 7.13-7.17 (m, 3H), 7.22-7.27 (m, 2H);

MS (ESI) m/z 1183 [M+H]$^+$, 1181 [M−H]$^−$

Step 5: Preparation of Compound 2g

The compound 2g (10 mg, 36%) was obtained by the same manner as described in the preparation of the compound 2f as a white solid except that the compound 15b (37 mg, 0.023 mmol) synthesized in step 4 above and 70% trifluoroacetic acid/dichloromethane (0.5 mL) were used.

$^1$H NMR (400 MHz, D$_2$O) δ 1.14-1.26 (m, 4H), 1.35 (p, J=6.8 Hz, 2H), 1.39-1.48 (m, 2H), 1.50-1.63 (m, 3H), 1.66-1.69 (m, 1H), 1.72 (p, J=7.2 Hz, 2H), 1.82 (p, J=7.2 Hz, 1H), 2.01 (p, J=7.0 Hz, 1H), 2.08 (t, J=7.2 Hz, 2H), 2.15 (s, 3H), 2.35 (t, J=7.2 Hz, 2H), 2.43 (t, J=7.4 Hz, 2H), 2.66-2.98 (br s, 2H), 2.99 (t, J=6.6 Hz, 2H), 3.01-3.40 (m, 18H), 3.44 (q, J=5.0 Hz, 2H), 3.48-3.56 (m, 5H), 3.57-3.88 (br s, 6H), 3.92 (s, 2H), 3.98-4.12 (m, 4H), 4.21 (s, 2H), 7.01 (d, J=8.0 Hz, 2H), 7.04 (d, J=8.0 Hz, 2H);

MS (ESI) m/z 1198 [M+H]$^+$, 1196 [M−H]$^−$

Step 5: Preparation of Compound 2h

The compound 2h (13 mg, 54%) was obtained by the same manner as described in the preparation of the compound 15a as a white solid except that the compound 15c (30 mg, 0.018 mmol) synthesized in step 4 above and 70% trifluoroacetic acid/dichloromethane (0.5 mL) were used.

$^1$H NMR (400 MHz, D$_2$O) δ 1.18-1.30 (m, 4H), 1.37 (p, J=6.8 Hz, 2H), 1.41-1.52 (m, 2H), 1.54-1.67 (m, 3H), 1.70-1.74 (m, 1H), 1.78 (t, J=7.4 Hz, 2H), 1.81-1.90 (m, 1H), 1.98-2.07 (m, 1H), 2.11 (t, J=7.2 Hz, 2H), 2.39 (t, J=7.2 Hz, 2H), 2.48 (t, J=7.4 Hz, 2H), 3.00 (t, J=6.8 Hz, 2H), 3.02-3.26 (m, 17H), 3.29-3.35 (m, 2H), 3.48 (q, J=4.4 Hz, 2H), 3.52-3.58 (m, 6H), 3.60-3.93 (br s, 7H), 3.97 (s, 2H), 4.03-4.17 (m, 3H), 4.25 (s, 2H), 6.95 (d, J=8.4 Hz, 2H), 7.59 (d, J=8.4 Hz, 2H);

MS (ESI) m/z 1309 [M+H]$^+$, 1307 [M−H]$^−$

<Example 6> Preparation of Compound 2i

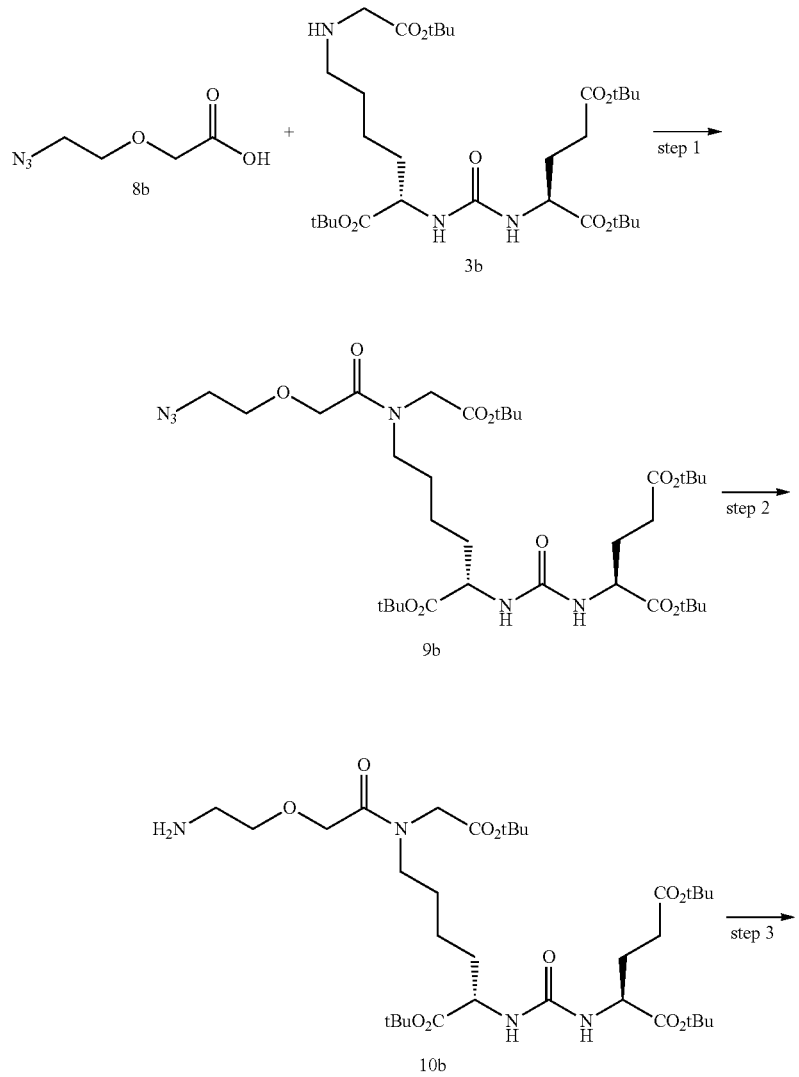

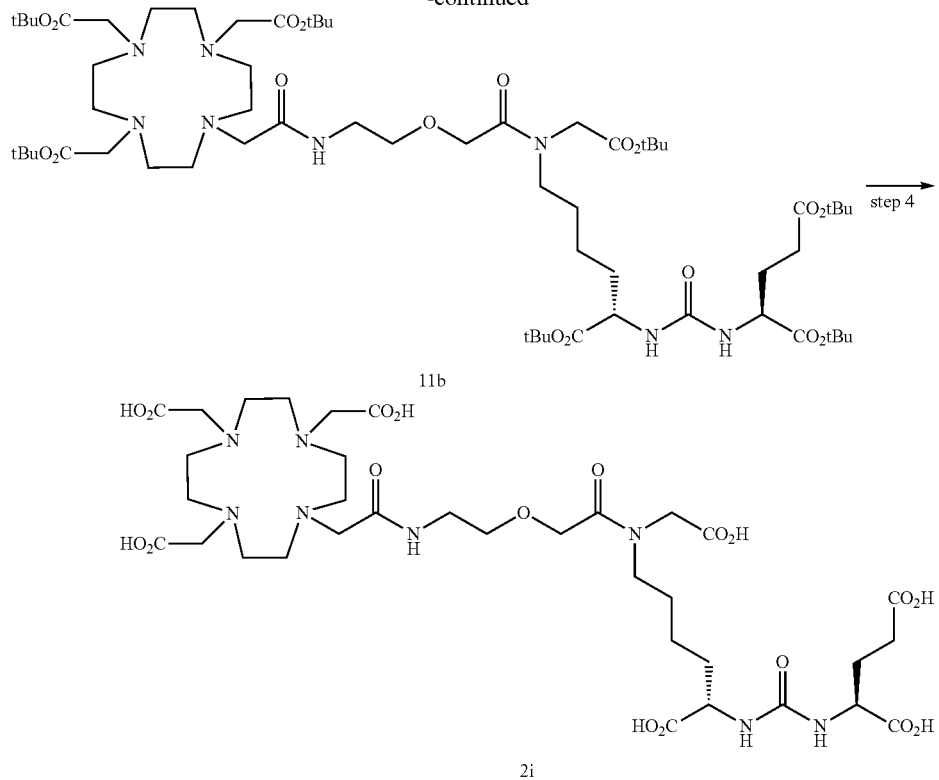

Step 1: Preparation of Compound 9b

The compound 3b (691 mg, 1.15 mmol) synthesized in Example 1 was dissolved in dichloromethane (10 mL), to which N,N'-dicyclohexylcarbodiimide (DCC, 3710 mg, 1.79 mmol) was slowly added at room temperature. 2-(2-Azidoethoxy) acetic acid 8b ($N_3$—$CH_2CH_2O$—$CH_2COOH$, 200 mg, 1.38 mmol) was added thereto, followed by stirring for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (40% ethylacetate/n-hexane) to give the compound 9b (670 mg, 80%) as a colorless liquid.

$^1$H NMR (400 MHz, methanol-$d_4$) δ 1.44-1.51 (m, 36H), 1.52-1.67 (m, 4H), 1.71-1.84 (m, 2H), 2.00-2.09 (m, 1H), 2.25-2.38 (m, 2H), 3.36 (q, J=7.5 Hz, 2H), 3.41-3.45 (m, 2H), 3.66 (t, J=5.0 Hz, 1H), 3.71 (t, J=5.0 Hz, 1H), 3.97 (d, J=0.8 Hz, 1H), 4.11 (d, J=1.2 Hz, 1H), 4.12-4.23 (m, 3H), 4.32 (s, 2H), 6.34 (p, J=4.2 Hz, 2H);

MS (ESI) m/z 729 [M+H]$^+$

Step 2: Preparation of Compound 10b

The compound 9b (650 mg, 0.892 mmol) synthesized in step 1 above was dissolved in ethanol (20 mL), to which 10% palladium on carbon (95 mg) was added, followed by stirring for 12 hours under hydrogen. The reaction solution was filtered, washed with ethanol, and concentrated under reduced pressure. The concentrate was separated by column chromatography (2% methanol/dichloromethane, NH silica gel) to give the compound 10b (573 mg, 91%) as a colorless liquid.

$^1$H NMR (400 MHz, methanol-$d_4$) δ 1.37-1.42 (m, 2H), 1.44-1.49 (m, 36H), 1.51-1.67 (m, 4H), 1.71-1.84 (m, 2H), 1.99-2.09 (m, 1H), 2.29-2.34 (m, 2H), 2.84 (p, J=5.2 Hz, 2H), 3.35-3.40 (m, 1H), 3.54 (t, J=5.4 Hz, 1H), 3.59 (t, J=5.4 Hz, 1H), 3.98 (d, J=0.8 Hz, 1H), 4.07 (s, 1H), 4.09-4.21 (m, 2H), 4.31 (s, 2H);

MS (ESI) m/z 703 [M+H]$^+$

Step 3: Preparation of Compound 11b

DOTA-tris(tBu) ester (82 mg, 0.143 mmol) was dissolved in dichloromethane (2.0 mL), to which hydroxybenzotriazole (HOBt, 32 mg, 0.239 mmol), TBTU (77 mg, 0.239 mmol) and diisopropylethylamine (0.062 mL, 0.358 mmol) were added, followed by stirring at room temperature for 10 minutes. The compound 10b (84 mg, 0.120 mmol) synthesized in step 2 above dissolved in dichloromethane (2.0 mL) was added thereto, followed by stirring at room temperature for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (2% methanol/dichloromethane) to give the compound 11b (65 mg, 43%) as a colorless liquid.

$^1$H NMR (400 MHz, methanol-$d_4$) δ 1.44-1.49 (m, 63H), 1.51-1.54 (m, 2H), 1.57-1.65 (m, 2H), 1.75-1.84 (m, 2H), 2.04-2.09 (m, 2H), 2.30-2.34 (m, 2H), 2.81-3.25 (br s, 18H), 3.35-3.54 (br s 7H), 3.55 (t, J=5.4 Hz, 2H), 3.61 (t, J=5.2 Hz, 2H), 3.98 (s, 2H), 4.06 (s, 1H), 4.10-4.22 (m, 2H), 4.29 (s, 2H);

MS (ESI) m/z 1258 [M+H]$^+$

Step 4: Preparation of Compound 2i

The compound 11b (55 mg, 0.044 mmol) synthesized in step 3 above was dissolved in 70% trifluoroacetic acid/dichloromethane (0.5 mL), followed by stirring at room temperature for 4 hours. The reactant was concentrated under reduced pressure, and the concentrate was separated by high performance liquid chromatography (HPLC) to give the compound 2i (17 mg, 45%) as a white solid.
¹H NMR (400 MHz, D₂O) δ 1.20-1.34 (m, 2H), 1.42-1.54 (m, 2H), 1.56-1.65 (m, 1H), 1.70-1.77 (m, 1H), 1.86 (p, J=7.4 Hz, 1H), 2.05 (p, J=7.2 Hz, 1H), 2.39 (t, J=7.2 Hz, 2H), 2.84-3.49 (m, 20H), 3.51 (t, J=5.0 Hz, 1H), 3.55 (t, J=4.0 Hz, 1H), 3.58-3.62 (br s, 4H), 3.63-3.95 (br s, 3H), 4.00 (s, 2H), 4.05 (s, 1H), 4.07-4.17 (m, 2H), 4.29 (s, 2H);
MS (ESI) m/z 865 [M+H]⁺, 863 [M−H]⁻
<Example 7> Preparation of Compounds 2j and 2k
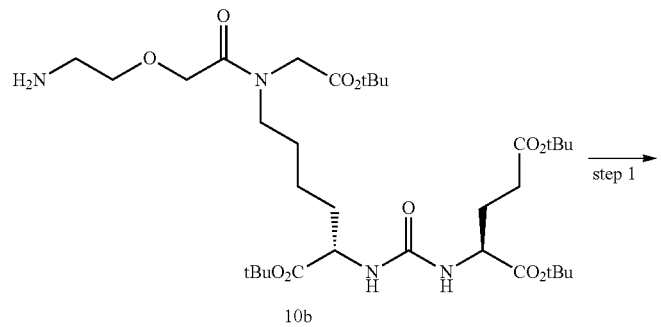
10b
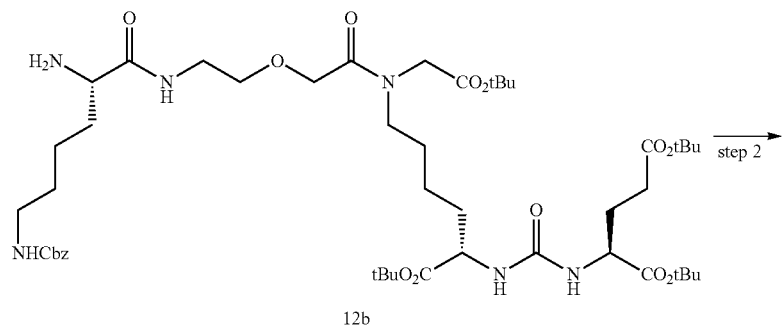
12b
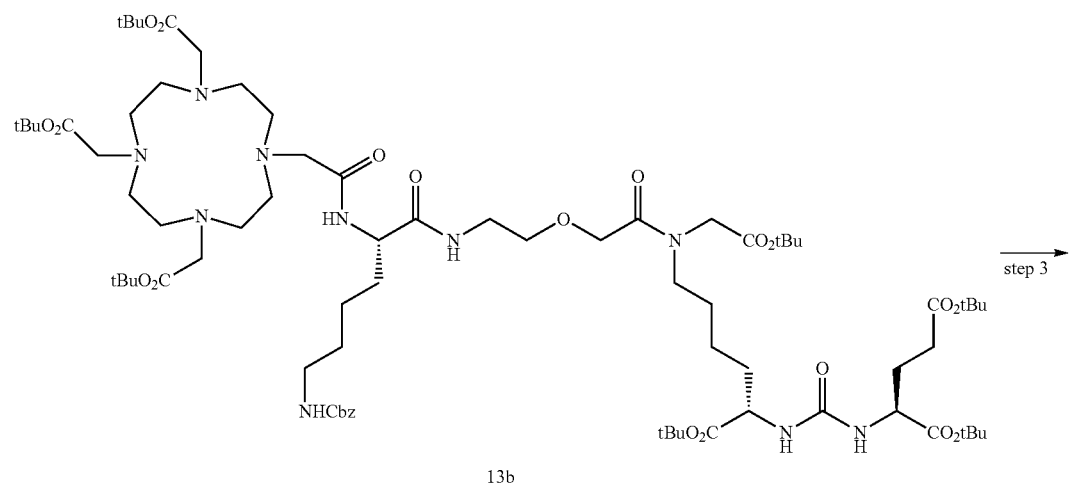
13b -continued
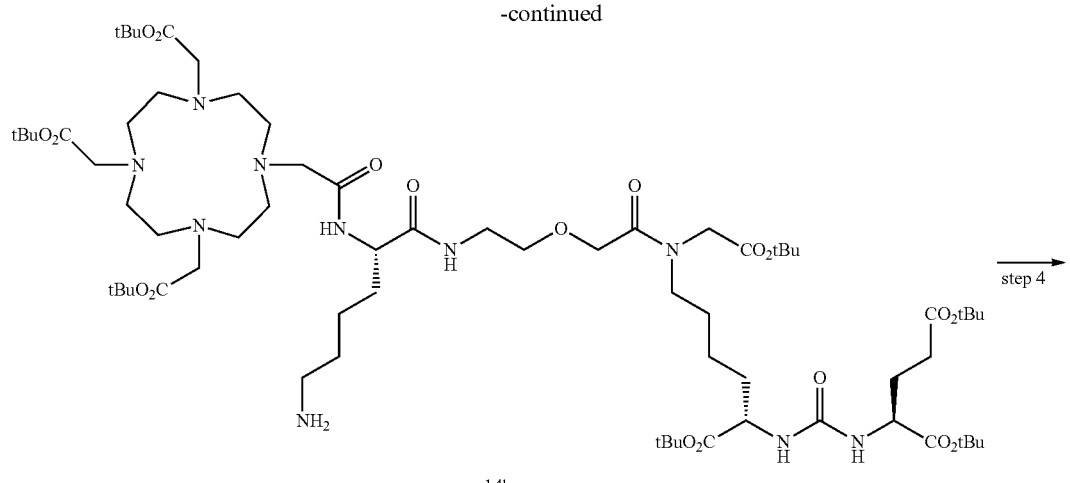
14b
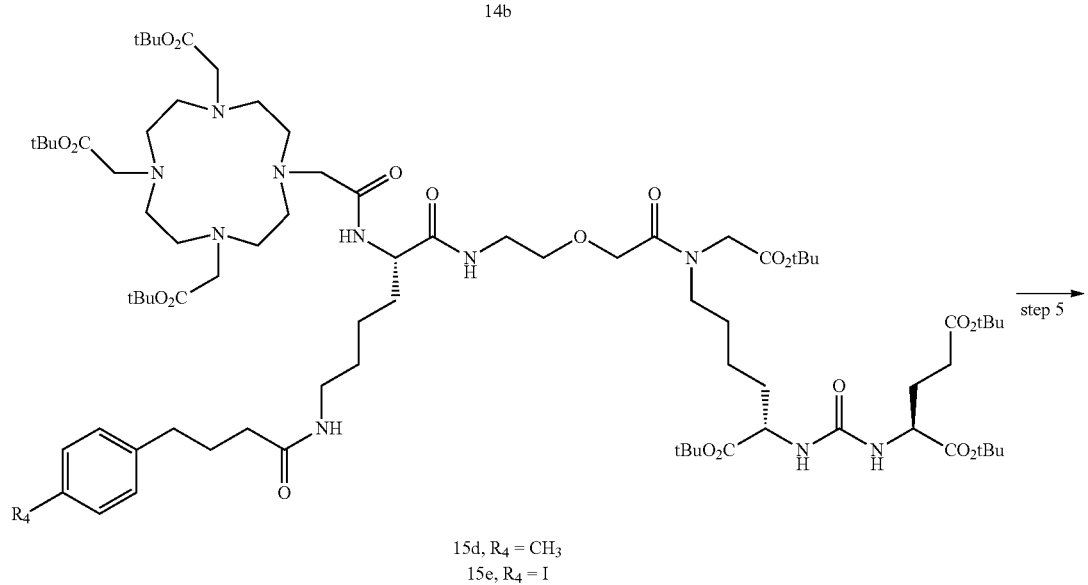
15d, R₄ = CH₃
15e, R₄ = I
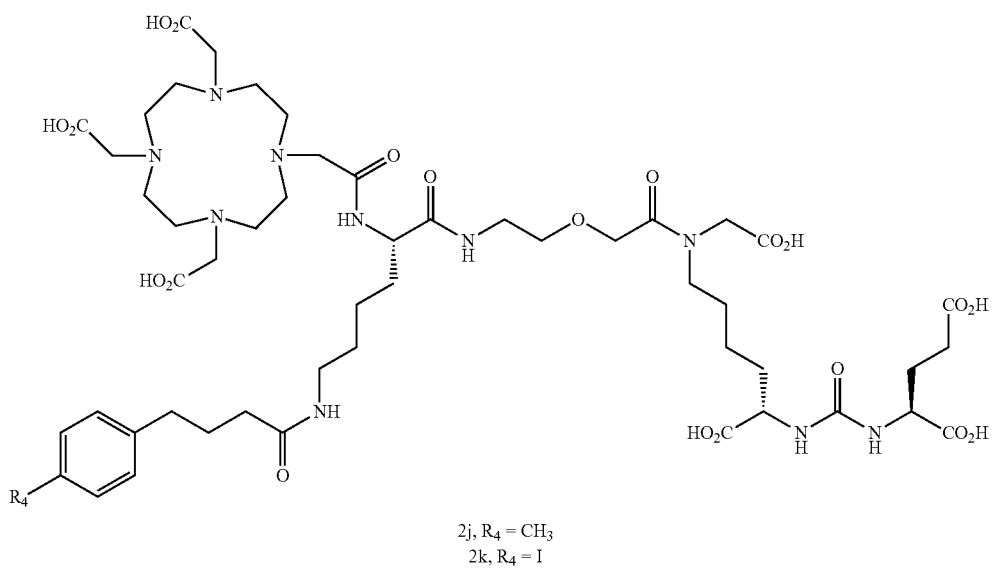
2j, R₄ = CH₃
2k, R₄ = I Step 1: Preparation of Compound 12b Lysine (Fmoc-Lys(Z)—OH, 386 mg, 0.768 mmol) was dissolved in dichloromethane (10 mL), to which hydroxybenzotriazole (HOBt, 173 mg, 1.28 mmol), TBTU (411 mg, 1.28 mmol) and diisopropylethylamine (0.335 mL, 1.92 mmol) were added, followed by stirring at room temperature for 10 minutes. The compound 10b (450 mg, 0.640 mmol) synthesized in step 2 of Example 6 dissolved in dichloromethane (5.0 mL) was added thereto, followed by stirring at room temperature for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (2% methanol/dichloromethane). Dichloromethane (15 mL) was added to the obtained compound, to which piperidine (0.050 mL, 0.505 mmol) was added, followed by stirring at room temperature for 24 hours. The reactant was concentrated under reduced pressure, and the concentrate was separated by column chromatography (3% methanol/dichloromethane, NH silica gel) to give the compound 12b (380 mg, 61%) as a colorless liquid.

$^1$H NMR (400 MHz, methanol-$d_4$) δ 1.33-1.41 (m, 4H), 1.44-1.48 (m, 36H), 1.51-1.72 (m, 8H), 1.74-1.84 (m, 2H), 1.99-2.08 (m, 1H), 2.24-2.38 (m, 2H), 3.11 (t, J=6.8 Hz, 2H), 3.24-3.28 (m, 1H), 3.34-3.46 (m, 3H), 3.55 (t, J=5.4 Hz, 1H), 3.60 (t, J=5.4 Hz, 1H), 3.96 (s, 1H), 4.05 (d, J=1.2 Hz, 1H), 4.16-4.22 (m, 3H), 4.29 (s, 1H), 5.05 (s, 2H), 7.26-7.32 (m, 1H), 7.33-7.38 (m, 4H);

MS (ESI) m/z 966 [M+H]$^+$

Step 2: Preparation of Compound 13b

DOTA-tris(tBu) ester (271 mg, 0.472 mmol) was dissolved in dichloromethane (10 mL), to which hydroxybenzotriazole (HOBt, 106 mg, 0.787 mmol), TBTU (253 mg, 0.787 mmol) and diisopropylethylamine (0.206 mL, 1.18 mmol) were added, followed by stirring at room temperature for 10 minutes. The compound 12b (380 mg, 0.394 mmol) synthesized in step 1 above dissolved in dichloromethane (5.0 mL) was added thereto, followed by stirring at room temperature for 1 hour. Water was added to the reactant, and then the organic compound was repeatedly extracted 3 times using dichloromethane. The collected organic solvent was dried over anhydrous sodium sulfate, concentrated under reduced pressure and separated by column chromatography (3% methanol/dichloromethane) to give the compound 13b (487 mg, 81%) as a colorless liquid.

$^1$H NMR (400 MHz, methanol-$d_4$) δ 1.44-1.49 (m, 63H), 1.51-1.53 (m, 2H), 1.59-1.66 (m, 4H), 1.75-1.84 (m, 4H), 2.01-2.09 (m, 3H), 2.10-2.26 (br s, 4H), 2.27-2.34 (m, 3H), 2.38-2.94 (br s, 12H), 2.95-3.21 (m, 6H), 3.23-3.27 (m, 2H), 3.32-3.64 (m, 8H), 3.99-4.08 (m, 2H), 4.11-4.22 (m, 3H), 4.30 (s, 2H), 5.06 (s, 2H), 7.28-7.31 (m, 1H), 7.33-7.34 (m, 4H);

MS (ESI) m/z 1520 [M+H]$^+$

Step 3: Preparation of Compound 14b

The compound 13b (467 mg, 0.307 mmol) synthesized in step 2 above was dissolved in ethanol (20 mL), to which 10% palladium on carbon (33 mg) was added, followed by stirring for 2 hours under hydrogen. The reaction solution was filtered, washed with ethanol, and concentrated under reduced pressure. The concentrate was separated by column chromatography (2% methanol/dichloromethane, NH silica gel) to give the compound 14b (366 mg, 86%) as a colorless liquid.

$^1$H NMR (400 MHz, methanol-$d_4$) δ 1.44-1.49 (m, 63H), 1.51-1.67 (m, 8H), 1.74-1.84 (m, 3H), 1.89-2.00 (br s, 1H), 2.01-2.08 (m, 2H), 2.09-2.26 (br s, 5H), 2.29-2.34 (m, 2H), 2.36-2.62 (br s, 5H), 2.63-2.68 (m, 2H), 2.70-3.22 (br s 10H), 3.26 (t, J=7.6 Hz, 2H), 3.39 (t, J=7.2 Hz, 2H), 3.42-3.73 (m, 6H), 3.95-4.06 (m, 2H), 4.08-4.21 (m, 4H), 4.32 (s, 2H);

MS (ESI) m/z 1386 [M+H]$^+$

Step 4: Preparation of Compound 15d 4-(p-Tolyl)butyric acid (11 mg, 0.059 mmol) was dissolved in dichloromethane (1.0 mL), to which hydroxybenzotriazole (HOBt, 13 mg, 0.098 mmol), TBTU (32 mg, 0.098 mmol) and diisopropylethylamine (0.026 mL, 0.147 mmol) were added, followed by stirring at room temperature for 10 minutes. The compound 14b (68 mg, 0.049 mmol) synthesized in step 3 above dissolved in dichloromethane (1.0 mL) was added thereto, followed by stirring at room temperature for 2 hours. Water was added to the reactant, and then the organic compound was repeatedly extracted 3 times using dichloromethane. The collected organic solvent was dried over anhydrous sodium sulfate, concentrated under reduced pressure and separated by column chromatography (4% methanol/dichloromethane) to give the compound 15d (60 mg, 42%) as a colorless liquid.

Step 4: Preparation of Compound 15e

The compound 15e (36 mg, 51%) was obtained by the same manner as described in the preparation of the compound 15a as a colorless liquid except that 4-(p-iodophenyl)butyric acid (32 mg, 0.104 mmol), hydroxybenzotriazole (HOBt, 23 mg, 0.173 mmol), TBTU (56 mg, 0.173 mmol), diisopropylethylamine (0.045 mL, 0.260 mmol) and the compound 14b (120 mg, 0.087 mmol) synthesized in step 3 above were used.

$^1$H NMR (400 MHz, CDCl$_3$) δ 0.82-0.96 (m, 2H), 0.97-1.14 (m, 2H), 1.16-1.37 (m, 6H), 1.42-1.50 (m, 63H), 1.53-1.69 (m, 2H), 1.71-1.96 (m, 5H), 1.99-2.10 (m, 3H), 2.11-2.38 (m, 11H), 2.41-2.68 (m, 6H), 2.81 (s, 3H), 2.82-3.11 (br s, 7H), 3.16-3.33 (m, 5H), 3.35-3.61 (m, 5H), 3.63-3.75 (m, 2H), 3.90 (s, 2H), 4.10 (d, J=3.2 Hz, 1H), 4.24-4.35 (m, 3H), 5.60 (q, J=7.6 Hz, 1H), 6.97 (d, J=8.0 Hz, 2H), 7.55 (d, J=8.0 Hz, 2H);

MS (ESI) m/z 1658 [M+H]$^+$

Step 5: Preparation of Compound 2j

The compound 15d (24 mg, 0.016 mmol) synthesized in step 4 above was dissolved in 70% trifluoroacetic acid/dichloromethane (0.5 mL), followed by stirring at room temperature for 1 hour. The reactant was concentrated under reduced pressure, and the concentrate was separated by high performance liquid chromatography (HPLC) to give the compound 2j (6.7 mg, 37%) as a white solid.

$^1$H NMR (400 MHz, D$_2$O) δ 1.16-1.28 (m, 4H), 1.35-1.48 (m, 4H), 1.52-1.64 (m, 3H), 1.65-1.70 (m, 1H), 1.74 (t, J=7.6 Hz, 2H), 1.79-1.87 (m, 1H), 2.00-2.05 (m, 1H), 2.10 (t, J=7.0 Hz, 2H), 2.16 (s, 3H), 2.36 (t, J=6.6 Hz, 2H), 2.44 (t, J=7.2 Hz, 2H), 2.82-3.10 (m, 8H), 3.11-3.27 (m, 9H), 3.28-3.38 (m, 4H), 3.39-3.49 (m, 4H), 3.50-3.80 (m, 7H), 3.93 (s, 2H), 3.98-4.12 (m, 3H), 4.19 (s, 2H), 7.02 (d, J=8.0 Hz, 2H), 7.06 (d, J=7.2 Hz, 2H);

MS (ESI) m/z 1153 [M+H]$^+$, 1151 [M−H]$^-$

Step 5: Preparation of Compound 2k

The compound 2k (4.0 mg, 53%) was obtained by the same manner as described in the preparation of the compound 2j as a white solid except that the compound 15e (10 mg, 0.0060 mmol) synthesized in step 4 above was used.

$^1$H NMR (400 MHz, D$_2$O) δ 1.15-1.27 (m, 4H), 1.28-1.36 (m, 2H), 1.38-1.48 (m, 2H), 1.54-1.64 (m, 3H), 1.66-1.68 (m, 1H), 1.74 (p, J=7.4 Hz, 2H), 1.79-1.87 (m, 1H), 1.98-2.03 (m, 1H), 2.08 (t, J=7.0 Hz, 2H), 2.36 (t, J=7.4 Hz, 2H), 2.43 (t, J=7.2 Hz, 2H), 2.71-2.87 (br s, 3H), 2.96 (t, J=6.6 Hz, 2H), 3.03-3.33 (m, 17H), 3.38-3.49 (m, 3H), 3.52-3.89

(br s, 6H), 3.94 (d, J=4.4 Hz, 2H), 4.00-4.14 (m, 4H), 4.19 (s, 2H), 6.90 (d, J=8.4 Hz, 2H), 7.54 (d, J=8.0 Hz, 2H);

MS (ESI) m/z 1266 [M+H]+, 1264 [M−H]−

<Example 8> Preparation of Compound 21

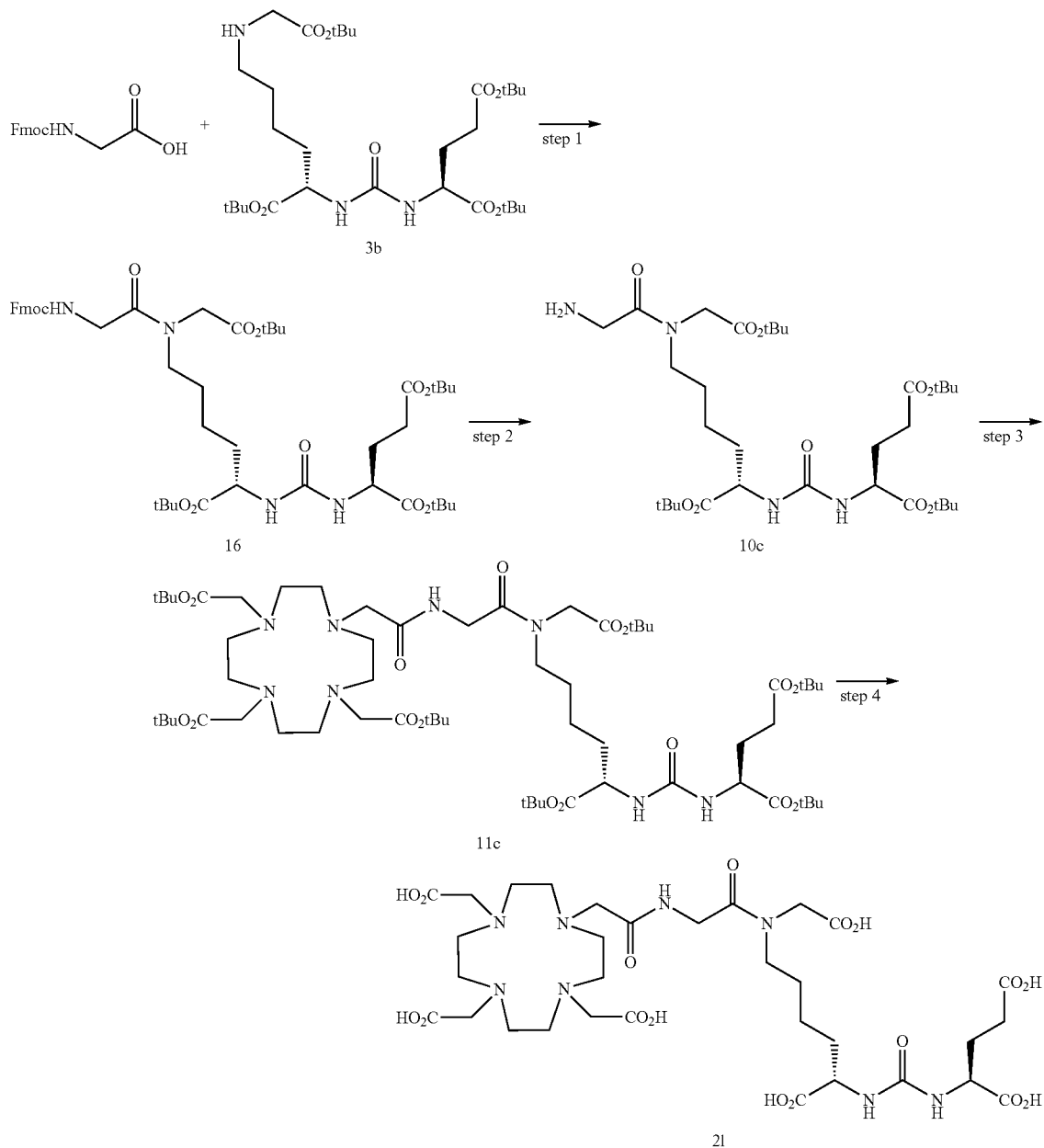

separated by column chromatography (35%-50% ethylacetate/n-hexane) to give the compound 16 (0.45 g, 61%).

$^1$H NMR (400 MHz, CDCl$_3$) δ 1.05-1.21 (m, 2H), 1.38 (s, 9H), 1.40 (s, 9H), 1.43 (s, 9H), 1.45 (s, 9H), 1.56-1.62 (m, 2H), 1.64-1.71 (m, 2H), 1.75-1.86 (m, 2H), 1.88-1.94 (m, 2H), 2.19-2.35 (m, 2H), 3.16-3.29 3.88-4.02 (m, 2H), 4.19- 4.28 (m, 2H), 4.29-4.40 (m, 3H), 5.23 (dt, J=64.4, 12.0 Hz, 2H), 5.96 (dt, J=105.2, 4.4 Hz, 1H), 7.27-7.30 (m, 2H), 7.37 (t, J=13.4 Hz, 2H), 7.55 (d, J=7.2 Hz, 2H), 7.74 (d, J=7.2 Hz, 2H);

MS (ESI) m/z 881 [M+H]+

Step 2: Preparation of Compound 10c

The compound 16 (0.40 g, 0.45 mmol) was dissolved in dichloromethane (10 mL), to which piperidine (0.1 mL, 1.01 mmol) was added, followed by stirring at room temperature Step 1: Preparation of Compound 16

Fmoc-Gly-OH (0.49 g, 1.66 mmol) was dissolved in dichloromethane (10 mL), to which N,N'-dicyclohexylcarbodiimide (0.34 g, 1.66 mmol) was added, followed by stirring at 0° C. for 10 minutes. The compound 3b (0.50 g, 0.83 mmol) dissolved in dichloromethane (10 mL) was slowly added to the reaction mixture, followed by stirring at 0° C. for 1.5 hours. The reaction mixture was filtered, washed with dichloromethane several times, and the solvent was eliminated under reduced pressure. The concentrate was for 1.5 hours. The reaction mixture was concentrated under reduced pressure, and the concentrate was separated by column chromatography (5% methanol/dichloromethane) to give the compound 10c (0.19 g, 63%).

$^1$H NMR (400 MHz, CDCl$_3$) δ 1.41 (s, 9H), 1.43 (s, 9H), 1.46 (s, 9H), 1.47 (s, 9H) 1.53-1.64 (m, 2H) 1.75-1.89 (m, 2H), 2.02-2.11 (m, 2H), 2.24-2.38 (m, 2H), 3.23 (t, J=7.4 Hz, 2H), 3.63 (s, 2H), 3.69 (s, 2H), 3.84-3.97 (m, 2H), 4.22-4.37 (m, 2H), 5.46-5.84 (m, 2H);

MS (EST) m/z 659 [M+H]$^+$

Step 3: Preparation of Compound 11c

DOTA-tris(tBu) ester (31 mg, 55 μmol) was dissolved in dichloromethane (0.6 mL), to which hydroxybenzotriazole (HOBt, 9 mg, 68 μmol), TBTU (22 mg, 68 μmol) and diisopropylethylamine (16 μL, 91 μmol) were added, followed by stirring at room temperature for 10 minutes. The compound 10c (30 mg, 45.5 μmol) dissolved in dichloromethane (0.3 mL) was added thereto, followed by stirring at room temperature for 1 hour. The reaction was terminated by adding water (10 mL), and the organic compound was extracted using dichloromethane (10 mL×3). The reactant was dried over anhydrous sodium sulfate, concentrated under reduced pressure, and the concentrate was separated by column chromatography (5% methanol/dichloromethane) to give the compound 11c (47.4 mg, 86%).

$^1$H NMR (400 MHz, CDCl$_3$) δ 1.46 (s, 9H), 1.47 (s, 27H), 1.48 (s, 27H), 1.68 (s, 6H), 1.73-1.80 (m, 1H), 1.78-1.90 (m, 1H), 2.04-2.15 (m, 3H), 2.20-2.48 (m, 6H), 2.83 (s, 9H), 3.00 (bs, 3H), 3.27 (t, J=7.4 Hz, 2H), 3.32-3.41 (m, 2H), 3.44-3.54 (m, 2H), 3.91-4.14 (m, 3H), 4.20-4.40 (m, 2H), 5.25-5.34 (m, 1H), 5.46 (dd, J=7.4 Hz, 1H);

MS (ESI) m/z 1213 [M+H]$^+$

Step 4: Preparation of Compound 21

The compound 11c (40 mg, 32.96 μmol) was added to 70% trifluoroacetic acid/dichloromethane (1 mL), followed by stirring for 5 hours. After dropping the reaction mixture in diethyl ether (40 mL) to make a precipitate, it was separated using a centrifuge. Then, the compound 21 (15 mg, 55%) was obtained by high performance liquid chromatography (HPLC).

$^1$H NMR (400 MHz, D$_2$O) δ 1.29-1.38 (m, 2H), 1.46 (bs, 1H), 1.54-1.62 (m, 2H), 1.63-1.70 (m, 1H), 1.75-1.82 (m, 1H), 1.83-1.93 (m, 1H), 2.05-2.13 (m, 1H), 2.42 (t, J=7.2 Hz, 2H), 2.70-3.89 (br, 22H), 3.94 (s, 1H), 3.99 (s, 1H), 4.04 (s, 2H), 4.07-4.12 (1H), 4.12-4.15 (m, 2H), 4.18 (t, J=4.4 Hz, 2H)

MS (ESI) m/z 821 [M+H]$^+$

<Example 9> Preparation of Compound 2m

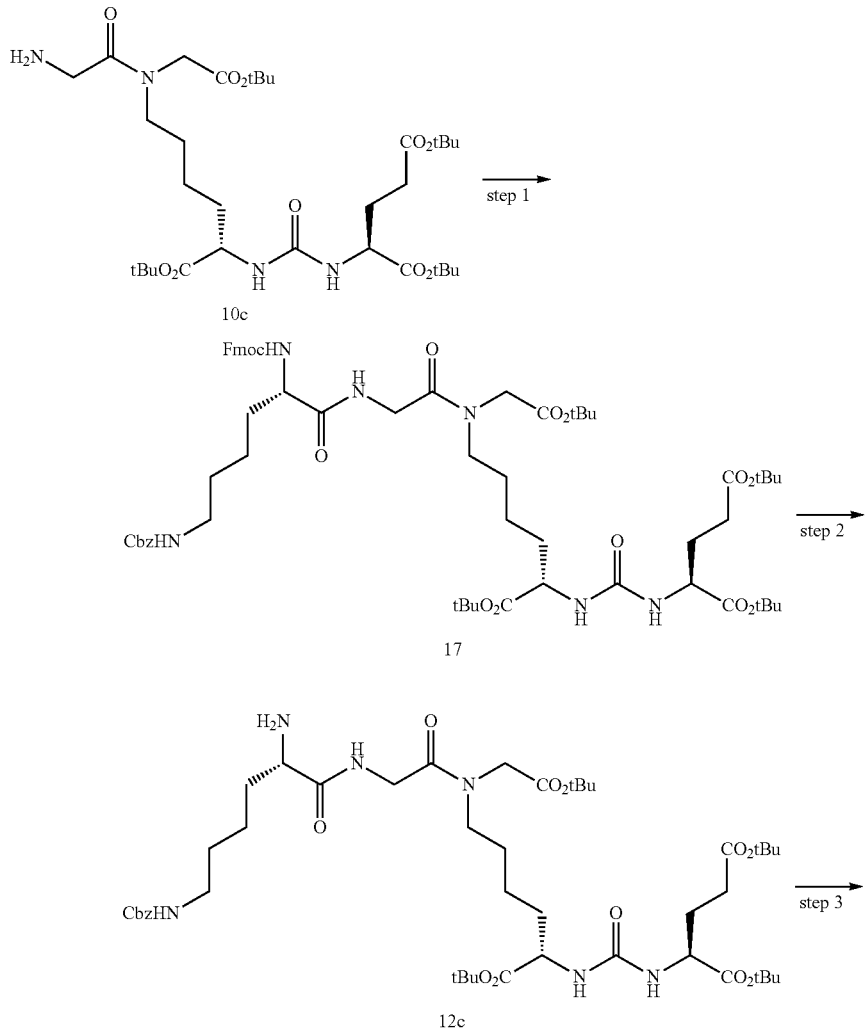

-continued
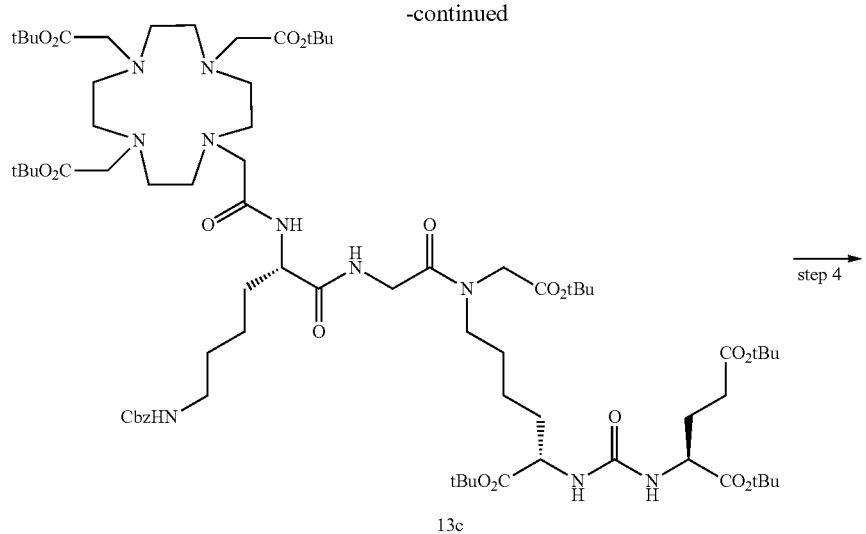
13c
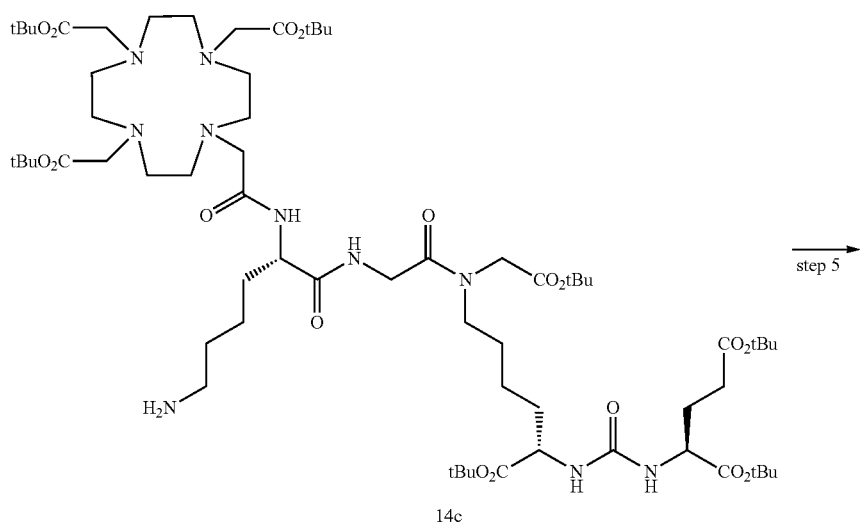
14c
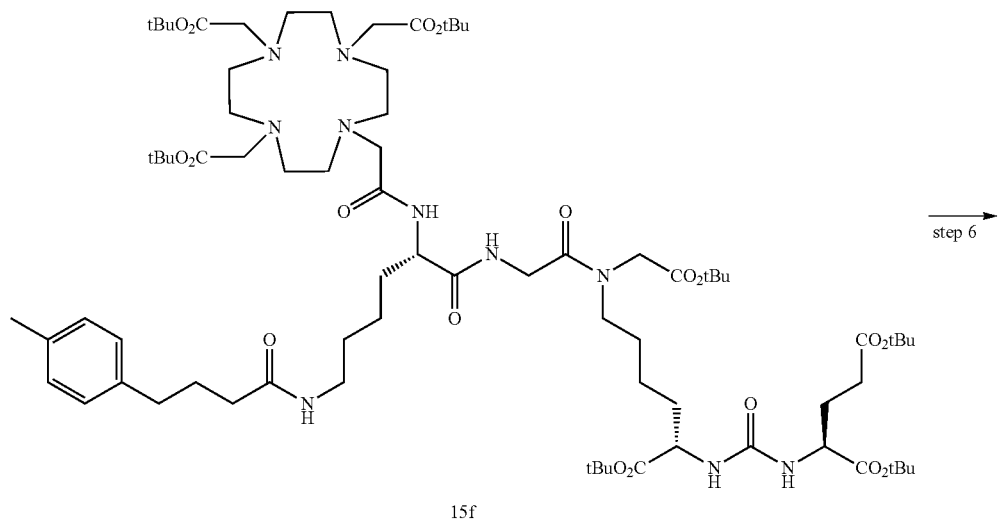
15f

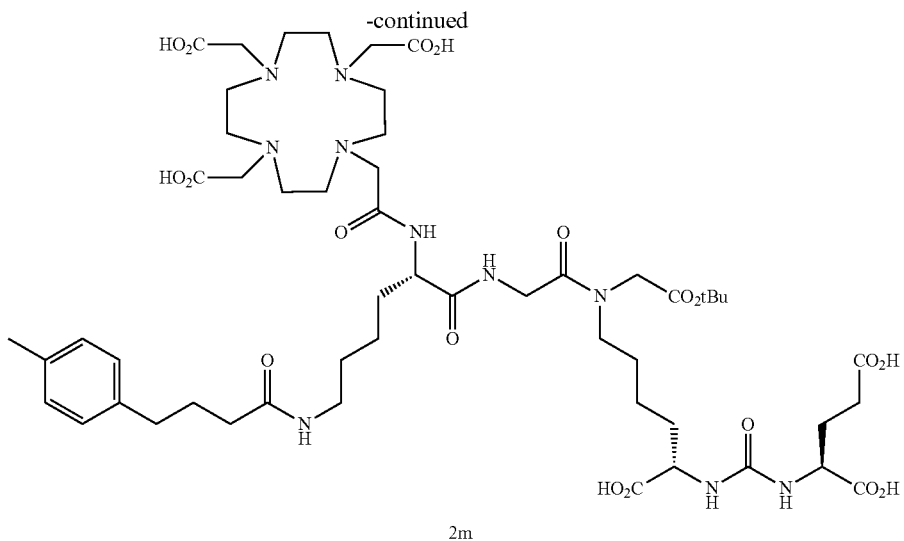

2m

Step 1: Preparation of Compound 17

Fmoc-Lys (Z)—OH (183 mg, 0.36 mmol) was dissolved in dichloromethane (1 mL), to which hydroxybenzotriazole (HOBt, 62 mg, 0.46 mmol), TBTU (146 mg, 0.46 mmol) and diisopropylethylamine (106 μL, 0.61 mmol) were added, followed by stirring at room temperature for 10 minutes. The compound 10c (0.20 g, 0.30 mmol) dissolved in dichloromethane (1 mL) was added thereto, followed by stirring for 4 hours. The reaction was terminated by adding water (10 mL), and the organic compound was extracted using dichloromethane (10 mL×3). The reactant was dried over anhydrous sodium sulfate, concentrated under reduced pressure, and the concentrate was separated by column chromatography (5% methanol/dichloromethane) to give the compound 17 (268 mg, 77%) as a white solid.

$^1$H NMR (400 MHz, CDCl$_3$) δ 1.19-1.29 (m, 2H), 1.37-1.46 (m, 36H), 1.49-1.55 (m, 2H), 1.57-1.63 (m, 2H), 1.68 (s, 3H), 1.77-1.84 (m, 2H), 2.00-2.10 (m, 2H), 2.22-2.35 (m, 2H), 3.10-3.23 (m, 3H), 3.79-3.99 (m, 3H), 4.13 (s, 1H), 4.18-4.26 (m, 2H), 4.32-4.42 (m, 3H), 5.05 (s, 2H), 5.37-5.87 (m, 3H), 7.02 (d, J=22 Hz, 1H), 7.23-7.40 (m, 8H), 7.54-7.60 (m, 2H), 7.73 (q, J=6.1 Hz, 2H)

MS (ESI) m/z 1165 [M+Na]$^+$

Step 2: Preparation of Compound 12c

The compound 17 (250 mg, 0.22 mmol) was dissolved in CH$_2$Cl$_2$ (1 mL), to which piperidine (64.80 μL, 0.66 mmol) was added, followed by stirring at room temperature for 5 hours. After eliminating the solvent from the reaction mixture under reduced pressure, the concentrate was subjected to column chromatography to give the compound 12c (170 mg, 84%) as a colorless liquid.

$^1$H NMR (400 MHz, CDCl$_3$) δ 1.24-1.36 (m, 2H), 1.45 (s, 9H), 1.47 (s, 9H), 1.48 (s, 18H), 1.52-1.59 (m, 4H), 1.71 (s, 4H), 1.77-1.89 (m, 3H), 2.04-2.13 (m, 1H), 2.25-2.39 (m, 2H), 3.15-3.25 (m, 2H), 3.26-3.34 (m, 1H), 3.85-4.05 (m, 2H), 4.12-4.20 (m, 2H), 4.26-4.41 (m, 2H), 5.06-5.16 (m, 3H), 5.51 (ddd, J=49.3, 29.4, 8.1 Hz, 2H), 7.37 (d, J=4.4 Hz, 4H), 7.92 (s, 1H);

MS (ESI) m/z 922 [M+H]$^+$

Step 3: Preparation of Compound 13c

DOTA-tris(tBu) ester (99 mg, 0.119 mmol) was dissolved in dichloromethane (0.5 mL), to which hydroxybenzotriazole (HOBt, 23 mg, 0.261 mmol), TBTU (56 mg, 0.261 mmol) and diisopropylethylamine (30 μL, 347 μmol) were added, followed by stirring at room temperature for 10 minutes. The compound 12c (160 mg, 0.174 mmol) dissolved in dichloromethane (1.6 mL) was added thereto, followed by stirring for 1 hour. The reaction was terminated by adding water (10 mL), and the organic compound was extracted using dichloromethane (10 mL×3). The reactant was dried over anhydrous sodium sulfate, concentrated under reduced pressure, and the concentrate was separated by column chromatography (5% methanol/dichloromethane) to give the compound 13c (180 mg, 72%) as a colorless liquid.

$^1$H NMR (400 MHz, CDCl$_3$) δ 1.28-1.33 (m, 3H), 1.45 (s, 9H), 1.46 (s, 9H), 1.47 (s, 9H), 1.47 (s, 9H), 1.48 (s, 18H), 1.49 (s, 9H), 1.79 (s, 8H), 2.04-2.15 (m, 5H), 2.25-2.41 (m, 5H), 2.59 (bs, 3H), 2.83 (bs, 4H), 2.95 (bs, 3H), 3.18-3.28 (m, 5H), 3.47 (bs, 4H), 3.92 (dd, J=44.0, 18.4 Hz, 2H), 4.04-4.24 (m, 2H), 4.33-4.39 (m, 3H), 5.10 (d, J=3.2 Hz, 2H), 7.15 (d, J=18.4 Hz, 1H), 7.30-7.37 (m, 4H), 7.46 (s, 1H);

MS (EST) m/z 1498 [M+Na]$^+$

Step 4: Preparation of Compound 14c

Palladium (10% Palladium on carbon, 6 mg, 5.8 μmol) was put in a round bottom flask, which was closed with a septum, and filled with hydrogen gas in vacuo. The compound 13c (170 mg, 115 μmol) dissolved in methanol (2 mL) was loaded in a reaction vessel, followed by stirring at room temperature for 15 hours. The reactant was filtered with celite, concentrated under reduced pressure, and the concentrate was separated by NH-silica gel column chromatography (0-1% methanol/dichloromethane) to give the compound 14c (117 mg, 76%) as a colorless liquid.

$^1$H NMR (400 MHz, CDCl$_3$) δ 1.14-1.28 (m, 3H), 1.36 (s, 18H), 1.41 (s, 18H), 1.44 (s, 27H), 1.53-1.62 (m, 4H), 1.68-1.83 (m, 5H), 1.97-2.09 (m, 4H), 2.10-2.37 (m, 7H), 2.40-2.69 (m, 6H), 2.70-3.10 (m, 7H), 3.15-3.26 (m, 2H), 3.31-3.65 (m, 4H), 3.78-3.95 (m, 2H), 4.01-4.13 (m, 2H), 4.21-4.35 (m, 3H), 5.37-5.55 (m, 2H), 7.17 (d, J=28.8 Hz, 1H), 7.52 (bs, 1H);

MS (ESI) m/z 1365 [M+Na]$^+$

Step 5: Preparation of Compound 15f 4-(p-Tolyl)butyric acid (16 mg, 89 μmol) was dissolved in dichloromethane (1 mL), to which hydroxybenzotriazole (HOBt, 15 mg, 112 μmol), TBTU (36 mg, 112 μmol) and DIEA (26 μL, 149 μmol) were added, followed by stirring at room temperature for 10 minutes. The compound 14c (100 mg, 75 µmol) dissolved in dichloromethane (2 mL) was added thereto, followed by stirring for 1.5 hours. The reaction was terminated by adding water (10 mL), and the organic compound was extracted using dichloromethane (10 mL×3). The reactant was dried over anhydrous sodium sulfate, concentrated under reduced pressure, and the concentrate was separated by column chromatography to give the compound 15f (69 mg, 86%) as a colorless liquid.

$^1$H NMR (400 MHz, CDCl$_3$) δ 1.26-1.32 (m, 2H), 1.35-1.40 (m, 27H), 1.42-1.47 (m, 36H), 1.52-1.59 (m, 4H), 1.79-1.96 (m, 6H), 2.00-2.08 (m, 4H), 2.10-2.20 (m, 2H), 2.21-2.41 (m, 14H), 2.54-2.62 (m, 6H), 2.78 (s, 3H), 2.83-2.95 (m, 2H), 3.20 (s, 3H), 3.28-3.62 (m, 4H), 3.73-3.88 (m, 2H), 3.93-4.03 (m, 2H), 4.13-4.25 (m, 2H), 4.27-4.33 (m, 2H), 5.35-5.61 (m, 2H), 7.05 (d, J=1.6 Hz, 4H)

MS (ESI) m/z 1524 [M+Na]$^+$

Step 6: Preparation of Compound 2m

The compound 15f (86 mg, 57 µmol) obtained in step 5 above was added to 70% trifluoroacetic acid/dichloromethane (1 mL), followed by stirring for 6 hours. After dropping the reaction mixture in diethyl ether (40 mL) to make a precipitate, it was separated using a centrifuge. The mixture was separated by high performance liquid chromatography (HPLC) and dried using a lyophilizer to give the compound 2m (44 mg, 69%) as a white solid.

$^1$H NMR (400 MHz, D$_2$O) δ 1.36-1.41 (m, 4H), 1.46-1.53 (m, 3H), 1.54-1.59 (m, 2H), 1.66-1.75 (m, 2H), 1.77-1.88 (m, 4H), 1.90-1.99 (m, 1H), 2.10-2.16 (m, 1H), 2.21 (t, J=7.2 Hz, 2H), 2.27 (s, 3H), 2.48 (t, J=7.6 Hz, 2H), 2.53 (t, J=7.6 Hz, 2H), 2.93-3.56 (br, 20H), 3.71 (bs, 3H), 3.87 (s, 1H), 3.91 (s, 1H), 3.98 (s, 1H), 4.04 (t, J=8.6 Hz, 3H), 4.12 (s, 1H), 4.13-4.19 (m, 2H), 4.22-4.26 (m, 1H), 4.30 (bs, 1H), 7.15 (q, J=7.9 Hz, 4H);

MS (ESI) m/z 1109 [M−H]$^−$

<Example 10> Preparation of Compound 19

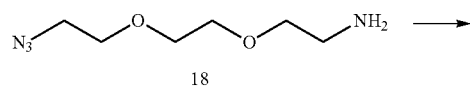

18

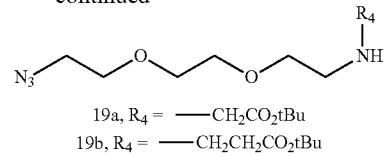

19a, R$_4$ = —CH$_2$CO$_2$tBu
19b, R$_4$ = —CH$_2$CH$_2$CO$_2$tBu

Preparation of Compound 19a

The compound 18 (500 mg, 2.87 mmol) was dissolved in dichloromethane (5 mL) and cooled to 0° C., to which triethylamine (0.6 mL, 4.31 mmol) was added. Tert-butyl bromoacetate (620 mg, 3.16 mmol) dissolved in dichloromethane (5 mL) was slowly added thereto, followed by stirring at room temperature for 18 hours. The reaction was terminated by adding water (10 mL), and the organic compound was extracted using dichloromethane (10 mL×2). The reactant was dried over anhydrous sodium sulfate, concentrated under reduced pressure, and the concentrate was separated by column chromatography (2% methanol/dichloromethane) to give the compound 19a (0.46 g, 55%).

$^1$H NMR (400 MHz, CDCl$_3$) δ 1.45 (s, 9H), 2.78 (t, J=4.8 Hz, 2H), 3.31 (s, 2H), 3.38 (t, J=5.6 Hz, 2H), 3.68-3.59 (m, 9H);

$^{13}$C NMR (100 MHz, CDCl$_3$) δ 28.1, 48.7, 50.6, 51.7, 56.6, 76.7, 77.0, 77.3, 81.0, 171.5;

MS (ESI) m/z 289 [M+H]$^+$

Preparation of Compound 19b

The compound 18 (300 mg, 1.72 mmol) was dissolved in ethanol (10 mL) and cooled to 0° C., to which tert-butyl acrylate (220 mg, 1.72 mmol) was slowly added. After gradually raising the temperature of the mixture to room temperature, the mixture was stirred for 18 hours. The organic solvent was eliminated under reduced pressure, and the concentrate was separated by column chromatography (5% methanol/dichloromethane) to give the compound 19b (380 mg, 73%).

$^1$H NMR (400 MHz, CDCl$_3$) δ 1.43 (s, 9H), 2.42 (t, J=6.4 Hz, 2H), 2.79 (t, J=5.6 Hz, 2H), 2.85 (t, J=6.4 Hz, 2H), 3.38 (t, J=4.8 Hz, 2H), 3.58 (t, J=5.2 Hz, 2H), 3.62-3.68 (m, 6H);

$^{13}$C NMR (100 MHz, CDCl$_3$) δ 28.1, 35.9, 45.2, 49.1, 50.7, 76.7, 77.0, 77.3, 80.4, 172.0;

MS (ESI) m/z 303 [M+H]$^+$

<Example 11> Preparation of Compounds 2n and 2o

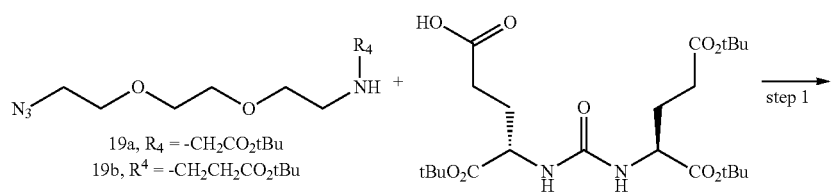

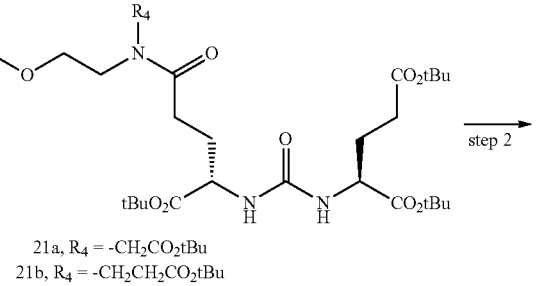

21a, R$_4$ = -CH$_2$CO$_2$tBu
21b, R$_4$ = -CH$_2$CH$_2$CO$_2$tBu

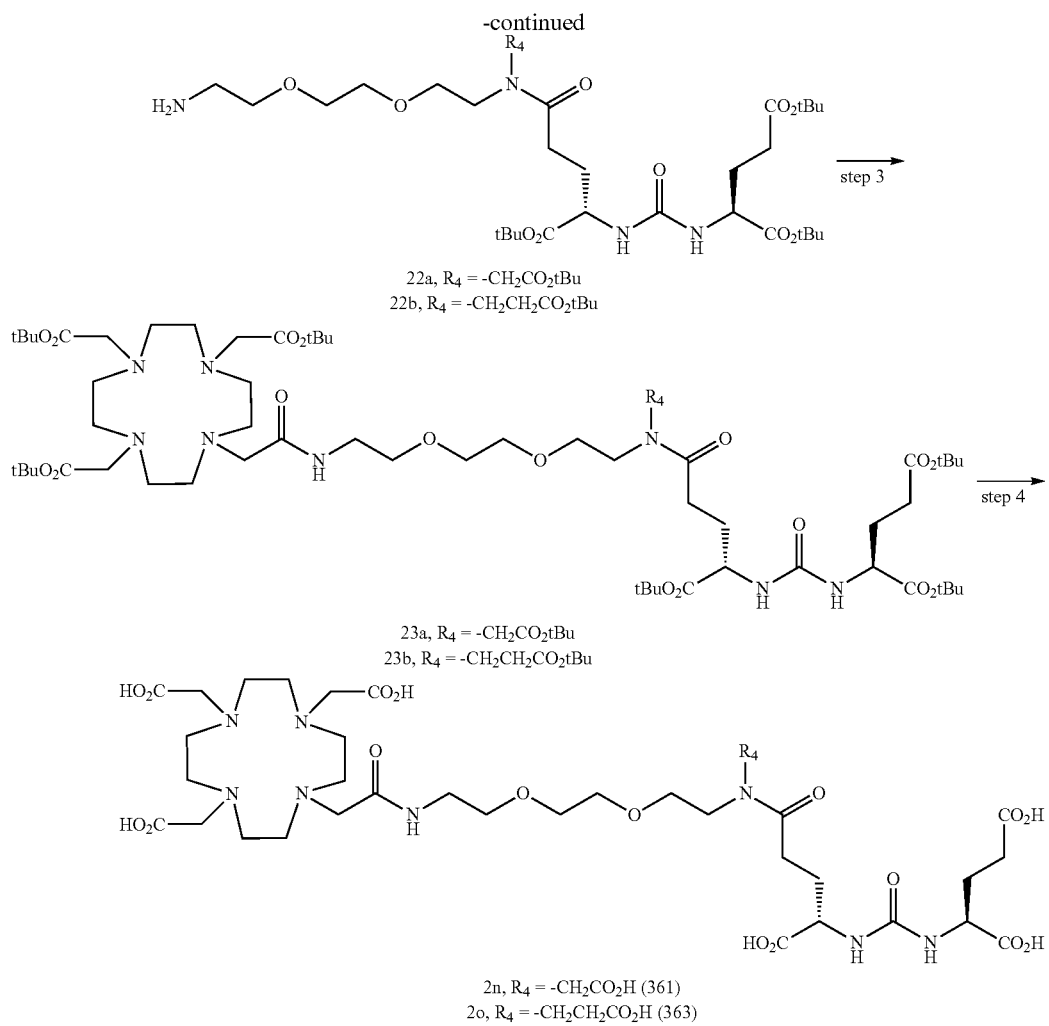

22a, $R_4$ = -$CH_2CO_2tBu$
22b, $R_4$ = -$CH_2CH_2CO_2tBu$

23a, $R_4$ = -$CH_2CO_2tBu$
23b, $R_4$ = -$CH_2CH_2CO_2tBu$

2n, $R_4$ = -$CH_2CO_2H$ (361)
2o, $R_4$ = -$CH_2CH_2CO_2H$ (363)

Step 1: Preparation of Compound 21a

The compound 20 (180 mg, 0.36 mmol) was dissolved in dichloromethane (5 mL) and cooled to 0° C., to which N,N'-dicyclohexylcarbodiimide (DCC, 83 mg, 0.40 mmol) and the compound 19a (110 mg, 0.36 mmol) were added, followed by stirring at room temperature for 1 hour. The organic layer was filtered several times, and the solvent was eliminated under reduced pressure. The concentrate was separated by column chromatography (5% methanol/dichloromethane) to give the compound 21a (250 mg, 91%).

$^1$H NMR (400 MHz, CDCl$_3$) δ 1.43 (s, 9H), 1.44 (s, 9H), 1.45 (s, 9H), 1.46 (s, 9H), 1.79-1.86 (m, 1H), 2.01-2.20 (m, 3H), 2.26-2.36 (m, 3H), 2.44-2.55 (m, 1H), 2.77 (br, 1H), 3.40 (t, J=6.4 Hz, 2H), 3.56-3.74 (m, 9H), 4.03 (dd, J=44.0, 17.2 Hz, 2H), 4.22-4.35 (m, 2H);

MS (ESI) m/z 759 [M+H]$^+$

Step 1: Preparation of Compound 21b

The compound 21b (275 mg, 87%) was obtained by the same manner as described in the preparation of the compound 21a except that the compound 20 (200 mg, 0.41 mmol), N,N'-dicyclohexylcarbodiimide (DCC, 102 mg, 0.49 mmol) and the compound 19b (200 mg, 0.41 mmol) were used.

MS (ESI) m/z 773 [M+H]$^+$

Step 2: Preparation of Compound 22a

The compound 21a (200 mg, 0.26 mmol) was dissolved in methanol (8 mL), to which palladium (10% Palladium on carbon, 13 mg, 13 μmol) was added. The reaction flask was filled with hydrogen gas, followed by stirring at room temperature for 1 hour. After passing the reaction product through celite, the solvent was eliminated under reduced pressure, and the concentrate was separated by column chromatography (8% methanol/dichloromethane) to give the compound 22a (120 mg, 63%).

$^1$H NMR (400 MHz, methanol-d$_4$) δ 1.45 (s, 9H), 1.47-1.49 (m, 27H), 1.76-1.94 (m, 2H), 2.01-2.13 (m, 2H), 2.27-2.39 (m, 3H), 2.55-2.60 (m, 2H), 2.79-2.81 (m, 2H), 3.35 (s, 1H), 3.52 (t, J=5.2 Hz, 2H), 3.55-3.65 (m, 8H), 4.04 (dd, J=17.6, 4.8 Hz, 1H), 4.14-4.22 (m, 3H);

MS (ESI) m/z 733 [M+H]$^+$

Step 2: Preparation of Compound 22b

The compound 22b (210 mg, 90%) was obtained by the same manner as described in the preparation of the compound 22a except that the compound 21b (240 mg, 0.32 mmol) and palladium (10% Palladium on carbon, 17 mg, 16 μmol) were used.

$^1$H NMR (400 MHz, methanol-d$_4$) δ 1.45 (s, 18H), 1.48 (s, 18H), 1.59-1.63 (m, 1H), 1.68-1.75 (m, 2H), 1.79-1.91 (m, 4H), 2.03-2.14 (m, 2H), 2.30-2.36 (m, 2H), 2.48-2.62

(m, 3H), 2.80-2.82 (m, 2H), 3.43-3.70 (m, 12H), 4.14-4.20 (m, 2H);

MS (ESI) m/z 747 [M+H]+

Step 3: Preparation of Compound 23a

DOTA-tris(tBu) ester (38 mg, 65 μmol) was dissolved in dichloromethane (7 mL), to which hydroxybenzotriazole (HOBt, 110 mg, 82 μmol), TBTU (26 mg, 82 μmol) and diisopropylethylamine (19 μL, 0.11 mmol) were added, followed by stirring for 10 minutes. The compound 22a (40 mg, 55 μmol) dissolved in dichloromethane (3 mL) was added thereto, followed by stirring for 1 hour. The reaction was terminated by adding water (10 mL), and the organic compound was extracted using dichloromethane (10 mL×2). The reactant was dried over anhydrous sodium sulfate, concentrated under reduced pressure, and the concentrate was separated by column chromatography (5% methanol/dichloromethane) to give the compound 23a (60 mg, 70%) as a white solid.

$^1$H NMR (400 MHz, methanol-$d_4$) δ 1.40-1.57 (m, 63H), 1.76-2.87 (m, 26H), 3.36-3.63 (m, 17H), 3.74 (s, 1H), 4.04 (d, J=8.0 Hz, 2H), 4.14-4.24 (m, 3H), 6.34-6.38 (m, 1H);

MS (ESI) m/z 1288 [M+H]+

Step 3: Preparation of Compound 23b

The compound 23b (60 mg, 68%) was obtained by the same manner as described in the preparation of the compound 23a except that DOTA-tris(tBu) ester (46 mg, 80 μmol), hydroxybenzotriazole (HOBt, 14 mg, 0.10 mmol), TBTU (32 mg, 0.10 mmol), diisopropylethylamine (24 μL, 0.13 mmol) and the compound 22b (50 mg, 67 μmol) were used.

$^1$H NMR (400 MHz, methanol-$d_4$) δ 1.09-1.24 (m, 12H), 1.29-1.43 (m, 10H), 1.45-1.53 (m, 41H), 1.57-1.63 (m, 4H), 1.66-1.76 (m, 7H), 1.80-1.91 (m, 8H), 2.03-2.12 (m, 2H), 2.25-2.37 (m, 2H), 2.44-2.64 (m, 4H), 2.82 (s, 9H), 3.35-3.49 (m, 5H), 3.52-3.69 (m, 7H), 4.14-4.22 (m, 2H);

MS (ESI) m/z 1302 [M+H]+

Step 4: Preparation of Compound 2n

The compound 23a (45 mg, 35 μmol) was added to 70% trifluoroacetic acid/dichloromethane (1 mL), followed by stirring for 7 hours. After dropping the reaction mixture in diethyl ether (20 mL) to make a precipitate, it was separated using a centrifuge. The mixture was separated by high performance liquid chromatography (HPLC) and dried using a lyophilizer to give the compound 2n (22 mg, 70%) as a solid.

$^1$H NMR (400 MHz, $D_2O$) δ 1.93-2.02 (m, 2H), 2.14-2.22 (m, 2H), 2.45-2.54 (m, 3H), 2.63-2.68 (m, 2H), 2.88-3.56 (m, 18H), 3.57-3.72 (m, 11H), 3.73-3.85 (m, 3H), 3.86-4.10 (m, 3H), 4.16 (s, 1H), 4.21-4.31 (m, 3H);

MS (ESI) m/z 895 [M+H]+

Step 4: Preparation of Compound 2o

The compound 2o (17 mg, 48%) was obtained by the same manner as described in the preparation of the compound 2n except that the compound 23b (50 mg, 38 μmol) and 70% trifluoroacetic acid/dichloromethane (1 mL) were used.

$^1$H NMR (400 MHz, $D_2O$) δ 1.92-2.03 (m, 2H), 2.15-2.25 (m, 2H), 2.48-2.68 (m, 5H), 2.71-2.75 (m, 1H), 2.92-3.53 (m, 18H), 3.55-3.86 (m, 17H), 3.87-4.17 (m, 3H), 4.22-4.31 (m, 2H);

MS (ESI) m/z 909 [M+H]+

<Example 12> Preparation of Compound 2p

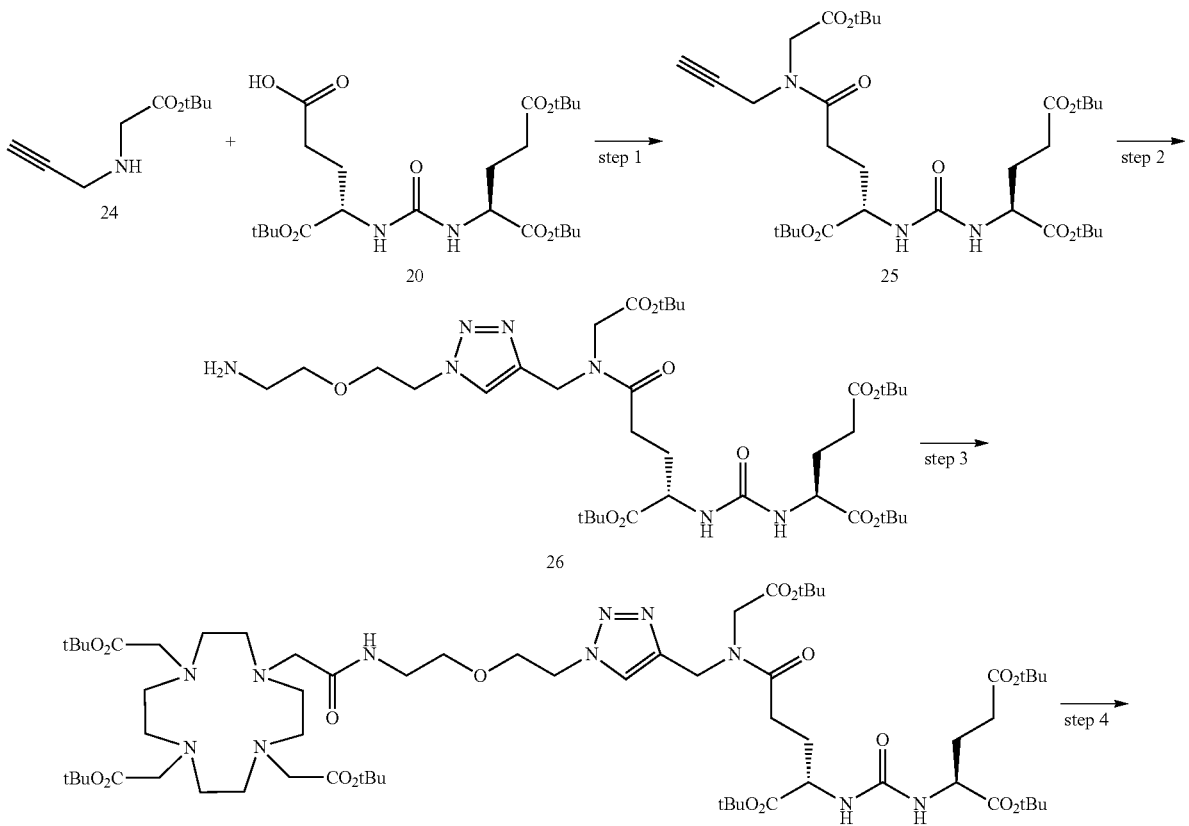

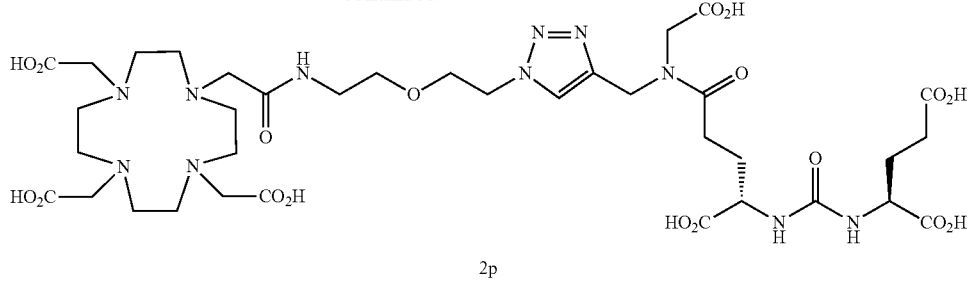

2p

Step 1: Preparation of Compound 25

The compound 20 (500 mg, 1.02 mmol) was dissolved in dichloromethane (10 mL) and cooled to 0° C., to which N,N'-dicyclohexylcarbodiimide (DCC, 230 mg, 1.12 mmol) and the compound 24 (170 mg, 1.02 mmol) were added, followed by stirring at room temperature for 1 hour. The organic layer was filtered several times, and the solvent was eliminated under reduced pressure. The concentrate was separated by column chromatography (30% ethylacetate/n-hexane) to give the compound 25 (450 mg, 69%).

$^1$H NMR (400 MHz, CDCl$_3$) δ 1.37-1.50 (m, 36H), 1.81-1.90 (m, 1H), 1.96-2.25 (m, 4H), 2.28-2.39 (m, 3H), 2.51-2.56 (m, 1H), 4.01-4.10 (m, 2H), 4.14-4.21 (m, 2H), 4.24-4.36 (m, 3H), 5.51 (br, 1H), 5.75 (br, 1H);

MS (ESI) m/z 774 [M+H]$^+$

Step 2: Preparation of Compound 26

The compound 25 (350 mg, 0.55 mmol) and 2-aminoethyl 2'-azidoethyl ether (110 mg, 0.82 mmol) were dissolved in ethanol (10 mL), to which 1 M CuSO$_4$ (0.11 mL, 0.11 mmol) and 2 M sodium ascorbate (0.082 mL, 0.16 mmol) were added, followed by stirring for 1 hour. The reactant was filtered and the solvent was eliminated under reduced pressure. The concentrate was separated by NH silica gel column chromatography (3% methanol/dichloromethane) to give the compound 26 (250 mg, 59%).

$^1$H NMR (400 MHz, methanol-d$_4$) δ 1.41-1.51 (m, 37H), 1.78-1.90 (m, 2H), 2.03-2.16 (m, 2H), 2.29-2.42 (m, 3H), 2.67-2.71 (m, 1H), 3.12 (q, J=5.2 Hz, 2H), 3.65-3.70 (m, 2H), 3.88-3.94 (m, 2H), 4.01 (d, J=6.0 Hz, 1H), 4.16-4.22 (m, 3H), 4.52-4.64 (m, 3H), 4.69-4.75 (m, 1H), 7.95 (s, 0.6H), 8.07 (s, 0.5H);

MS (ESI) m/z 770 [M+H]$^+$

Step 3: Preparation of Compound 27

DOTA-tris(tBu) ester (36 mg, 62 μmol) was dissolved in dichloromethane (5 mL), to which hydroxybenzotriazole (DCC, 11 mg, 78 μmol), TBTU (25 mg, 78 μmol) and diisopropylethylamine (18 μL, 0.10 mmol) were added, followed by stirring at room temperature for 10 minutes. The compound 26 (40 mg, 52 μmol) dissolved in dichloromethane (1 mL) was added thereto, followed by stirring for 1 hour. The reaction was terminated by adding water (10 mL), and the organic compound was extracted using dichloromethane (10 mL×2). The reactant was dried over anhydrous sodium sulfate, concentrated under reduced pressure, and the concentrate was separated by column chromatography (3% methanol/dichloromethane) to give the compound 27 (50 mg, 72%).

$^1$H NMR (400 MHz, methanol-d$_4$) δ 1.40-1.52 (m, 63H), 1.55-1.66 (m, 1H), 1.76-1.97 (m, 4H), 2.02-2.28 (m, 9H), 2.29-2.48 (m, 8H), 2.68-2.72 (m, 3H), 3.35-3.41 (m, 4H), 3.48-3.71 (m, 4H), 3.81-3.87 (m, 3H), 3.94-4.08 (m, 1H), 4.13-4.23 (m, 4H), 4.52-4.59 (m, 3H), 4.64-4.75 (m, 2H), 7.92 (s, 0.6H), 8.05 (s, 0.4H);

MS (ESI) m/z 1325 [M+H]$^+$

Step 4: Preparation of Compound 2p

The compound 27 (43 mg, 32 μmol) was added to 70% trifluoroacetic acid/dichloromethane (1 mL), followed by stirring for 7 hours. After dropping the reaction mixture in diethyl ether (20 mL) to make a precipitate, it was separated using a centrifuge. The mixture was separated by high performance liquid chromatography (HPLC) and dried using a lyophilizer to give the compound 2p (22 mg, 73%) as a solid.

$^1$H NMR (400 MHz, D$_2$O) δ 1.90-2.03 (m, 2H), 2.12-2.23 (m, 2H), 2.43-2.53 (m, 3H), 2.72-2.78 (m, 1H), 2.99-3.46 (m, 16H), 3.52-3.59 (m, 3H), 3.62-4.10 (m, 9H), 4.14 (s, 1H), 4.19-4.35 (m, 3H), 4.57-4.63 (m, 2H), 4.65-4.74 (m, 2H), 4.77 (s, 2H), 7.95 (s, 0.4H), 8.04 (s, 0.6H);

MS (ESI) m/z 932 [M+H]$^+$

<Example 13> Preparation of Ga-1

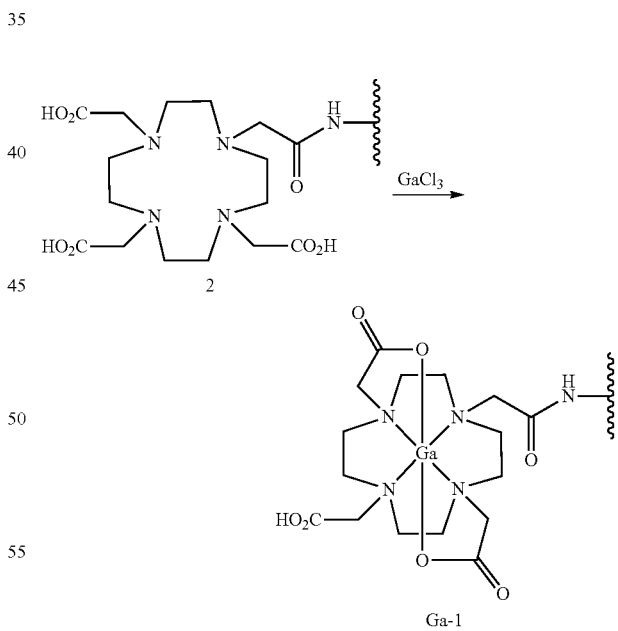

Ga-1

Preparation of Compound Ga-1a

The compound 2a (10 mg, 11 μmol) was dissolved in water (0.6 mL), to which gallium trichloride (19 mg, 0.11 mmol) dissolved in water (0.6 mL) was added, followed by stirring at 70° C. for 1 hour. The reaction solution was filtered. The filtrate was separated by high performance liquid chromatography (HPLC) and dried using a lyophilizer to give the compound Ga-1a (6 mg, 56%) as a solid.

¹H NMR (400 MHz, D₂O) δ 1.34-1.51 (m, 4H), 1.64-1.73 (m, 1H), 1.77-1.86 (m, 1H), 1.91-2.00 (m, 1H), 2.12-2.20 (m, 1H), 2.50 (t, J=7.2 Hz, 2H), 3.10 (t, J=6.8 Hz, 2H), 3.31-3.43 (m, 10H), 3.52-3.57 (m, 6H), 3.65 (s, 2H), 3.78 (s, 2H), 3.84-3.94 (m, 8H), 4.00-4.03 (m, 2H), 4.16 (dd, J=14.0, 5.2 Hz, 1H), 4.24 dd, J=14.0, 5.2 Hz, 1H), 4.38 (s, 2H), 4.57 (t, J=4.8 Hz, 2H), 7.88 (s, 1H);

MS (ESI) m/z 984 [M+H]⁺

Preparation of Compound Ga-1b

The compound 2b (19 mg, 19 μmol) was dissolved in water (0.8 mL), to which gallium trichloride (33 mg, 0.19 mmol) dissolved in water (0.8 mL) was added, followed by stirring at 70° C. for 1 hour. The reaction solution was filtered. The filtrate was separated by high performance liquid chromatography (HPLC) and dried using a lyophilizer to give the compound Ga-1b (13 mg, 64%) as a solid.

¹H NMR (400 MHz, D₂O) δ 1.28-1.42 (m, 3H), 1.50-1.57 (m, 2H), 1.65-1.73 (m, 1H), 1.77-1.86 (m, 1H), 1.89-1.99 (m, 1H), 2.10-2.20 (m, 1H), 2.48 (t, J=7.2 Hz, 2H), 3.27-3.42 (m, 11H), 3.49-3.57 (m, 6H), 3.67 (s, 2H), 3.78 (s, 2H), 3.83-3.92 (m, 8H), 4.00-4.03 (m, 2H), 4.15 (dd, J=14.0, 4.8 Hz, 1H), 4.24 ((dd, J=14.0, 4.8 Hz, 1H), 4.58 (t, J=4.8 Hz, 2H), 5.19 (s, 2H), 7.62 (d, J=7.6 Hz, 2H), 8.01 (s, 1H), 8.42 (d, J=7.6 Hz, 2H);

MS (ESI) m/z 1061 [M+H]⁺

Preparation of Compound Ga-1c

The compound 2c (10 mg, 10 μmol) was dissolved in water (1 mL), to which gallium trichloride (18 mg, 100 μmol) dissolved in water (1 mL) was added, followed by stirring at 70° C. for 1 hour. The reaction solution was filtered. The filtrate was separated by high performance liquid chromatography (HPLC) and dried using a lyophilizer to give the compound Ga-1c (6 mg, 58%) as a solid.

¹H NMR (400 MHz, D₂O) δ 1.28-1.42 (m, 2H), 1.44-1.62 (m, 2H), 1.64-1.77 (m, 1H), 1.78-1.90 (m, 1H), 1.93-2.23 (m, 1H), 2.50-2.54 (m, 2H), 2.72-2.75 (m, 0.5H), 2.87-2.90 (m, 1.5H), 3.01-3.07 (m, 2H), 3.36-3.44 (m, 12H), 3.54-3.59 (m, 6H), 3.69 (s, 2H), 3.77 (s, 2H), 3.85-3.94 (m, 8H), 4.00-4.12 (m, 4H), 4.16-4.29 (m, 3H), 4.57-4.60 (m, 2H), 7.81 (s, 1H);

MS (ESI) m/z 1041 [M+H]⁺

Preparation of Compound Ga-1d

The compound 2d (6 mg, 6 μmol) was dissolved in water (0.8 mL), to which gallium trichloride (14 mg, 80 μmol) dissolved in water (0.8 mL) was added, followed by stirring at 70° C. for 1 hour. The reaction solution was filtered. The filtrate was separated by high performance liquid chromatography (HPLC) and dried using a lyophilizer to give the compound Ga-1d (4 mg, 62%) as a solid.

¹H NMR (400 MHz, D₂O) δ 1.26-1.43 (m, 2H), 1.44-1.60 (m, 2H), 1.66-1.78 (m, 1H), 1.79-1.91 (m, 1H), 1.94-1.20 (m, 1H), 2.15-2.24 (m, 1H), 2.48-2.67 (m, 4H), 2.79-2.88 (m, 2H), 3.01-3.09 (m, 2H), 3.28-3.49 (m, 11H), 3.52-3.65 (m, 8H), 3.70 (s, 2H), 3.79 (s, 2H), 3.84-3.99 (m, 7H), 4.05 (d, J=10.8 Hz, 2H), 4.18-4.29 (m, 2H), 4.60 (t, J=5.2 Hz, 2H), 7.82 (s, 0.6H), 7.84 (s, 0.4H);

MS (ESI) m/z 1055 [M+H]⁺

Preparation of Compound Ga-1e

The compound 2e (16 mg, 18 μmol) was dissolved in distilled water (0.5 mL), to which gallium trichloride (16 mg, 91 μmol) was added, followed by stirring at 70° C. for 1 hour. The reaction solution was filtered. The filtrate was separated by high performance liquid chromatography (HPLC) and dried using a lyophilizer to give the compound Ga-1e (15 mg, 86%) as a white solid.

¹H NMR (400 MHz, D₂O) δ 1.17-1.32 (m, 2H), 1.37-1.51 (m, 2H), 1.53-1.62 (m, 1H), 1.65-1.75 (m, 1H), 1.82 (p, J=7.4 Hz, 1H), 2.01 (p, J=7.6 Hz, 1H), 2.35 (t, J=7.2 Hz, 2H), 3.00-3.30 (m, 12H), 3.36-3.41 (m, 4H), 3.47 (q, J=4.8 Hz, 2H), 3.51-3.60 (m, 6H), 3.65 (s, 2H), 3.73 (s, 4H), 3.76-3.79 (m, 2H), 3.85-3.88 (m, 2H), 3.97 (s, 2H), 4.01-4.12 (m, 3H), 4.24 (s, 2H);

MS (ESI) m/z 975 [M+H]⁺

Preparation of Compound Ga-1f

The compound 2f (3.8 mg, 3.2 μmol) synthesized in step 5 of Example 5 was dissolved in distilled water (0.5 mL), to which gallium trichloride (3.0 mg, 17 μmol) was added, followed by stirring at 70° C. for 1 hour. The reaction solution was filtered. The filtrate was separated by high performance liquid chromatography (HPLC) and dried using a lyophilizer to give the compound Ga-1f (2.7 mg, 68%) as a white solid.

¹H NMR (400 MHz, D₂O) δ 1.20-1.31 (m, 4H), 1.36-1.50 (m, 5H), 1.54-1.74 (m, 5H), 1.76-1.84 (m, 2H), 1.85-1.96 (m, 1H), 1.99-2.04 (m, 2H), 2.13 (t, J=7.4 Hz, 2H), 2.35 (t, J=7.2 Hz, 2H), 2.51 (t, J=7.0 Hz, 2H), 3.03 (t, J=6.8 Hz, 2H), 3.15-3.28 (m, 9H), 3.33-3.44 (m, 8H), 3.46-3.50 (m, 3H), 3.55-3.58 (m, 3H), 3.65-3.70 (m, 3H), 3.75-3.81 (m, 4H), 3.87 (s, 2H), 3.92-4.12 (m, 5H), 4.26 (s, 2H), 7.14-7.17 (m, 3H), 7.24-7.27 (m, 2H);

MS (ESI) m/z 1252 [M+2H]⁺, 1248 [M−2H]⁻

Preparation of Compound Ga-1g

The compound 2g (4.4 mg, 3.7 μmol) synthesized in step 5 of Example 5 was dissolved in distilled water (0.5 mL), to which gallium trichloride (4.0 mg, 23 μmol) was added, followed by stirring at 70° C. for 1 hour. The reaction solution was filtered. The filtrate was separated by high performance liquid chromatography (HPLC) and dried using a lyophilizer to give the compound Ga-1g (2.0 mg, 43%) as a white solid.

¹H NMR (400 MHz, D₂O) δ 1.12-1.28 (m, 4H), 1.32-1.37 (m, 2H), 1.40-1.48 (m, 2H), 1.49-1.62 (m, 3H), 1.64-1.70 (m, 1H), 1.73 (p, J=7.4 Hz, 2H), 1.77-1.86 (m, 1H), 1.99-2.05 (m, 1H), 2.08 (t, J=7.2 Hz, 2H), 2.15 (s, 3H), 2.36 (t, J=7.6 Hz, 2H), 2.43 (t, J=6.8 Hz, 2H), 2.96-3.03 (m, 2H), 3.04-3.28 (m, 1H), 3.30-3.47 (m, 8H), 3.84-3.91 (m, 2H), 3.92-3.40 (m, 2H), 4.03-4.08 (m, 2H), 4.09-4.14 (m, 1H), 4.23 (s, 2H), 7.01 (d, J=8.0 Hz, 2H), 7.05 (d, J=8.0 Hz, 2H);

MS (ESI) m/z 1265 [M+H]⁺, 1263 [M−H]⁻

Preparation of Compound Ga-1h

The compound 2h (6.0 mg, 4.6 μmol) synthesized in step 5 of Example 5 was dissolved in distilled water (0.5 mL), to which gallium trichloride (6.0 mg, 34.1 μmol) was added, followed by stirring at 70° C. for 1 hour. The reaction solution was filtered. The filtrate was separated by high performance liquid chromatography (HPLC) and dried using a lyophilizer to give the compound Ga-1h (5.4 mg, 86%) as a solid.

¹H NMR (400 MHz, D₂O) δ 1.21-1.30 (m, 4H), 1.33-1.38 (m, 2H), 1.40-1.51 (m, 2H), 1.54-1.75 (m, 4H), 1.82 (p, J=7.4 Hz, 2H), 1.83-1.89 (m, 1H), 2.03-2.08 (m, 1H), 2.12 (t, J=7.2 Hz, 2H), 2.39 (t, J=7.2 Hz, 1H), 2.48 (t, J=7.2 Hz, 1H), 3.00 (t, J=6.6 Hz, 2H), 3.13-3.33 (m, 11H), 3.39-3.52 (m, 8H), 3.55-3.60 (m, 6H), 3.66-3.74 (m, 3H), 3.97 (s, 2H), 4.00-4.17 (m, 3H), 4.27 (s, 2H), 6.94 (d, J=8.0 Hz, 2H), 7.59 (d, J=8.0 Hz, 2H);

MS (ESI) m/z 1375 [M+H]⁺, 1373 [M−H]⁻

Preparation of Compound Ga-1i

The compound 2i (7.0 mg, 8.1 μmol) synthesized in step 4 of Example 6 was dissolved in distilled water (0.5 mL), to which gallium trichloride (7.0 mg, 40 μmol) was added, followed by stirring at 700° C. for 1 hour. The reaction solution was filtered. The filtrate was separated by high performance liquid chromatography (HPLC) and dried using a lyophilizer to give the compound Ga-1i (6.0 mg, 79%) as a white solid.

$^1$H NMR (400 MHz, D$_2$O) δ 1.22-1.33 (m, 2H), 1.40-1.52 (m, 2H), 1.56-1.64 (m, 1H), 1.68-1.76 (m, 1H), 1.85 (p, J=7.2 Hz, 1H), 2.04 (p, J=7.2 Hz, 1H), 2.38 (t, J=7.2 Hz, 2H), 3.17-3.34 (m, 11H), 3.41-3.43 (m, 4H), 3.48-3.53 (m, 2H), 3.58 (s, 4H), 3.76 (s, 4H), 3.79 (s, 2H), 3.88-3.91 (m, 2H), 3.97 (s, 2H), 4.06-4.14 (m, 3H), 4.26 (s, 2H);

MS (ESI) m/z 933 [M+2H]$^+$, 929 [M−2H]$^-$

Preparation of Compound Ga-1j

The compound 2j (4.4 mg, 3.8 μmol) synthesized in step 5 of Example 7 was dissolved in distilled water (0.5 mL), to which gallium trichloride (4.0 mg, 23 μmol) was added, followed by stirring at 70° C. for 1 hour. The reaction solution was filtered. The filtrate was separated by high performance liquid chromatography (HPLC) and dried using a lyophilizer to give the compound Ga-1j (2.3 mg, 49%) as a white solid.

$^1$H NMR (400 MHz, D$_2$O) δ 1.20-1.30 (m, 4H), 1.34-1.50 (m, 4H), 1.56-1.66 (m, 3H), 1.69-1.80 (m, 3H), 1.83-1.87 (m, 1H), 1.97-2.08 (m, 1H), 2.11 (t, J=6.8 Hz, 2H), 2.18 (s, 3H), 2.37 (t, J=7.2 Hz, 2H), 2.42-2.48 (m, 2H), 3.02 (t, J=6.4 Hz, 2H), 3.15-3.30 (m, 9H), 3.34-3.55 (m, 11H), 3.64-3.70 (m, 3H), 3.76-3.79 (m, 4H), 3.88-3.93 (m, 4H), 4.05-4.10 (m, 3H), 4.22 (s, 2H), 7.04 (d, J=8.0 Hz, 2H), 7.08 (d, J=8.0 Hz, 2H);

MS (ESI) m/z 1121 [M+H]$^+$, 1119 [M−H]$^-$

Preparation of Compound Ga-1k

The compound 2k (2.0 mg, 1.6 μmol) synthesized in step 5 of Example 7 was dissolved in distilled water (0.5 mL), to which gallium trichloride (2.0 mg, 11 μmol) was added, followed by stirring at 70° C. for 1 hour. The reaction solution was filtered. The filtrate was separated by high performance liquid chromatography (HPLC) and dried using a lyophilizer to give the compound Ga-1k (0.6 mg, 29%) as a white solid.

MS (ESI) m/z 1332 [M+H]$^+$, 1330 [M−H]$^-$

Preparation of Compound Ga-1l

The compound 2l (7.0 mg, 8.5 μmol) was dissolved in distilled water (0.5 mL), to which gallium trichloride (4.5 mg, 25.6 μmol) was added, followed by stirring at 70° C. for 2 hours. The reaction solution was filtered. The filtrate was separated by high performance liquid chromatography (HPLC) and dried using a lyophilizer to give the compound Ga-1l (5.5 mg, 73%) as a white solid.

$^1$H NMR (400 MHz, CDCl$_3$) δ 1.24-1.40 (m, 2H), 1.42-1.51 (m, 1H), 1.54-1.62 (m, 2H), 1.63-1.94 (m, 1H), 2.06-2.14 (m, 1H), 2.44 (t, J=7.2 Hz, 2H), 3.20-3.40 (m, 9H), 3.49 (d, J=8.8 Hz, 4H), 3.72-3.86 (m, 6H), 3.87 (d, J=10.4 Hz, 2H), 3.92-4.00 (m, 3H), 4.04 (s, 2H), 4.10-4.20 (m, 4H);

MS (ESI) m/z 887 [M+H]$^+$

Preparation of Compound Ga-1m

The compound 2m (14 mg, 12.6 μmol) was dissolved in H$_2$O (0.8 mL), to which gallium trichloride (6.7 mg, 37.9 μmol) was added, followed by stirring at 70° C. for 2 hours. The reaction solution was filtered. The filtrate was separated by high performance liquid chromatography (HPLC) and dried using a lyophilizer to give the compound Ga-1m (7.1 mg, 48%) as a white solid.

$^1$H NMR (400 MHz, D$_2$O) δ 1.30-1.44 (m, 4H), 1.48-1.54 (m, 2H), 1.58 (bs, 2H), 1.68-1.76 (m, 2H), 1.79-1.89 (m, 4H), 1.93-1.98 (m, 1H), 2.14-2.17 (m, 1H), 2.21 (d, J=1.2 Hz, 4H), 2.29 (s, 3H), 2.45 (t, J=7.2 Hz, 2H), 2.54-2.57 (m, 2H), 3.15 (t, J=6.4 Hz, 2H), 2.78-3.42 (m, 9H), 3.54 (t, J=10 Hz, 4H), 3.78 (s, 3H), 3.83-3.97 (m, 6H), 4.00-4.11 (m, 4H), 4.16-4.34 (m, 4H), 7.16 (dd, J=17.6, 7.6 Hz, 4H)

MS (ESI) m/z 1174 [M−H]$^-$

Preparation of Compound Ga-1n

The compound 2n (9 mg, 10 μmol) was dissolved in water (1 mL), to which gallium trichloride (18 mg, 100 μmol) dissolved in water (1 mL) was added, followed by stirring at 70° C. for 1 hour. The reaction solution was filtered. The filtrate was separated by high performance liquid chromatography (HPLC) and dried using a lyophilizer to give the compound Ga-1n (4 mg, 41%) as a solid.

$^1$H NMR (400 MHz, D$_2$O) δ 1.94-2.03 (m, 2H), 2.15-2.45 (m, 2H), 2.47-2.54 (m, 3H), 2.63-2.71 (m, 2H), 3.32-3.48 (m, 9H), 3.53-3.72 (m, 15H), 3.78 (s, 2H), 3.90 (s, 4H), 3.95 (d, J=10.4 Hz, 2H), 4.04 (d, J=11.2 Hz, 2H), 4.22 (s, 2H), 4.23-4.33 (m, 3H);

MS (ESI) m/z 961 [M+H]$^+$

Preparation of Compound Ga-1o

The compound 2o (7 mg, 8 μmol) was dissolved in water (0.8 mL), to which gallium trichloride (14 mg, 80 μmol) dissolved in water (0.8 mL) was added, followed by stirring at 70° C. for 1 hour. The reaction solution was filtered. The filtrate was separated by high performance liquid chromatography (HPLC) and dried using a lyophilizer to give the compound Ga-1o (6 mg, 80%) as a solid.

$^1$H NMR (400 MHz, D$_2$O) δ 1.95-2.04 (m, 2H), 2.14-2.24 (m, 2H), 2.51-2.68 (m, 5H), 2.73-2.76 (m, 1H), 3.37-3.48 (m, 10H), 3.54-3.79 (m, 20H), 3.91 (s, 4H), 3.96 (d, J=10.4 Hz, 2H), 4.04 (d, J=11.2 Hz, 2H), 4.23-4.30 (m, 2H);

MS (ESI) m/z 977 [M+H]$^+$

Preparation of Compound Ga-1p

The compound 2p (9 mg, 10 μmol) was dissolved in water (1 mL), to which gallium trichloride (18 mg, 10 μmol) dissolved in water (1 mL) was added, followed by stirring at 70° C. for 1 hour. The reaction solution was filtered. The filtrate was separated by high performance liquid chromatography (HPLC) and dried using a lyophilizer to give the compound Ga-1p (5 mg, 51%) as a solid.

$^1$H NMR (400 MHz, D$_2$O) δ 1.86-2.02 (m, 2H), 2.08-2.21 (m, 2H), 2.44-2.49 (m, 3H), 2.67-2.73 (m, 1H), 3.25-3.42 (m, 9H), 3.45-3.59 (m, 8H), 3.66 (s, 2H), 3.80-3.95 (m, 7H), 4.00-4.10 (m, 4H), 4.15-4.19 (m, 2H), 4.56-4.59 (m, 2H), 4.64-4.73 (m, 2H), 4.77 (s, 2H), 7.93 (s, 0.4H), 8.03 (s, 0.6H);

MS (ESI) m/z 998 [M+H]$^+$

<Example 14> Preparation of Compound [$^{68}$Ga]1

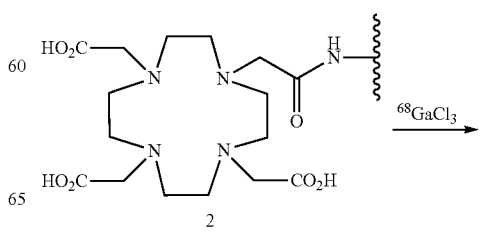

-continued

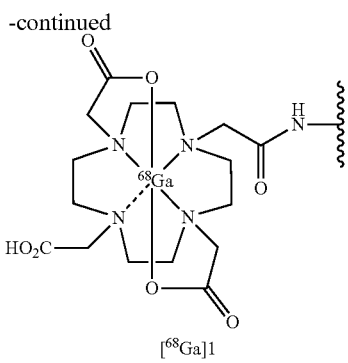

[$^{68}$Ga]1

Preparation of Compound [$^{68}$Ga]1a 0.1 N hydrochloric acid (5 mL) was poured into $^{68}$Ge/$^{68}$Ga generator and placed in test tubes (1 mL/tube). After measuring the radioactivity of each test tube, two $^{68}$Ga solutions (4.6 mCi, 2 mL) of the two test tubes showing high radioactivity were transferred to the reaction vessel. The compound 2a (200 μg) was dissolved in 1.0 M sodium acetate (0.4 mL)-aqueous hydrochloric acid solution (pH 4.55), which was loaded in a reaction vessel, followed by reaction at 80° C. for 10 minutes. The reaction solvent was filtered, and the filtrate was separated by high performance liquid chromatography. The separated solution was diluted with water (10 mL), passed through C-18 SepPak to capture, and washed with water (5 mL). After blowing nitrogen gas to remove moisture, it was eluted with ethanol (1 mL) to give the compound [$^{68}$Ga]1a (1.4 mCi).

Conditions of High Performance Liquid Chromatography:
  Column: RESTEK AQ (5 μm, 250 mm×10 mm);
  Moving phase: 25% methanol/water (0.1% TFA);
  Flow rate: 3 mL/min;
  UV detector: 230 nm;
  Residence time: 12 min.

Preparation of Compound [$^{68}$Ga]1b

The compound [$^{68}$Ga]1b (2.8 mCi) was obtained by the same manner as described in the preparation of the compound 1a except that $^{68}$Ga solution (5.94 mCi, 2 mL) and the compound 2b (200 μg) were used.

Conditions of High Performance Liquid Chromatography:
  Column: YMC-Pack ODS-A (S-5 μm, 12 nm, 250 mm×10 mm);
  Moving phase: 5% ethanol/water (0.1% TFA);
  Flow rate: 5 mL/min;
  UV detector: 254 nm;
  Residence time: 32 min.

Preparation of Compound [$^{68}$Ga]1c

The compound [$^{68}$Ga]1c (2.5 mCi) was obtained by the same manner as described in the preparation of the compound 1a except that $^{68}$Ga solution (5.7 mCi, 2 mL) and the compound 2c (200 μg) were used.

Conditions of High Performance Liquid Chromatography:
  Column: YMC-Pack ODS-A (S-5 μm, 12 nm, 250 mm×10 mm);
  Moving phase: 0-15% 30 min. acetonitrile/water (0.1% TFA);
  Flow rate: 3 mL/min;
  UV detector: 230 nm;
  Residence time: 31 min.

Preparation of Compound [$^{68}$Ga]1e

The compound [$^{68}$Ga]1e (2.4 mCi) was obtained by the same manner as described in the preparation of the compound 1a except that $^{68}$Ga solution (5.5 mCi, 2 mL) and the compound 2e (200 μg) were used.

Conditions of High Performance Liquid Chromatography:
  Column: YMC-Pack ODS-A (S-5 μm, 12 nm, 250 mm×10 mm);
  Moving phase: 8% ethanol/water (0.1% TFA);
  Flow rate: 4 mL/min;
  UV detector: 220 nm;
  Residence time: 14 min.

Preparation of Compound [$^{6}$Ga]1f

The compound [$^{68}$Ga]1f (1.3 mCi) was obtained by the same manner as described in the preparation of the compound 1a except that $^{68}$Ga solution (4.6 mCi, 2 mL) and the compound 2f (200 μg) were used.

Conditions of High Performance Liquid Chromatography:
  Column: Xterra MS C18 (10 μm, 250 mm×10 mm);
  Moving phase: 20% ethanol/water (0.1% TFA);
  Flow rate: 4 mL/min;
  UV detector: 220 nm;
  Residence time: 15 min.

Preparation of Compound [$^{68}$Ga]1g

The compound [$^{68}$Ga]1g (2.3 mCi) was obtained by the same manner as described in the preparation of the compound 1a except that $^{68}$Ga solution (5.5 mCi, 2 mL) and the compound 2g (200 μg) were used.

Conditions of High Performance Liquid Chromatography:
  Column: YMC-Pack ODS-A (S-5 μm, 12 nm, 250 mm×10 mm);
  Moving phase: 25% ethanol/water (0.1% TFA);
  Flow rate: 4 mL/min;
  UV detector: 220 nm;
  Residence time: 17 min.

Preparation of Compound [$^{68}$Ga]1h

The compound [$^{68}$Ga]1h (1.3 mCi) was obtained by the same manner as described in the preparation of the compound 1a except that $^{68}$Ga solution (4.6 mCi, 2 mL) and the compound 2h (200 μg) were used.

Conditions of High Performance Liquid Chromatography:
  Column: YMC-Pack ODS-A (S-5 μm, 12 nm, 250 mm×10 mm);
  Moving phase: 30% ethanol/water (0.1% TFA);
  Flow rate: 4 mL/min;
  UV detector: 220 nm;
  Residence time: 14 min.

Preparation of Compound [$^{68}$Ga]1k

The compound [$^{68}$Ga]1k (1.1 mCi) was obtained by the same manner as described in the preparation of the compound 1a except that $^{68}$Ga solution (3.9 mCi, 2 mL) and the compound 2k (200 μg) were used.

Conditions of High Performance Liquid Chromatography:
  Column: Xterra MS C18 (10 μm, 250 mm×10 mm);
  Moving phase: 25% ethanol/water (0.1% TFA);
  Flow rate: 4 mL/min;
  UV detector: 220 nm;
  Residence time: 18 min.

Preparation of Compound [$^{68}$Ga]1n

The compound [$^{68}$Ga]1n (3.8 mCi) was obtained by the same manner as described in the preparation of the compound 1a except that $^{68}$Ga solution (6.9 mCi, 2 mL) and the compound 2n (200 μg) were used.

Conditions of High Performance Liquid Chromatography:
Column: YMC-Pack ODS-A (S-5 µm, 12 nm, 250 mm×10 mm);
Moving phase: 7% acetonitrile/water (0.1% TFA);
Flow rate: 3 mL/min;
UV detector: 220 nm;
Residence time: 13 min.
Preparation of Compound [$^{68}$Ga]1o
The compound [68Ga]1o (2.1 mCi) was obtained by the same manner as described in the preparation of the compound 1a except that $^{68}$Ga solution (5.4 mCi, 2 mL) and the compound 2o (200 µg) were used.
Conditions of High Performance Liquid Chromatography:
Column: YMC-Pack ODS-A (S-5 µm, 12 nm, 250 mm×10 mm);
Moving phase: 7% ethanol/water (0.1% TFA);
Flow rate: 4 mL/min;
UV detector: 220 nm;
Residence time: 20 min.
Preparation of Compound [$^{68}$Ga]1p
The compound [$^{68}$Ga]1p (2.1 mCi) was obtained by the same manner as described in the preparation of the compound 1a except that $^{68}$Ga solution (5.8 mCi, 2 mL) and the compound 2p (200 µg) were used.
Conditions of High Performance Liquid Chromatography:
Column: RESTEK AQ (250 mm×10 mm);
Moving phase: 15% methanol/water (0.1% TFA);
Flow rate: 3 mL/min;
UV detector: 220 nm;
Residence time: 15 min.

<Example 15> Preparation of Compound [$^{64}$Cu]1b

The aqueous hydrochloric acid solution in which [$^{64}$Cu]CuCl$_2$ (7.3 mCi) was dissolved was heated at 90° C. and dried while blowing nitrogen gas. After drying, 0.1 mL of 0.1 M sodium citrate (pH 5.5) in which the compound 2b (100 µg) was dissolved was added thereto, followed by reaction at 60° C. for 10 minutes. Upon completion of the reaction, water (0.3 mL) was added to the reaction mixture, filtered, and washed twice with water (0.3 mL). The filtrate was separated by high performance liquid chromatography, passed through C-18 SepPak to capture, washed with 5 mL of water, and poured 1 mL of ethanol to give the compound [$^{64}$Cu]1b (5.22 mCi).
Conditions of High Performance Liquid Chromatography:
Column: Xterra MS C18 (10 µm, 250 mm×10 mm);
Moving phase: 50% acetonitrile/water (0.1% TFA);
Flow rate: 4 mL/min;
UV detector: 230 nm;
Residence time: 17.5 min.

<Example 16> Preparation of Compound [$^{177}$Lu]1g

The compound 2g (200 µg) dissolved in 1.0 M sodium acetate (0.4 mL)-aqueous hydrochloric acid solution (pH 4.88) was loaded in a reaction vessel containing Lu-177 (2.2 mCi), followed by reaction at 80° C. for 10 minutes. The reaction was filtered, and the filtrate was separated by high performance liquid chromatography. The separated solution was diluted with water (10 mL), passed through C-18 SepPak to capture, and washed with water (5 mL). After blowing nitrogen gas to remove moisture, it was eluted with ethanol (1 mL) to give the compound [$^{177}$Lu]1g (1.36 mCi).
Column: YMC-Pack ODS-A (S-5 µm, 12 nm, 250 mm×10 mm);
Moving phase: 25% ethanol/water (0.1% TFA);
Flow rate: 4 mL/min;
UV detector: 220 nm;
Residence time: 19 min.

<Comparative Example 1> Synthesis of Compound [$^{125}$I]30

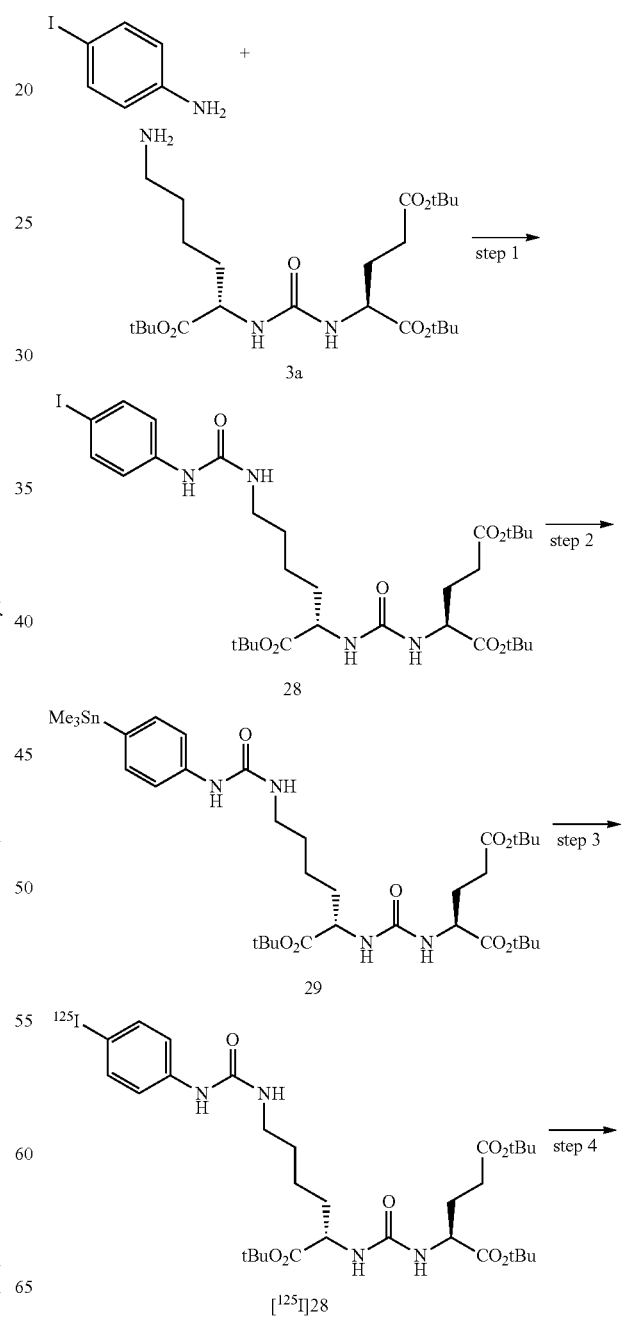

93

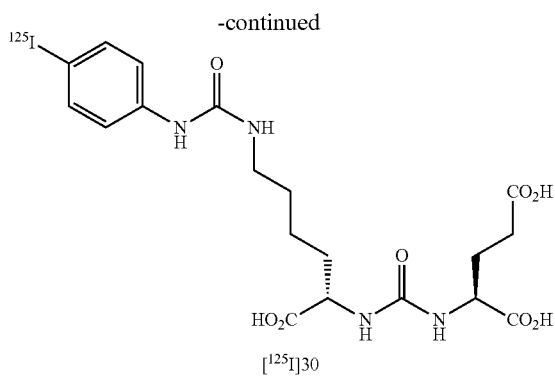

[125I]30

Step 1: Preparation of Compound 28

Triphosgene (21 mg, 71 ννομ) was dissolved in dichloromethane (5 νM), to which 4-iodoaniline (45 νη, 0.205 ννομ) dissolved in dichloromethane (5 νM) was slowly added at 0'C. Triethylamine (0.57 νM, 0.410 ννομ) was added thereto, followed by stirring at 0° C. for 30 minutes. The compound 3α (100 νη, 0.205 ννομ) dissolved in dichloromethane (10 νM) was slowly added thereto at 0° C., and triethylamine (0.57 νM, 0.410 ννομ) was also added. The mixture was stirred for 5 hours while slowly raising the temperature to room temperature. The reaction mixture was concentrated under reduced pressure, and the concentrate was separated by column chromatography (2% methanol/dichloromethane) to give the compound 28 (66 mg, 44%) as a white liquid.

$^1$H NMR (400 MHz, CDCl$_3$) δ 1.20-1.27 (m, 2H), 1.37 (s, 9H), 1.40 (s, 9H), 1.44 (s, 9H), 1.47-1.57 (m, 2H), 1.71-1.81 (m, 2H), 1.83-1.91 (m, 1H), 2.03-2.11 (m, 1H), 2.37 (sext, J=8.2 Hz, 2H), 3.01-3.07 (m, 1H), 3.51-3.56 (m, 1H), 3.97-4.01 (m, 1H), 4.26-4.32 (m, 1H), 5.75 (d, J=7.2 Hz, 1H), 6.31 (q, J=3.4 Hz, 1H), 6.40 (d, J=8.0 Hz, 1H), 7.27 (d, J=8.8 Hz, 2H), 7.52 (d, J=8.8 Hz, 2H), 7.90 (s, 1H);

$^{13}$C NMR (100 MHz, CDCl$_3$) δ 24.5, 27.1, 27.8, 27.9, 28.0, 29.6, 31.7, 32.0, 39.1, 53.8, 54.9, 81.0, 81.8, 83.6, 83.7, 120.2, 137.5, 140.2, 155.6, 158.5, 171.8, 172.0, 175.3;

MS (ESI) m/z 733 [M+H]$^+$

Step 2: Preparation of Compound 29

The compound 28 (50 mg, 0.068 mmol) synthesized in step 1 above was dissolved in dioxane (1.0 mL), to which hexamethyl ditin ((Me$_3$Sn)$_2$, 043 νM, 0.206 ννομ) and bis(triphenylphosphine)palladium(II) dichloride ((πδ(ππθ$_3$)Γμ$_2$, 4.8 νη, 5 ννομ) were added in that order, followed by stirring at 110° C. for 1.5 hours. The mixture was cooled to room temperature, to which an aqueous potassium fluoride solution (50 νM) was added, followed by stirring for 1 hour. The reactant was filtered, and the organic compound was extracted using ethylacetate. The collected organic solution was dried over anhydrous sodium sulfate and concentrated under reduced pressure. The concentrate was separated by column chromatography (triethylamine:ethylacetate:n-hexane, 1:40:59) to give the compound 29 (28 mg, 53%) as a white solid.

$^1$H NMR (400 MHz, CDCl$_3$) δ 0.25 (s, 9H), 1.22-1.29 (m, 2H), 1.38 (s, 9H), 1.41 (s, 9H), 1.43 (s, 9H), 1.48-1.59 (m, 2H), 1.72-1.78 (m, 1H), 1.81-1.91 (m, 1H), 2.05-2.13 (m, 2H), 2.34-2.43 (m, 2H), 3.04-3.09 (m, 1H), 3.51-3.55 (m, 1H), 4.04 (pent, J=4.9 Hz, 1H), 4.33 (sext, J=4.5 Hz, 1H), 5.73 (d, J=6.8 Hz 1H), 6.23 (br s, 1H), 6.32 (d, J=8.4 Hz, 1H), 7.35 (d, J=8.0 Hz, 2H), 7.43 (d, J=8.4 Hz, 2H), 7.73 (s, 1H);

94

$^{13}$C NMR (100 MHz, CDCl$_3$) δ −9.5, 24.2, 27.4, 27.8, 27.9, 28.0, 29.7, 31.8, 32.1, 39.1, 53.7, 54.7, 80.9, 81.7, 83.5, 118.4, 133.6, 136.2, 140.4, 155.9, 158.3, 171.9, 172.2, 175.1;

MS (ESI) in/z 771 [M+2H]$^+$

Step 3: Preparation of Compound [$^{125}$I]28

The compound 29 (100 νη) obtained in step 2 above was dissolved in ethanol (0.250 νM), to which sodium [$^{125}$I] iodide solution (3.2 mCi, 50 νM) was added, followed by stirring at room temperature. 1 Ξ aqueous hydrochloric acid solution (0.10 mL) and 3% H$_2$O$_2$ were added thereto, followed by stirring at room temperature for 10 minutes. 0.1 M sodium thiosulfate solution (0.20 mL) was added to the reaction mixture, to which distilled water (18 mL) was added. This solution was passed through C-18 SepPak and washed with distilled water (20 mL). After pouring acetonitrile (2.0 mL) on the C-18 Sep-Pak, nitrogen was blown into the solution to remove acetonitrile.

Step 4: Preparation of Compound [$^{125}$I]30

Dichloromethane (0.2 mL) and trifluoroacetic acid (0.8 mL) were sequentially added to the reaction vessel containing the reaction mixture obtained in step 3 above, followed by stirring at room temperature for 20 minutes. The reaction solvent was eliminated by blowing nitrogen, and then distilled water (2.0 mL) was added thereto. This solution was separated by high performance liquid chromatography (HPLC) to give the compound [$^{125}$I]20 (1.1 mCi, 24%).

HPLC Conditions:

Column, XTerra MS C18 (250 mm×10 mm); Moving phase, 30% acetonitrile/water (0.1% TFA); Flow rate, 5 mL/min; UV, 254 mm; Residence time, 10.4 min.

<Reference Example 1> Preparation of Prostate Cancer Cell Lines and Nude Mice

A human prostate cancer cell line (22RV1) used herein was purchased from American Type Culture Collection (ATCC). PC3 PIP (PSMA+) and PC3 flu (PSMA$^-$), the human prostate cancer cell lines, were provided by Dr. Martin G. Pomper (Johns Hopkins Medical School, Baltimore, MD). The human prostate cancer cell lines were maintained in RPMI1640 medium supplemented with 10% fetal bovine serum (FBS) and 1% antibiotic/antifungal agent. In the culture of PC3 PIP (PSMA+) and PC3 flu (PSMA−) cell lines, puromycin was additionally added at the concentration of 2 μg/mL.

As test animals, 6 weeks old male nude mice (Narabio, Seoul, Korea) were used.

<Experimental Example 1> Measurement of Lipophilicity (log P)

Each of the [$^{68}$Ga]1 compounds (1~2 mci) synthesized in Example 14 was transferred into a vial, and the solvent was removed, to which 1 mL of n-octanol and 1 mL of PBS were added, and the lid was well closed, followed by mixing with a vortex for 1 minute. After the layers were separated, 0.1 mL was taken from each layer and the radiation dose was measured. The radiation dose was measured by repeating 3 times, and the mean value was obtained.

TABLE 1

LogP values of [$^{68}$Ga]1 compounds

| [$^{68}$Ga]1 | logP |
|---|---|
| [$^{68}$Ga]1b | −2.56 |
| [$^{68}$Ga]1c | −2.65 |
| [$^{68}$Ga]1e | −2.88 |
| [$^{68}$Ga]1g | −2.42 |
| [$^{68}$Ga]1h | −1.89 |
| [$^{68}$Ga]1n | −3.06 |

<Experimental Example 2> Measurement of Binding Capacity

To confirm the binding capacity of the compounds of the present invention to PSMA, the following experiment was performed.

RPMI1640 supplemented with 1% BSA (bovine serum albumin) was used as a buffer solution.

[$^{125}$I]30 (0.1 nM) obtained in Comparative Example 1 was added to a vessel containing 22RV1 cells (5×10$^4$), to which the compound represented by formula 1 was loaded at 9 concentrations (1.00×10$^{-4}$~1.00×10$^{-12}$ M), followed by stirring at 37° C. for 2 hours. Upon completion of the stirring, the vessel was washed with PBS solution (2 mL) three times, and then the radioactivity was measured using a gamma counter (2480 WIZARD2 Gamma Counter Perkin-Elmer Co., MA). The 50% inhibition concentration (IC$_{50}$) for each compound was calculated using a GraphPad Prism program (GraphPad Software, Inc., CA)

Table 2 below is a table showing the binding affinity (IC$_{50}$) of each compound, and the K$_d$ value of the compound [$^{125}$I]30 was measured to be 0.13 nM. (Maresca, K. P. et al., 2009, J. Med. Chem. 52, 347-357)

TABLE 2

| Compound | IC$_{50}$ (nM) | K$_i$ value (nM) |
|---|---|---|
| Ga-1a | 570.70 ± 135.97 | 69.88 ± 29.78 |
| Ga-1b | 237.49 ± 47.13 | 18.73 ± 1.87 |
| Ga-1c | 21.20 ± 2.06 | 3.76 ± 0.37 |
| Ga-1d | 75.28 ± 18.61 | 18.62 ± 4.60 |
| Ga-1e | 47.41 ± 1.78 | 12.94 ± 0.49 |
| Ga-1f | 25.66 ± 5.06 | 8.12 ± 1.60 |
| Ga-1g | 18.40 ± 0.35 | 5.82 ± 0.11 |
| Ga-1h | 11.00 ± 0.35 | 3.00 ± 0.10 |
| Ga-1i | 68.99 ± 3.27 | 14.36 ± 0.68 |
| Ga-1j | 60.41 ± 3.61 | 12.57 ± 0.75 |
| Ga-1k | 63.85 ± 6.09 | 12.70 ± 1.07 |
| Ga-1n | 174.13 ± 3.87 | 32.09 ± 0.71 |
| Ga-1o | 1140.29 ± 82.36 | 282.09 ± 20.37 |
| Ga-1p | 702.95 ± 144.61 | 129.54 ± 26.65 |

As shown in Table 2, the compounds Ga-1a and Ga-1b of Example 13 of the present invention are compounds that do not have a carboxylic acid in the nitrogen of the lysine residue. In particular, Ga-1a showed a relatively low binding force to PSMA. On the other hand, Ga-1a having a structure similar to Ga-1a is a compound having a carboxylic acid in the nitrogen of the lysine residue, and it can be seen that the binding force to PSMA was about 18.6 times higher than that of Ga-1a. This is because one (R463) of three arginine residues, called an arginine patch, in the binding region of PSMA and the carboxylic acid bound to the nitrogen of the lysine residue of the compound represented by formula 1 of the present invention form a strong salt bridge interaction.

In addition, the carboxylic acid of the lysine residue in the compound represented by formula 1 of the present invention not only greatly improved the binding capacity to PSMA, but also increased the hydrophilicity of the compound to lower the non-specific binding in vivo and removed it more quickly in normal organs.

The compounds Ga-1f, Ga-1g and Ga-1h have a phenyl group or a substituted phenyl group, and it was confirmed that they have a higher binding capacity than the compound Ga-1e having a similar structure without a phenyl group. Among them, the 4-iodophenyl-bonded compound Ga-1h had the highest binding capacity.

<Experimental Example 3> Experiment of MicroPET/CT Imaging of Mice Transplanted with Prostate Cancer Cell Lines A tumor model was prepared by subcutaneously injecting PSMA$^+$ PC-3 PIP cells (a human prostate cancer cell line) to the right side of the nude mouse hind leg. Each of the $^{68}$Ga-labeled compounds [$^{68}$Ga]1e, [$^{68}$Ga]1g, [$^{68}$Ga]1h and [$^{68}$Ga]1k was intravenously injected with 5.5 to 6.5 MBq (148-175 µCi/200 µL), and PET/CT images were obtained using small animal INVEON PET/CT (Siemens medical solutions, Knoxville, USA) for 60 minutes. After 150 minutes, 270 minutes, and 390 minutes, PET/CT images were also obtained for 30 minutes. The obtained PET/CT image results were quantitatively analyzed using Inveon™ Research Workplace (IRW).

FIGS. 1, 2, 3, and 4 are graphs showing the quantitative analysis results of MicorPET/CT images for [$^{68}$Ga]1e, [$^{68}$Ga]1g, [$^{68}$Ga]1h, and [$^{68}$Ga]1k in % injected dose (ID)/g, and summarized in Tables 3, 4, 5, and 6, respectively.

[$^{68}$Ga]1e was found to be rapidly excreted through the kidney and bladder at the initial stage after injection, and it was confirmed that it selectively bound to PSMA$^+$ PC-3 PIP tumors at a level of 4.05±0.64% ID/g at 270 minutes after injection (FIG. 1, Table 3).

Figure 2:
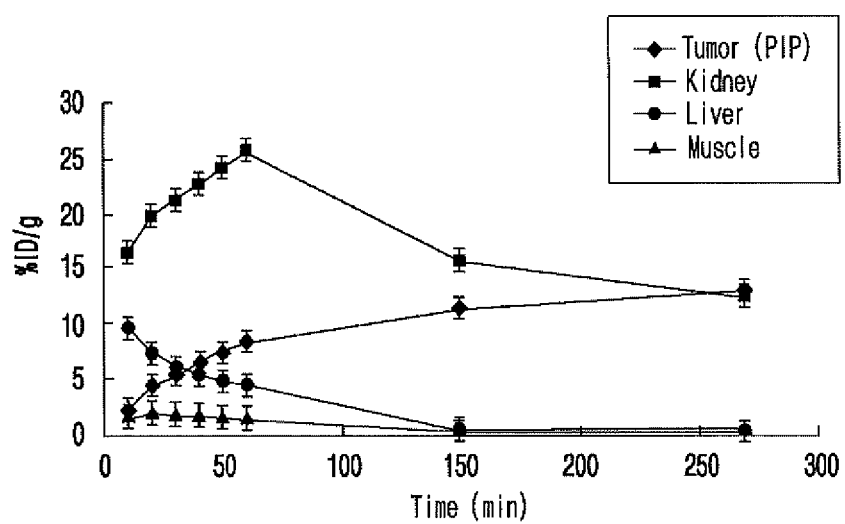
FIG. 2 is a graph showing the results of quantitative analysis of MicroPET/CT images acquired for 270 minutes after the administration of [$^{68}$Ga]1g.
Figure 3:
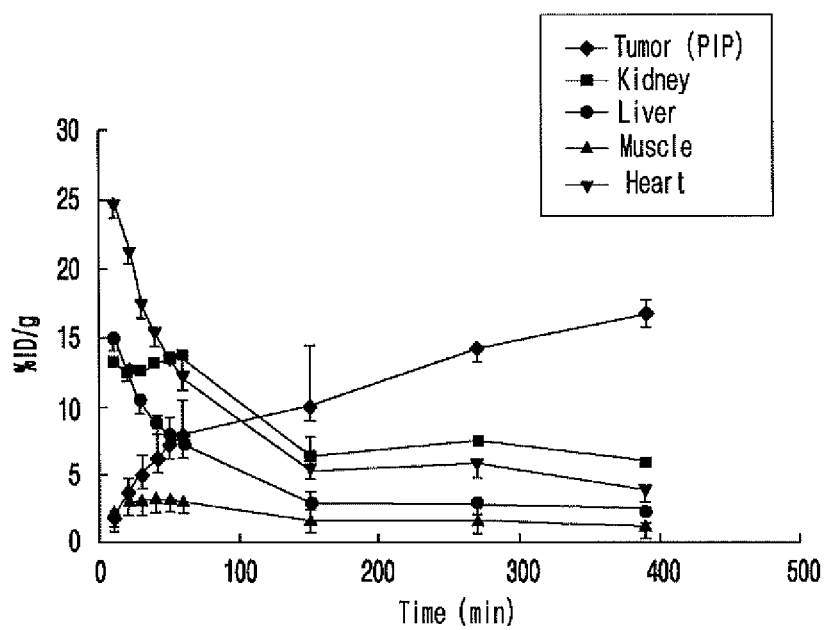
FIG. 3 is a graph showing the results of quantitative analysis of MicroPET/CT images acquired for 390 minutes after the administration of [$^{68}$Ga]1h.

In the case of [$^{68}$Ga]1g, it was confirmed that the residence time in the blood was increased due to the albumin binding capacity of the phenyl group, and the tumor intake was increased over time. Compared to the compound [$^{68}$Ga]1e, the tumor intake of 13.00±4.95% ID/g, which was increased by about 3 times at 270 minutes, was confirmed (FIG. 2, Table 4).

In the case of [$^{68}$Ga]1h and [$^{68}$Ga]1k, due to the albumin binding capacity of the substituted phenyl group, the residence time in the blood was increased and the tumor intake was confirmed to increase over time, and the tumor intake continued to increase after 390 minutes.

Figure 4:
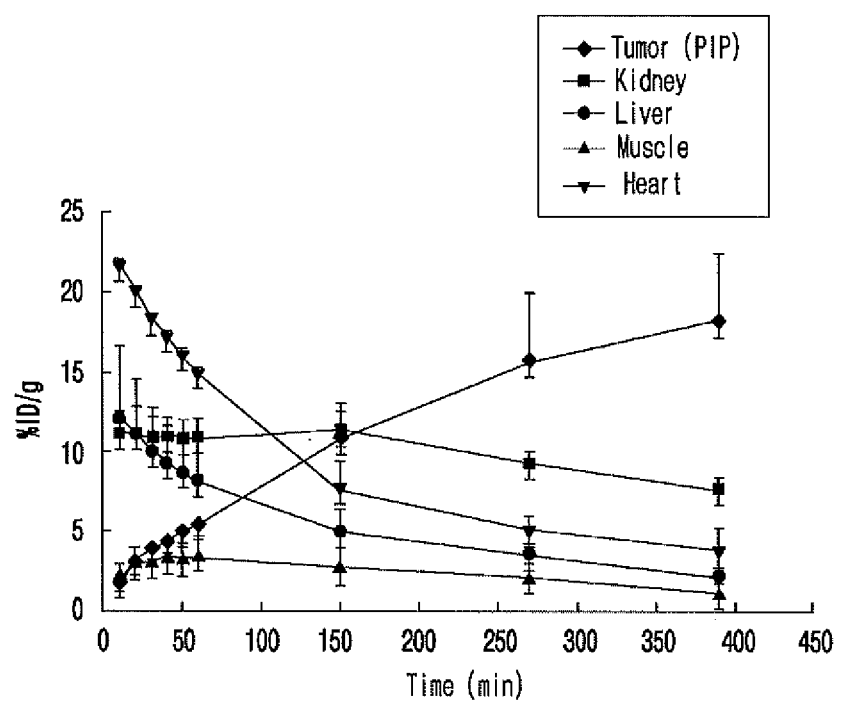
FIG. 4 is a graph showing the results of quantitative analysis of MicroPET/CT images acquired for 390 minutes after the administration of [$^{68}$Ga]1k.

The compound [$^{68}$Ga]1h showed the tumor intake of 16.75±0.92% ID/g at 390 minutes (FIG. 3, Table 5), and the compound [$^{68}$Ga]1k showed the tumor intake of 18.25±4.17% ID/g at 390 minutes (FIG. 4, Table 6).

In addition, it was confirmed that all of the compounds [$^{68}$Ga]1e, [$^{68}$Ga]1g, [$^{68}$Ga]1h and [$^{68}$Ga]1k were rapidly excreted out of the body as the intake in the kidney was decreased after 150 minutes.

TABLE 3

[$^{68}$Ga]1e intake of each mouse organ over time (% ID/g)

| Time | Tumor (PIP) | Kidney | Bladder | Liver | Muscle |
|---|---|---|---|---|---|
| 10 | 2.33 ± 0.36 | 21.37 ± 9.18 | 19.37 ± 0.32 | 4.76 ± 0.42 | 1.46 ± 0.14 |
| 20 | 3.64 ± 0.49 | 10.96 ± 4.32 | 47.31 ± 7.34 | 1.96 ± 0.22 | 1.38 ± 0.11 |
| 30 | 4.08 ± 0.60 | 10.88 ± 7.09 | 55.82 ± 12.46 | 1.29 ± 0.05 | 0.95 ± 0.13 |
| 40 | 4.44 ± 0.48 | 14.92 ± 13.57 | 60.63 ± 15.48 | 1.00 ± 0.03 | 0.61 ± 0.05 |
| 50 | 4.56 ± 1.03 | 15.84 ± 15.60 | 64.24 ± 12.76 | 0.80 ± 0.02 | 0.53 ± 0.05 |
| 60 | 4.73 ± 0.98 | 15.72 ± 16.29 | 67.80 ± 8.56 | 0.65 ± 0.04 | 0.35 ± 0.05 |
| 150 | 4.20 ± 0.42 | 0.70 ± 0.02 | 31.85 ± 35.57 | 0.06 ± 0.01 | 0.02 ± 0.01 |
| 270 | 4.05 ± 0.64 | 0.41 ± 0.16 | 1.45 ± 1.62 | 0.03 ± 0.01 | 0.01 ± 0.01 |

TABLE 4

[$^{68}$Ga]1g intake of each mouse organ over time (% ID/g)

| Time | Tumor (PIP) | Kidney | Bladder | Liver | Muscle |
|---|---|---|---|---|---|
| 10 | 2.18 ± 0.63 | 16.40 ± 0.10 | 2.28 ± 0.11 | 9.55 ± 2.22 | 1.49 ± 1.64 |
| 20 | 4.42 ± 1.50 | 19.80 ± 0.73 | 6.98 ± 2.51 | 7.26 ± 1.06 | 1.88 ± 2.00 |
| 30 | 5.43 ± 1.94 | 21.18 ± 2.17 | 13.51 ± 5.83 | 6.10 ± 0.50 | 1.69 ± 1.78 |
| 40 | 6.43 ± 2.32 | 22.74 ± 3.48 | 18.89 ± 8.84 | 5.38 ± 0.22 | 1.61 ± 1.69 |
| 50 | 7.33 ± 2.76 | 24.20 ± 4.60 | 22.76 ± 10.86 | 4.75 ± 0.07 | 1.54 ± 1.62 |
| 60 | 8.29 ± 2.99 | 25.78 ± 4.72 | 24.74 ± 11.23 | 4.41 ± 0.03 | 1.32 ± 1.33 |
| 150 | 11.4 ± 5.23 | 15.75 ± 11.53 | 42.3 ± 41.58 | 0.45 ± 0.11 | 0.21 ± 0.03 |
| 270 | 13.00 ± 4.95 | 12.45 ± 9.69 | 12.05 ± 2.76 | 0.22 ± 0.01 | 0.06 ± 0.02 |

TABLE 5

[$^{68}$Ga]1h intake of each mouse organ over time (% ID/g)

| Time | Tumor (PIP) | Kidney | Bladder | Liver | Muscle | Heart |
|---|---|---|---|---|---|---|
| 10 | 1.94 ± 0.35 | 13.26 ± 2.36 | 2.12 ± 0.39 | 14.96 ± 0.03 | 2.24 ± 0.15 | 24.69 ± 0.20 |
| 20 | 3.74 ± 0.97 | 12.56 ± 0.86 | 2.91 ± 0.69 | 12.71 ± 0.03 | 2.97 ± 0.35 | 21.30 ± 0.11 |
| 30 | 5.00 ± 1.41 | 12.61 ± 0.71 | 3.14 ± 0.51 | 10.37 ± 0.12 | 2.98 ± 0.34 | 17.38 ± 0.04 |
| 40 | 6.22 ± 1.75 | 13.51 ± 0.46 | 4.52 ± 0.97 | 8.86 ± 0.35 | 3.28 ± 0.23 | 15.25 ± 0.15 |
| 50 | 7.12 ± 2.07 | 13.44 ± 0.71 | 8.26 ± 4.41 | 7.83 ± 0.45 | 3.25 ± 0.36 | 13.52 ± 0.55 |
| 60 | 7.90 ± 2.46 | 13.60 ± 1.72 | 12.62 ± 5.31 | 7.19 ± 0.49 | 3.14 ± 0.20 | 12.14 ± 0.91 |
| 150 | 9.90 ± 4.53 | 6.40 ± 1.41 | 19.45 ± 12.23 | 2.80 ± 0.99 | 1.70 ± 0.57 | 5.55 ± 2.19 |
| 270 | 14.20 ± 0.00 | 7.45 ± 1.63 | 15.90 ± 4.53 | 3.00 ± 0.28 | 1.70 ± 0.14 | 5.75 ± 0.21 |
| 390 | 16.75 ± 0.92 | 5.85 ± 0.92 | 22.80 ± 9.90 | 2.35 ± 0.07 | 1.30 ± 0.14 | 3.90 ± 0.42 |

TABLE 6

[$^{68}$Ga]1k intake of each mouse organ over time (% ID/g)

| Time | Tumor (PIP) | Kidney | Bladder | Liver | Muscle | Heart |
|---|---|---|---|---|---|---|
| 10 | 1.85 ± 0.25 | 11.16 ± 1.35 | 4.12 ± 0.45 | 11.99 ± 4.72 | 2.26 ± 0.75 | 21.67 ± 0.44 |
| 20 | 3.22 ± 0.38 | 11.21 ± 1.62 | 4.68 ± 0.22 | 11.09 ± 3.46 | 2.91 ± 1.21 | 20.10 ± 0.29 |
| 30 | 3.94 ± 0.38 | 10.89 ± 1.36 | 4.68 ± 0.45 | 10.04 ± 2.73 | 3.09 ± 0.91 | 18.33 ± 0.13 |
| 40 | 4.40 ± 0.36 | 11.06 ± 1.02 | 4.75 ± 0.21 | 9.31 ± 2.32 | 3.32 ± 1.20 | 17.22 ± 0.35 |
| 50 | 5.03 ± 0.33 | 10.80 ± 1.20 | 4.83 ± 0.18 | 8.73 ± 2.11 | 3.24 ± 1.07 | 16.06 ± 0.38 |
| 60 | 5.45 ± 0.16 | 10.96 ± 1.18 | 4.81 ± 0.24 | 8.22 ± 1.79 | 3.49 ± 1.28 | 15.03 ± 0.27 |
| 150 | 11.00 ± 2.12 | 11.40 ± 1.13 | 18.10 ± 6.51 | 5.00 ± 1.41 | 2.75 ± 1.20 | 7.85 ± 1.63 |
| 270 | 15.70 ± 4.24 | 9.25 ± 0.78 | 20.10 ± 4.53 | 3.60 ± 0.71 | 2.15 ± 0.78 | 5.10 ± 0.85 |
| 390 | 18.25 ± 4.17 | 7.70 ± 0.71 | 14.25 ± 0.64 | 2.25 ± 0.64 | 1.20 ± 0.56 | 3.80 ± 1.41 |

<Experimental Example 4> Biodistribution Test with Mice Transplanted with Prostate Cancer Cell Lines After 270 minutes of [$^{68}$Ga]1e and [$^{68}$Ga]1g injection, microPET/CT images were obtained for 30 minutes, and then each organ (blood, muscle, fat, heart, lung, liver, spleen, stomach, intestine, kidney, bone and tumor) was extracted and the radioactivity thereof was measured using a gamma counter.

Table 7 shows the intake of each organ 5 hours after the injection of [$^{68}$Ga]1e or [$^{68}$Ga]1g.

Biodistribution was confirmed 5 hours after the compound injection. As a result, [$^{68}$Ga]1g containing a phenyl group showed a higher tumor intake rate (% ID/g) of more than 10%, which was about 1.4 times higher than that of [$^{68}$Ga]1e.

TABLE 7

Radioactivity of [$^{68}$Ga]1e and [$^{68}$Ga]1g in mouse organ

| | [$^{68}$Ga]1e | [$^{68}$Ga]1g |
|---|---|---|
| Blood | 0.01 ± 0.00 | 0.02 ± 0.03 |
| Muscle | 0.01 ± 0.00 | 0.01 ± 0.00 |
| Fat | 0.01 ± 0.00 | 0.11 ± 0.15 |
| Heart | 0.01 ± 0.00 | 0.02 ± 0.01 |
| Lung | 0.02 ± 0.01 | 0.07 ± 0.07 |
| Liver | 0.02 ± 0.01 | 0.03 ± 0.01 |
| Spleen | 0.01 ± 0.00 | 0.20 ± 0.27 |
| Stomach | 0.02 ± 0.02 | 0.02 ± 0.02 |
| Intestine | 0.09 ± 0.08 | 0.09 ± 0.08 |
| Kidney | 0.82 ± 0.51 | 9.15 ± 11.26 |
| Bone | 0.00 ± 0.00 | 0.01 ± 0.01 |
| PSMA + PIP | 7.34 ± 5.49 | 10.48 ± 1.05 |

Meanwhile, the compound represented by formula 1 according to the present invention can be formulated in various forms depending on the purpose of use. The following illustrates some formulation methods in which the compound represented by formula 1 according to the present invention is contained as an active ingredient, but the present invention is not limited thereto.

<Manufacturing Example 1> Preparation of Pharmaceutical Formulations 1-1. Preparation of Powders

| | |
|---|---|
| Compound of formula 1 | 500 mg |
| Lactose | 100 mg |
| Talc | 10 mg |

Powders were prepared by mixing all the above components, which were filled in airtight packs.

1-2. Preparation of Tablets

| | |
|---|---|
| Compound of formula 1 | 500 mg |
| Corn starch | 100 mg |
| Lactose | 100 mg |
| Magnesium stearate | 2 mg |

Tablets were prepared by mixing all the above components by the conventional method for preparing tablets.

1-3. Preparation of Capsules

| | |
|---|---|
| Compound of formula 1 | 500 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

1-4. Preparation of Injectable Solution

| | |
|---|---|
| Compound of formula 1 | 500 mg |
| Sterilized distilled water | proper amount |
| PH regulator | proper amount |

Injectable solutions were prepared by mixing all the above components, putting the mixture into 2 m $\ell$ ampoules and sterilizing thereof by the conventional method for preparing injectable solutions.

1-5. Preparation of Liquid Formulations

| | |
|---|---|
| Compound of formula 1 | 100 mg |
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

As mentioned above, the present invention has been described in detail through the preferred preparative examples, examples and experimental examples, but the scope of the present invention is not limited to the specific examples, and should be interpreted by the appended claims. In addition, those of ordinary skill in the art should understand that many modifications and variations are possible without departing from the scope of the present invention.

INDUSTRIAL APPLICABILITY

The present invention relates to a pharmaceutical composition for diagnosing and treating prostate cancer, capable of targeting PSMA, and a compound provided by one aspect of the present invention has a glutamine-urea-lysine compound to which a radioactive metal-coupled chelator is structurally coupled and to which an aryl group that can additionally bind to PSMA protein is coupled. Coupling between the glutamine-urea-lysine compound and the chelator includes a polar spacer so as to serve the role of reducing in vivo nonspecific coupling and exhibit an effect of being rapidly removed from vital organs, but not from prostate cancer. These characteristics lower the radiation exposure, which is caused by a therapeutic radioisotope-coupled compound, to normal tissue and organs, and thus reduce side effects. In addition, a compound that contains a phenyl group having a coupling force with albumin has an increased residence time in the blood, thereby becoming more accumulated in prostate cancer.

What is claimed is:

1. A compound represented by formula 1, a stereoisomer thereof, a hydrate thereof, or a pharmaceutically acceptable salt thereof:

[Formula 1]

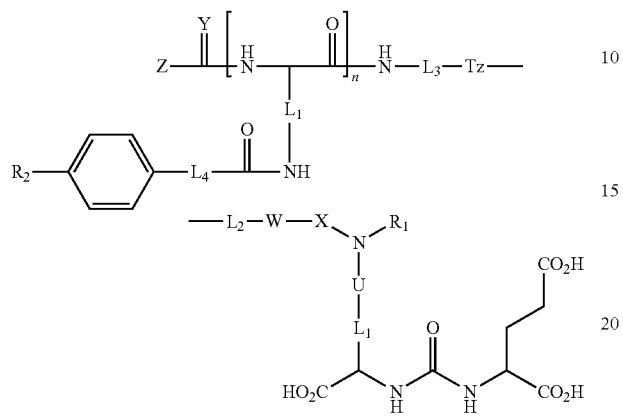

In formula 1,
L₁ is —(CH₂)ₐ—, wherein a is an integer of 1 to 8;
U is a bond, or —C(O)—;
R₁ is -L₅-CO₂H, wherein L₅ is —(CH₂)ᵦ—, wherein b is an integer of 1 to 6;
X is a bond, or —C(O)—;
W is a bond, or —NA₁-, A₁ is hydrogen, or —(CH₂)ᵧ-pyridyl, wherein c is an integer of 0 to 3;
L₂ is a bond, or —(CH₂)ₐ—, wherein d is an integer of 1 to 8;
Tz is a bond,

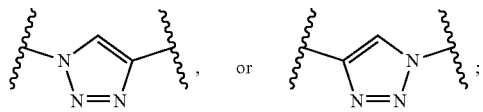 [SMILES: *c1cn(*)nn1 ; *c1cn(*)nn1]

L₃ is C₁₋₁₂ straight or branched alkylene, wherein one or more carbon atoms in alkylene can be replaced by oxygen atoms;
L₄ is —(CH₂)ₑ—, wherein e is an integer of 1 to 6;
n is an integer of 0 to 1;
R₂ is hydrogen, C₁₋₅ straight or branched alkyl, or halogen;
Y is oxygen or sulfur;
Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

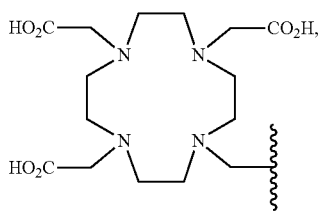 [SMILES: *CN1CCN(CC(=O)O)CCN(CC(=O)O)CCN(CC(=O)O)CC1]

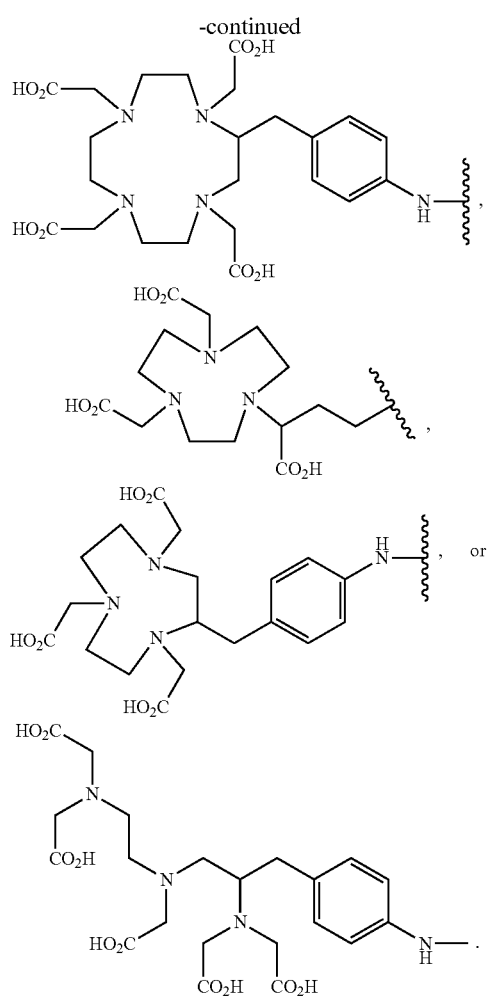

2. The compound, the stereoisomer thereof, the hydrate thereof, or the pharmaceutically acceptable salt thereof according to claim 1, wherein:
L₁ is —(CH₂)ₐ—, wherein a is an integer of 1 to 6;
U is a bond, or —C(O)—;
R₁ is -L₅-CO₂H, wherein L₅ is —(CH₂)ᵦ—, wherein b is an integer of 1 to 4;
X is a bond, or —C(O)—;
W is a bond, or —NA₁-, A₁ is hydrogen, or —(CH₂)ᵧ-pyridyl, wherein c is an integer of 0 to 1;
L₂ is a bond, or —(CH₂)ₐ—, wherein d is an integer of 1 to 6;
Tz is a bond,

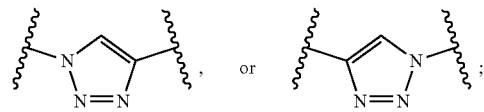

L₃ is C₁₋₁₀ straight or branched alkylene, wherein one or more carbon atoms in alkylene can be replaced by oxygen atoms;
L₄ is —(CH₂)ₑ—, wherein e is an integer of 2 to 4;
n is an integer of 0 to 1;
R₂ is hydrogen, C₁₋₃ straight or branched alkyl, or halogen;

Y is oxygen or sulfur;

Z is a chelator including a radioactive metal, wherein the radioactive metal is Ga-68, Cu-64, Cu-67, Y-90, Sc-47, In-111, Sn-117m, Lu-177, Bi-212, Bi-213, Pb-212, Ra-223, or Ac-225, and the chelator is

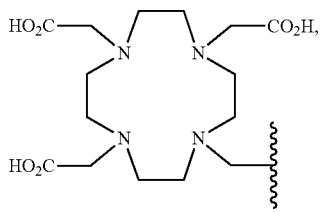

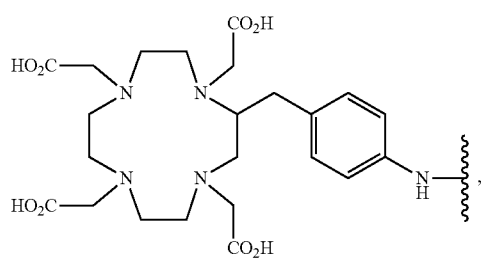

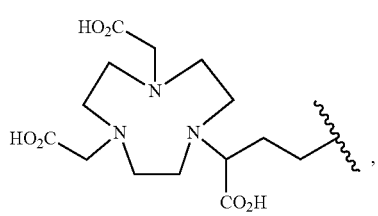

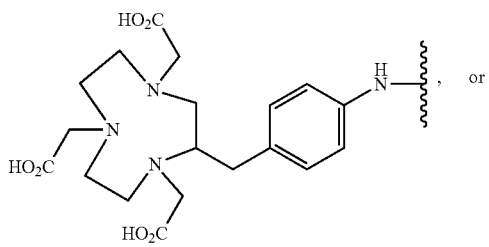

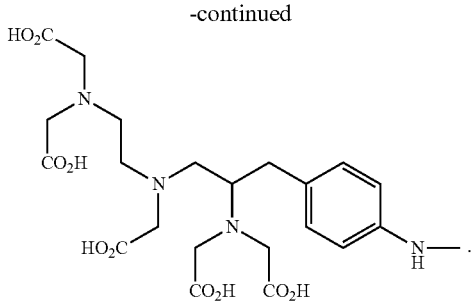

3. The compound, the stereoisomer thereof, the hydrate thereof, or the pharmaceutically acceptable salt thereof according to claim 1, wherein:

$L_1$ is —(CH$_2$)$_a$—, wherein a is an integer of 2 to 4;

U is a bond, or —C(O)—;

$R_1$ is -$L_5$-CO$_2$H, wherein $L_5$ is —(CH$_2$)$_b$—, wherein b is an integer of 1 to 2;

X is a bond, or —C(O)—;

W is a bond, or —NA$_1$-, wherein A$_1$ is hydrogen or pyridyl;

$L_2$ is a bond, or —(CH$_2$)$_d$—, wherein d is an integer of 1 to 2;

Tz is a bond,

$L_3$ is C$_{1-8}$ straight alkylene, wherein one or more carbon atoms in alkylene can be replaced by oxygen atoms;

$L_4$ is —(CH$_2$)$_3$—;

n is an integer of 0 to 1;

$R_2$ is hydrogen, methyl or halogen;

Y is oxygen;

Z is a chelator including a radioactive metal, wherein the radioactive metal is Ga-68, Cu-64, or Lu-177, and the chelator can be

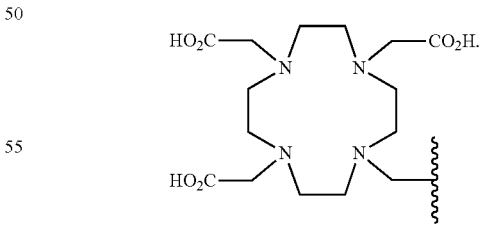

4. The compound, the stereoisomer thereof, the hydrate thereof, or the pharmaceutically acceptable salt thereof according to claim 1, wherein the compound represented by formula 1 is selected from the group consisting of the following compounds:

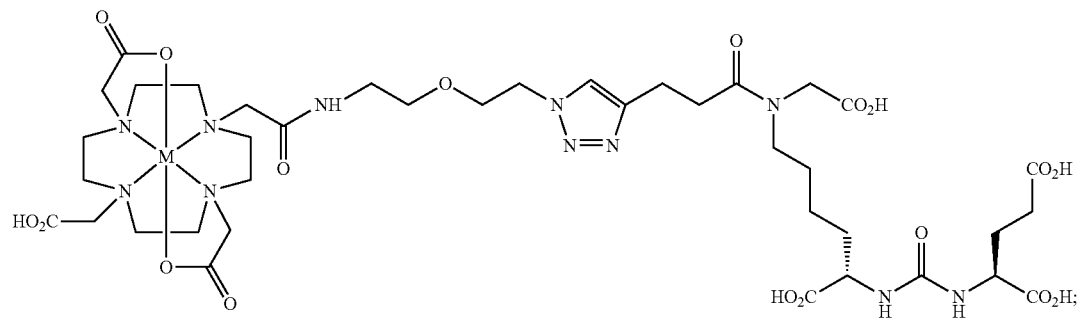
(3)
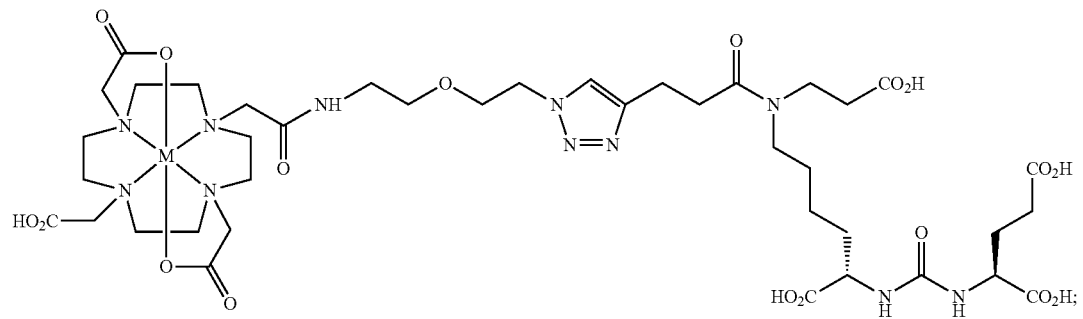
(4)
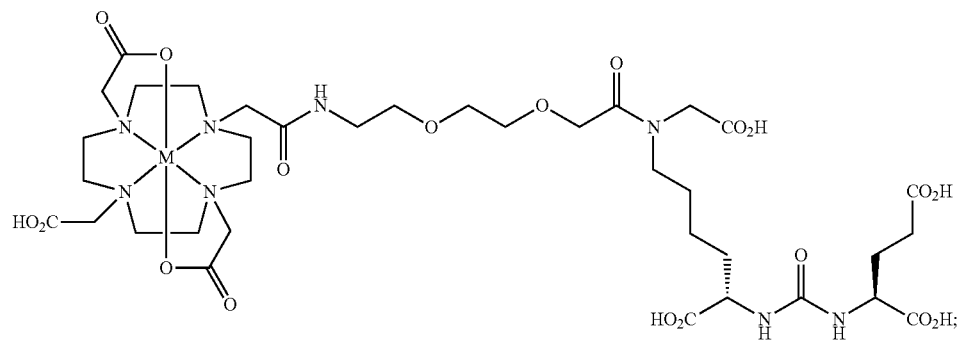
(5)
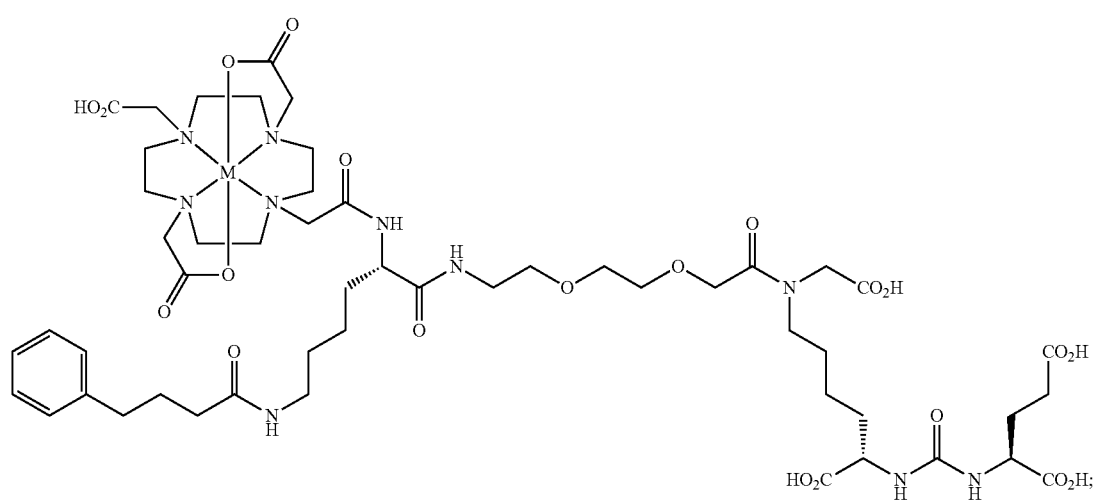
(6)

-continued
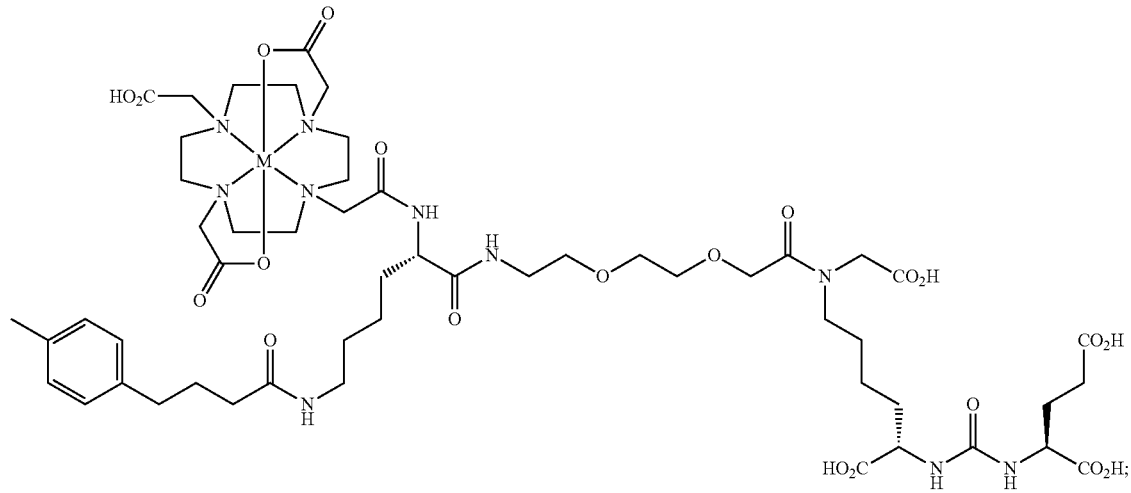
(7)
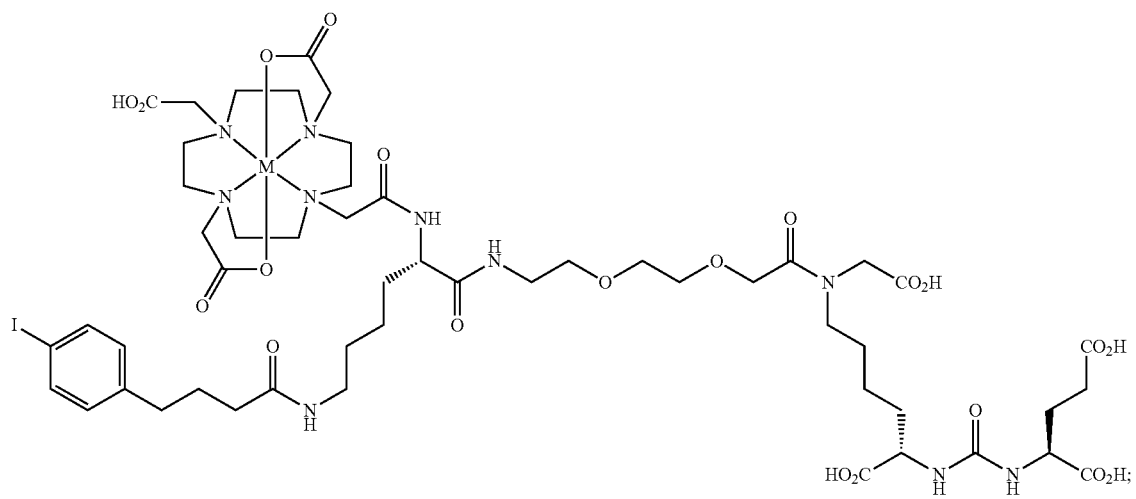
(8)
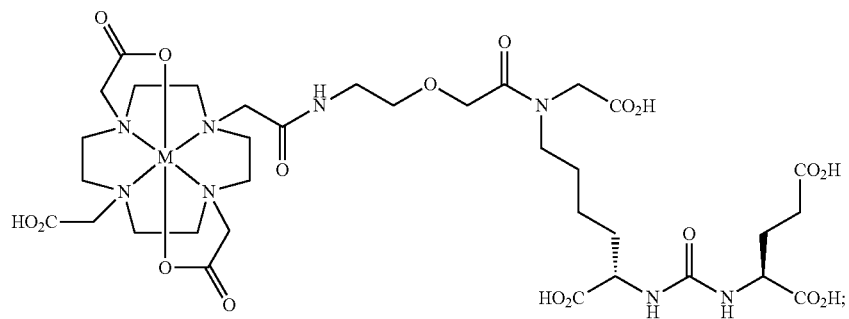
(9)

(10)
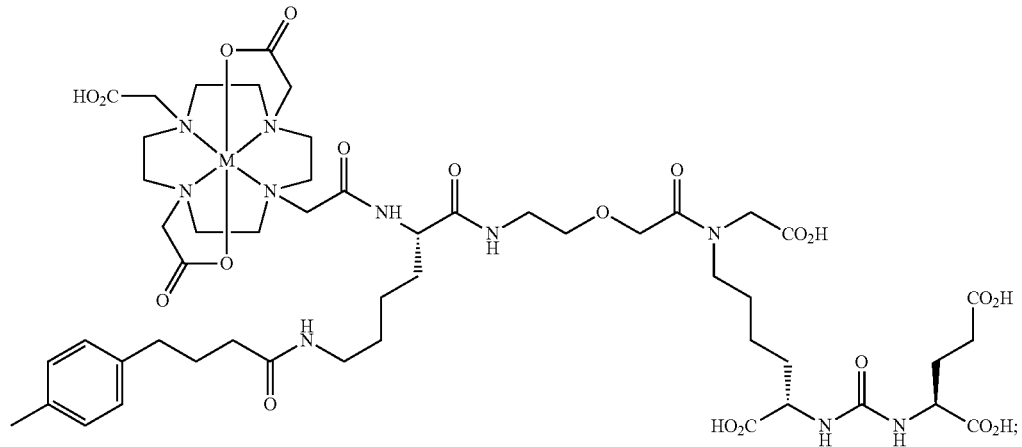
(11)
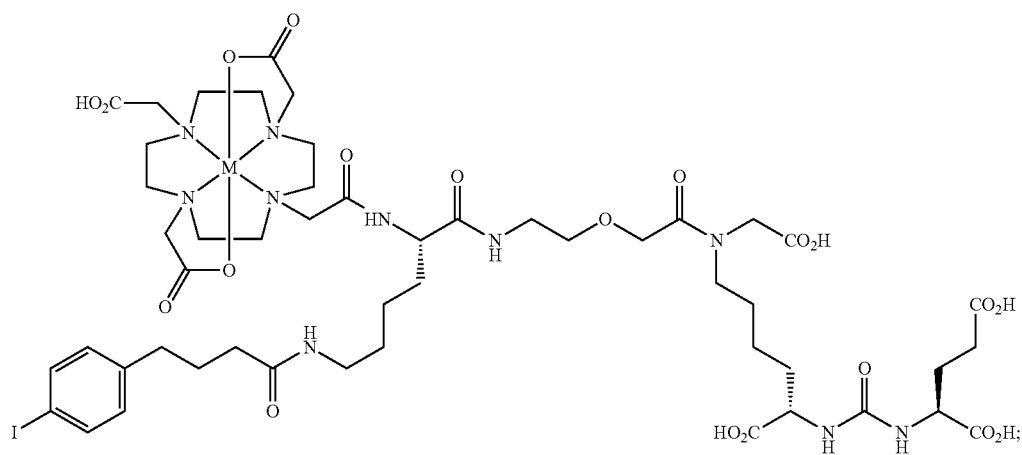
(12)
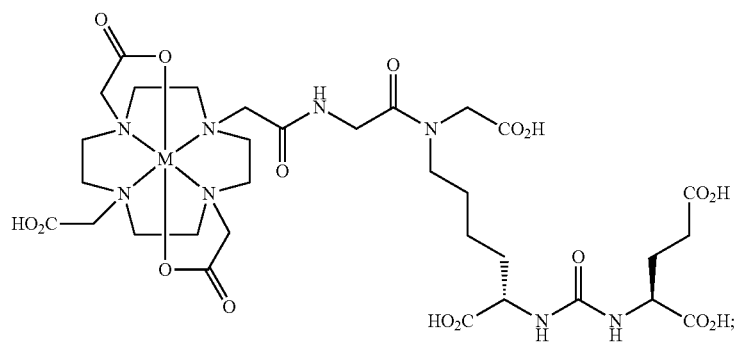

-continued
(13)
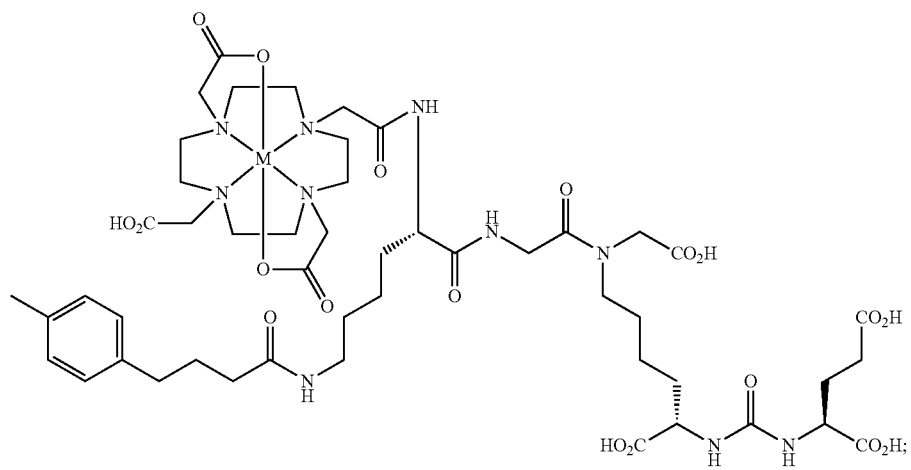
(14)
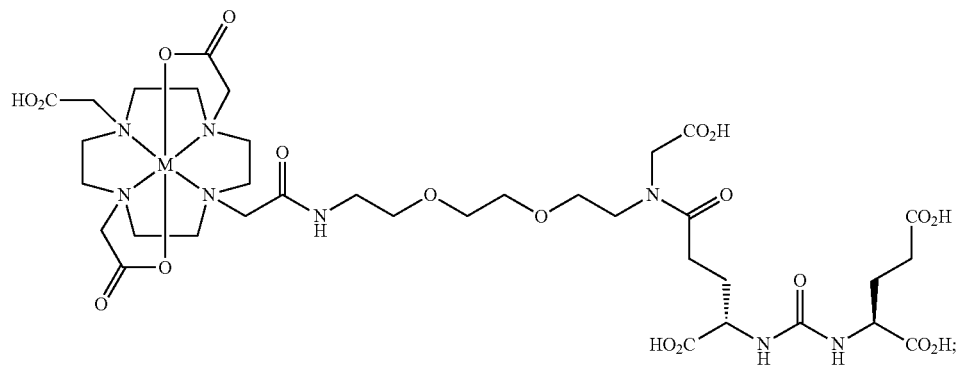
(15)
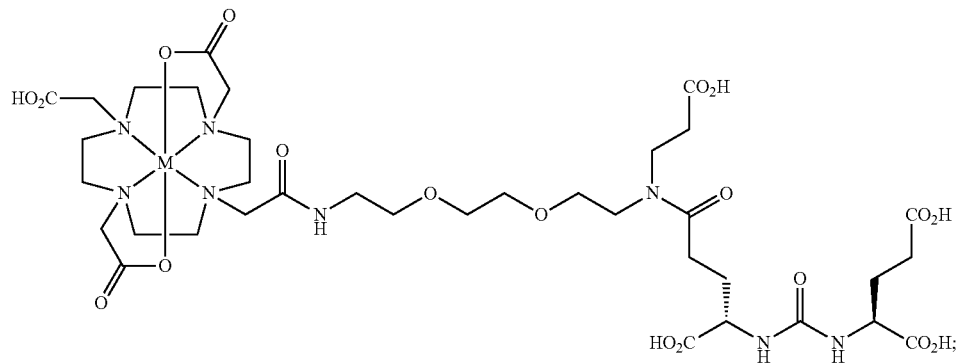
(16)
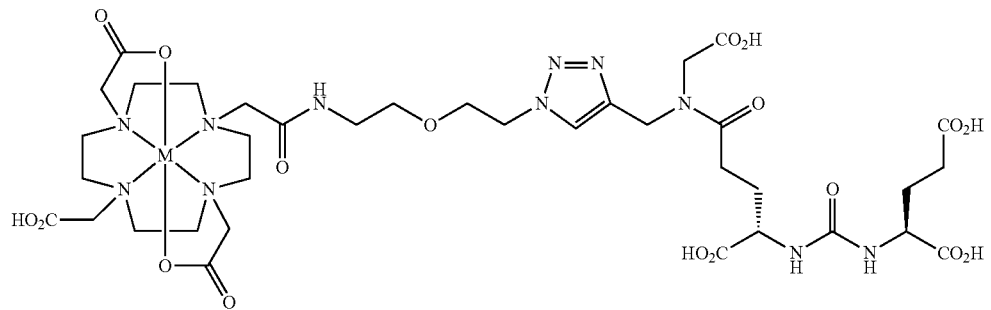

wherein M is a radioactive metal, and the radioactive metal is as defined in claim 1.

5. A compound represented by formula 2, a stereoisomer thereof, a hydrate thereof, or a pharmaceutically acceptable salt thereof:

[Formula 2]

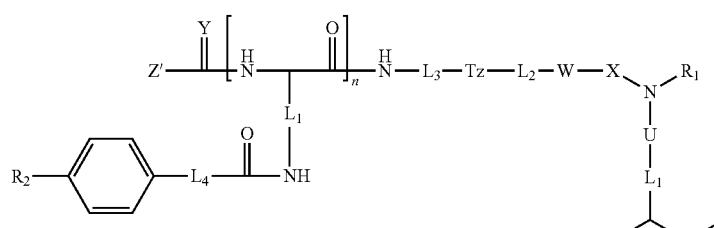

wherein in formula 2,
$L_1$ is —$(CH_2)_a$—, wherein a is an integer of 1 to 8;
U is a bond, or —C(O)—;
$R_1$ is -$L_5$-$CO_2H$, wherein $L_5$ is —$(CH_2)_b$—, wherein b is an integer of 1 to 6;
X is a bond, or —C(O)—;
W is a bond or —$NA_1$-, and $A_1$ is hydrogen or —$(CH_2)_c$-pyridyl, wherein c is an integer of 0 to 3;
$L_2$ is a bond or —$(CH_2)_d$—, wherein d is an integer of 1 to 8;
Tz is a bond,

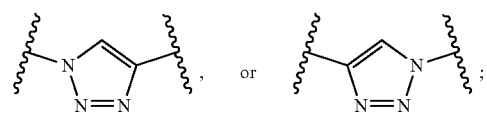 [SMILES: *c1cn(*)nn1 ; *c1cn(*)nn1]

$L_3$ is $C_{1-12}$ straight or branched alkylene, wherein one or more carbon atoms in alkylene can be replaced by oxygen atoms;
$L_4$ is —$(CH_2)_e$—, wherein e is an integer of 1 to 6;
n is an integer of 0 to 1;
$R_2$ is hydrogen, $C_{1-5}$ straight or branched alkyl, or halogen;
Y is oxygen or sulfur;
Z' is a chelator, and the chelator is

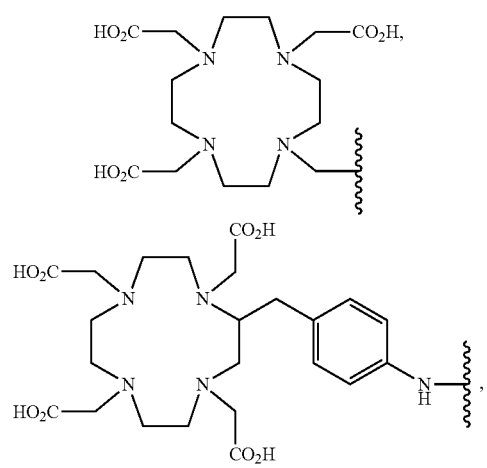

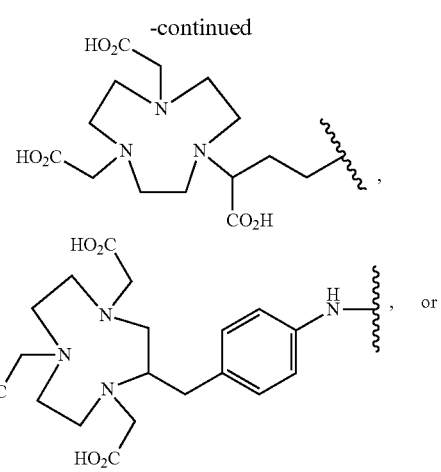

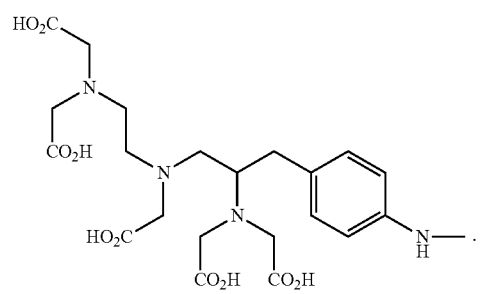

6. The compound, the stereoisomer thereof, the hydrate thereof, or the pharmaceutically acceptable salt thereof according to claim 5, wherein:
$L_1$ is —$(CH_2)_a$—, wherein a is an integer of 1 to 6;
U is a bond, or —C(O)—;
$R_1$ is -$L_5$-$CO_2H$, wherein $L_5$ is —$(CH_2)_b$—, wherein b is an integer of 1 to 4;
X is a bond, or —C(O)—;
W is a bond or —$NA_1$-, and $A_1$ is hydrogen or —$(CH_2)_c$-pyridyl,
wherein c is an integer of 0 to 1;
$L_2$ is a bond or —$(CH_2)_d$—, wherein d is an integer of 1 to 6;

Tz is

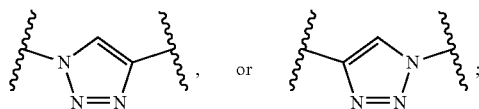 [SMILES: *c1cn(*)nn1 ; *c1cn(*)nn1]

L₃ is $C_{1-10}$ straight or branched alkylene, wherein one or more carbon atoms in alkylene can be replaced by oxygen atoms;

L₄ is —(CH₂)$_e$-, wherein e is an integer of 2 to 4;

n is an integer of 0 to 1;

R₂ is hydrogen, $C_{1-3}$ straight or branched alkyl, or halogen;

Y is oxygen or sulfur;

Z' is a chelator, and the chelator is

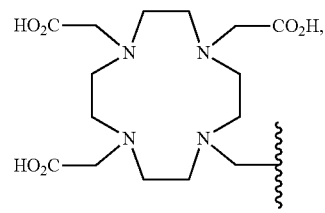

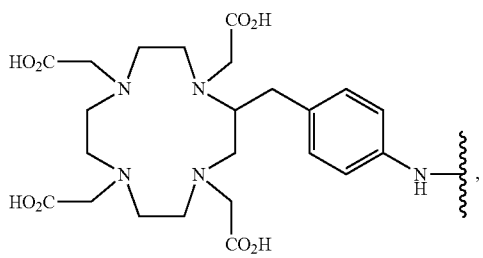

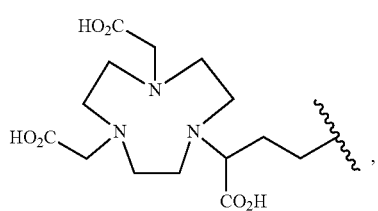

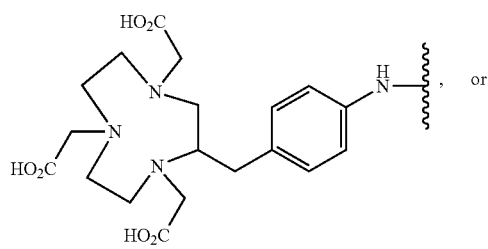

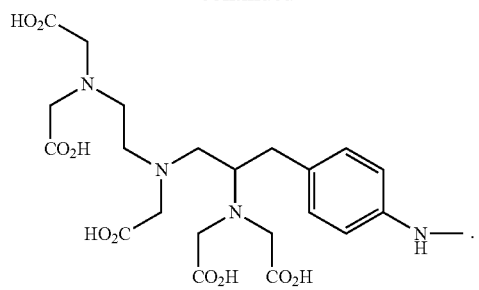

7. The compound, the stereoisomer thereof, the hydrate thereof, or the pharmaceutically acceptable salt thereof according to claim 5, wherein:

L₁ is —(CH₂)$_a$—, wherein a is an integer of 2 to 4;

U is a bond, or —C(O)—;

R₁ is -L₅-CO₂H, wherein L₅ is —(CH₂)$_b$—, wherein b is an integer of 1 to 2;

X is a bond, or —C(O)—;

W is a bond or —NA₁-, and A₁ is hydrogen or pyridyl;

L₂ is a bond or —(CH₂)$_d$—, wherein d is an integer of 1 to 2;

Tz is a bond,

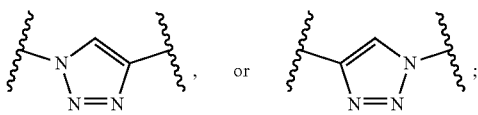

L₃ is $C_{1-8}$ straight alkylene, wherein one or more carbon atoms in alkylene can be replaced by oxygen atoms;

L₄ is —(CH₂)₃—;

n is an integer of 0 to 1;

R₂ is hydrogen, methyl, or halogen;

Y is oxygen;

Z' is a chelator, and the chelator is

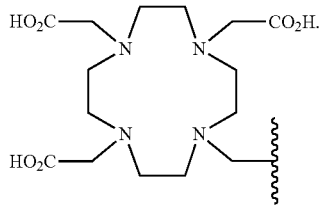 [SMILES: *CN1CCN(CC(=O)O)CCN(CC(=O)O)CCN(CC(=O)O)CC1]

8. The compound, the stereoisomer thereof, the hydrate thereof, or the pharmaceutically acceptable salt thereof according to claim 5, wherein the compound represented by formula 2 is selected from the group consisting of the following compounds:

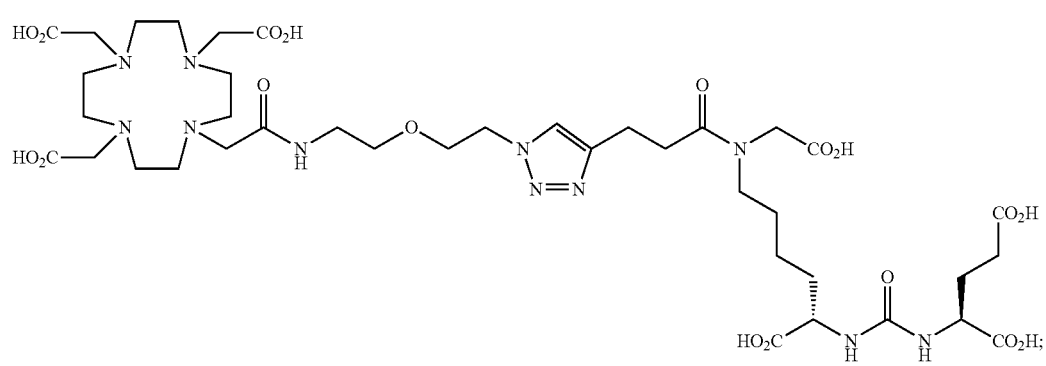
(3)
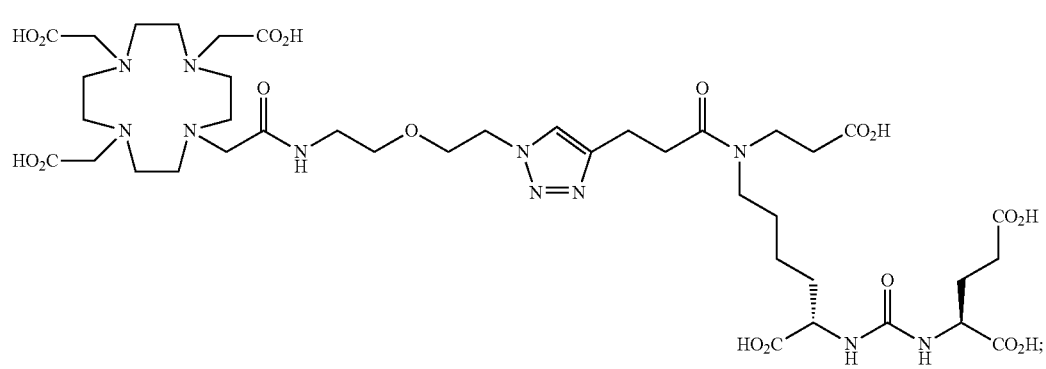
(4)
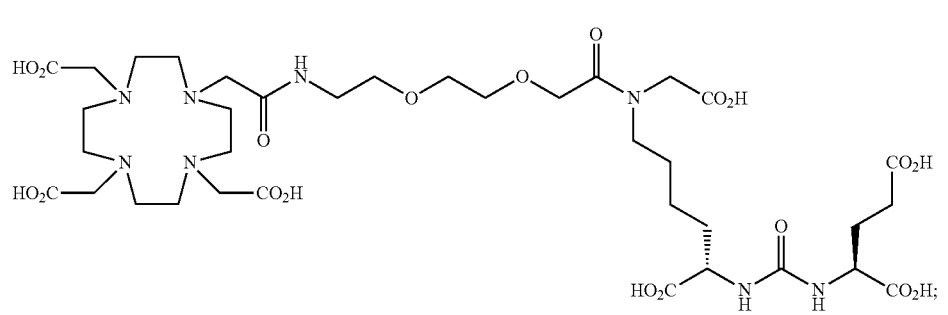
(5)
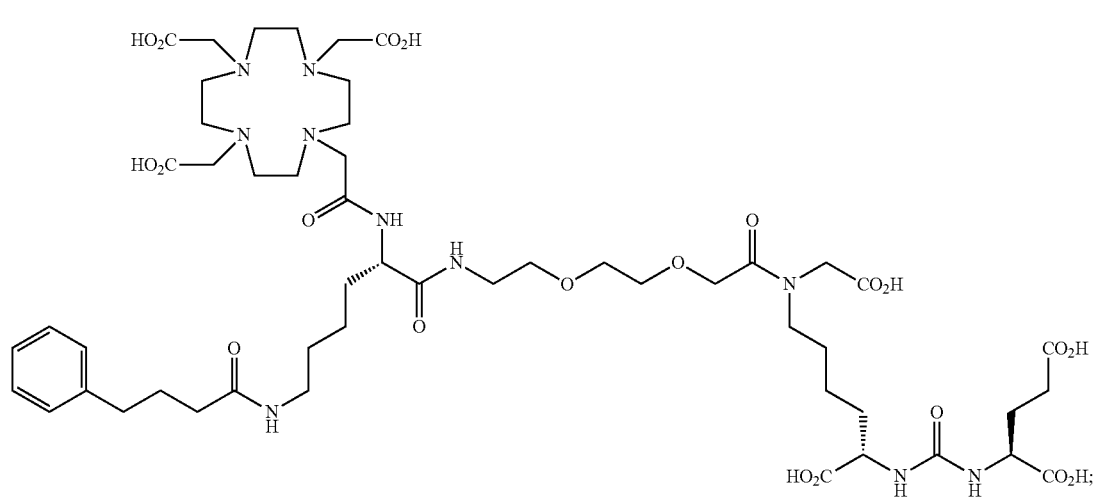
(6)

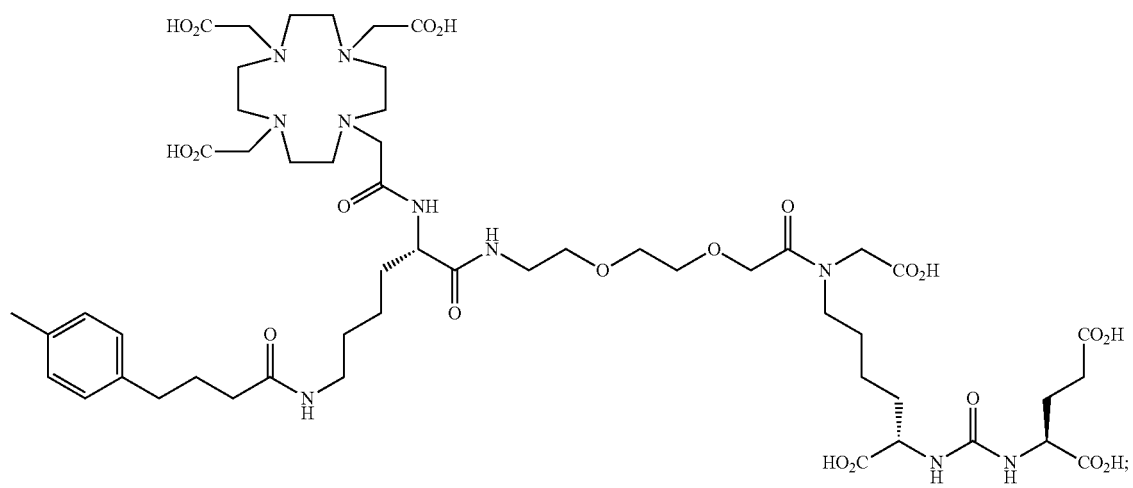
(7)
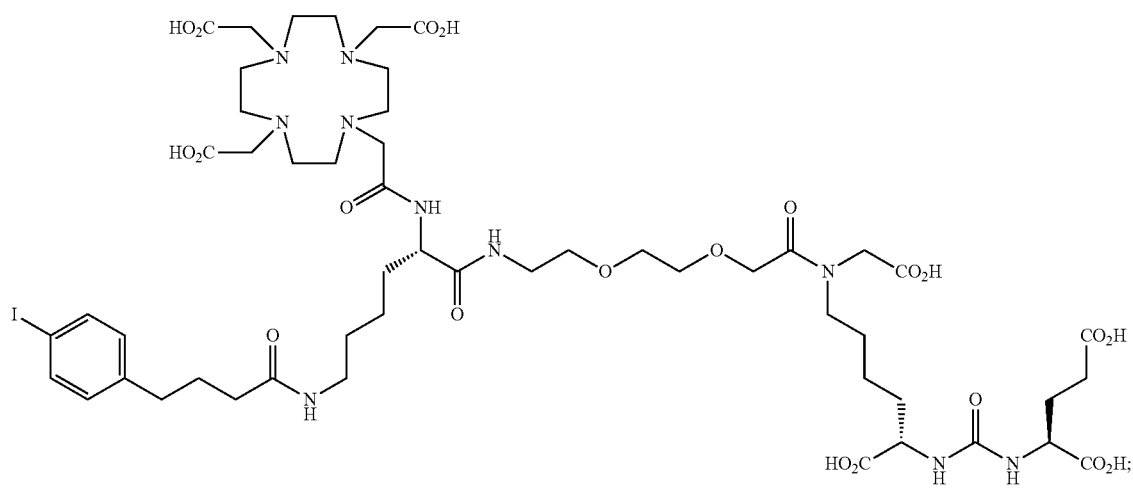
(8)
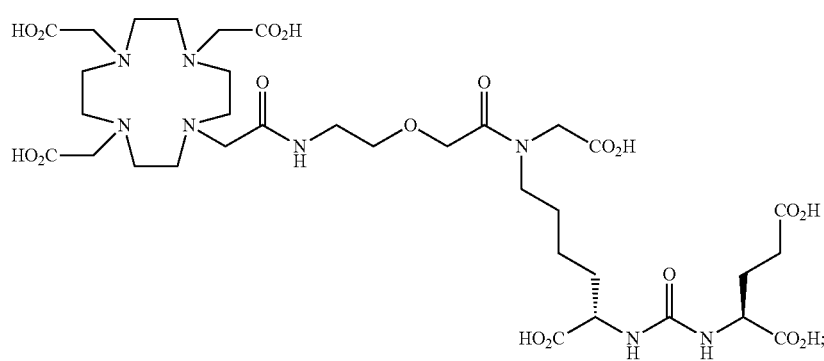
(9)

(10)
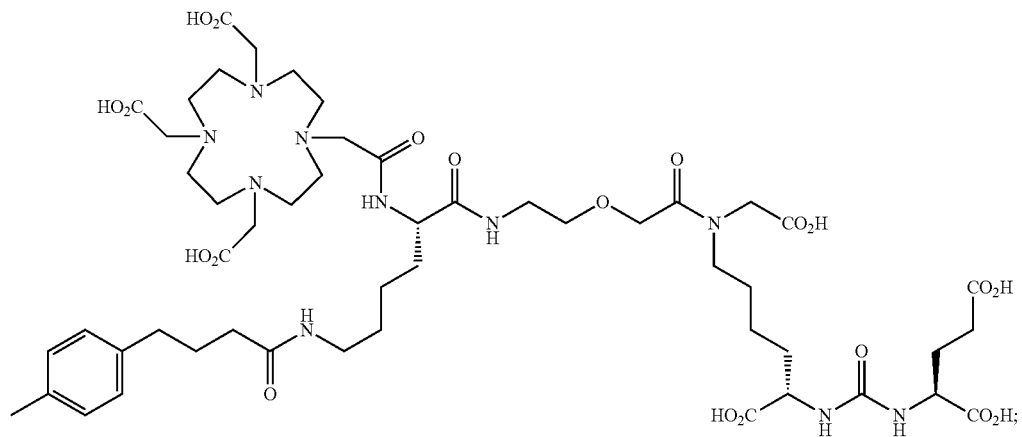
(11)
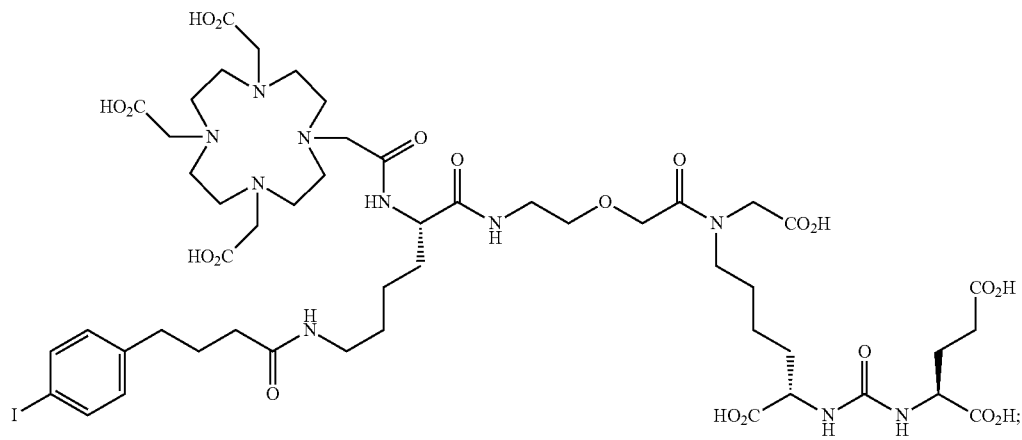
(12)
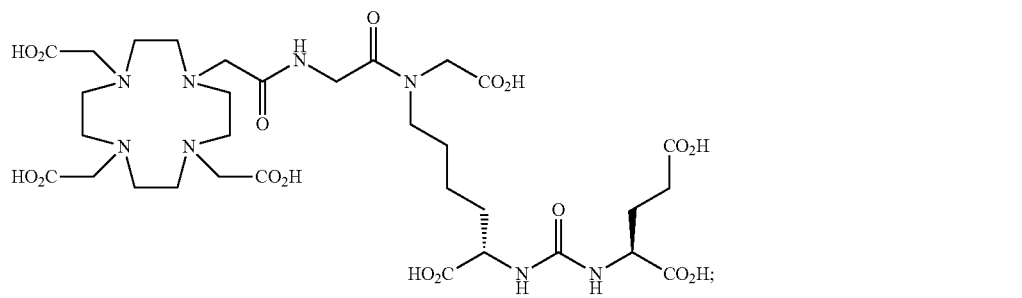
(13)
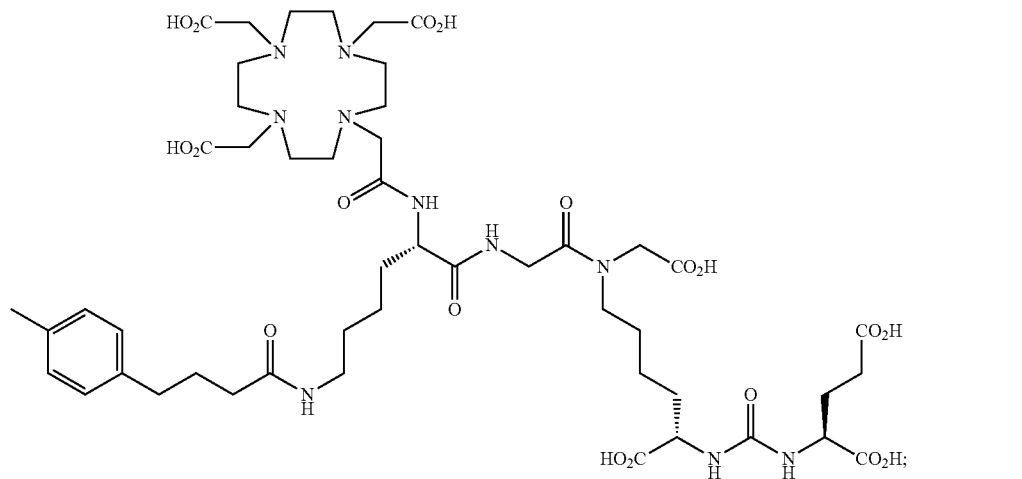

(14)

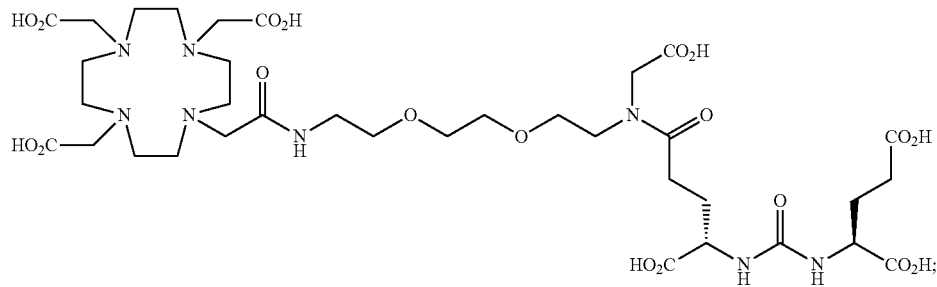

(15)

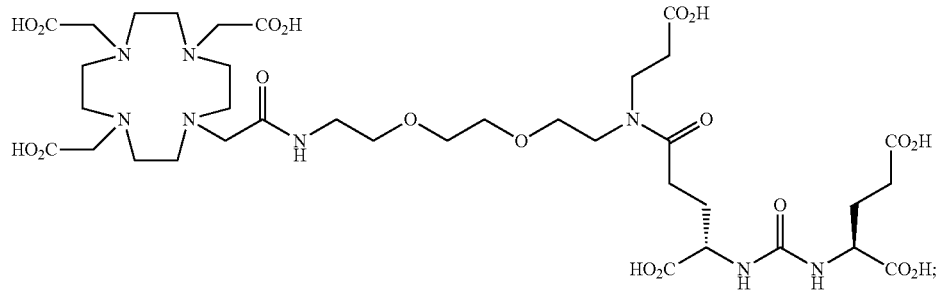

(16)

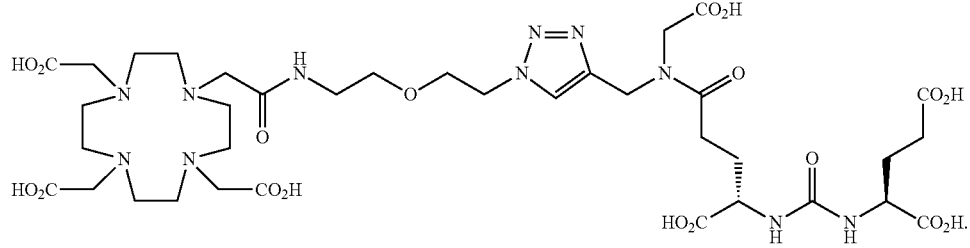

9. A composition for diagnosing prostate cancer comprising the compound, the stereoisomer thereof, the hydrate thereof, or the pharmaceutically acceptable salt thereof of claim 1 as an active ingredient.

10. The composition for diagnosing prostate cancer according to claim 9, wherein the composition diagnoses prostate cancer by selectively binding the compound to PSMA (Prostate-Specific Membrane Antigen) over-expressed in prostate cancer cells.

11. A pharmaceutical composition for preventing or treating prostate cancer comprising the compound, the stereoisomer thereof, the hydrate thereof, or the pharmaceutically acceptable salt thereof of claim 1 as an active ingredient.

12. A method for diagnosing or treating prostate cancer in a subject, said method comprising administering a pharmaceutically effective amount of the compound, the stereoisomer thereof, the hydrate thereof, or the pharmaceutically acceptable salt thereof of claim 1 as an active ingredient to the subject.

* * * * *